United States Patent
Menéndez Buján et al.

(10) Patent No.: US 12,215,158 B2
(45) Date of Patent: Feb. 4, 2025

(54) CD1a ANTIBODY-EXPRESSING CAR T-CELLS FOR THE TREATMENT OF CD1a-POSITIVE CANCER

(71) Applicants: FUNDACIÓN INSTITUTO DE INVESTIGACIÓN CONTRA LA LEUCEMIA JOSEP CARRERAS (IJC), Barcelona (ES); INSTITUCIÓ CATALANA DE RECERCA I ESTUDIS AVANÇ ATS (ICREA), Barcelona (ES); FUNDACIÓ INSTITUT D'INVESTIGACIÓ EN CIENCIES DE LA SALUT GERMANS TRIAS I PUJOL (IGTP), Badalona (ES)

(72) Inventors: Pablo Menéndez Buján, Barcelona (ES); Diego Sanchez Martínez, Barcelona (ES); Clara Bueno Uroz, Barcelona (ES); Francisco Gutiérrez Agüera, Barcelona (ES); Heleia Roca-Ho, Barcelona (ES)

(73) Assignees: FUNDACÍON INSTITUTO DE INVESTIGACÍON CONTRA LA LEUCEMIA JOSEP CARRERAS (IJC), Barcelona (ES); INSTITUCIÓ CATALANA DE RECERCA I ESTUDIS AVANATS (ICREA), Barcelona (ES); FUNDACIÓ INSTITUT D'INVESTIGACIÓ EN CIENCIES DE LA SALUT GERMANS TRIAS I PUJOL (IGTP), Badalona (ES)

( * ) Notice: Subject to any disclaimer, the term of this patent is extended or adjusted under 35 U.S.C. 154(b) by 843 days.

(21) Appl. No.: 17/430,705

(22) PCT Filed: Feb. 13, 2020

(86) PCT No.: PCT/EP2020/053769
§ 371 (c)(1),
(2) Date: Aug. 12, 2021

(87) PCT Pub. No.: WO2020/165350
PCT Pub. Date: Aug. 20, 2020

(65) Prior Publication Data
US 2022/0143085 A1 May 12, 2022

(30) Foreign Application Priority Data
Feb. 14, 2019 (EP) .................................. 19382104

(51) Int. Cl.
*C07K 16/28* (2006.01)
*A61K 39/00* (2006.01)
*A61P 35/00* (2006.01)
*C07K 14/705* (2006.01)
*C12N 5/0783* (2010.01)

(52) U.S. Cl.
CPC ...... *C07K 16/2833* (2013.01); *A61K 39/4611* (2023.05); *A61K 39/4631* (2023.05); *A61K 39/464429* (2023.05); *A61P 35/00* (2018.01); *C07K 14/705* (2013.01); *C12N 5/0636* (2013.01); *A61K 2239/31* (2023.05); *A61K 2239/38* (2023.05); *A61K 2239/48* (2023.05)

(58) Field of Classification Search
None
See application file for complete search history.

(56) References Cited

U.S. PATENT DOCUMENTS 5,223,409 A  6/1993  Ladner et al.

FOREIGN PATENT DOCUMENTS

| JP | 2018-522833 A | 8/2018 |
|----|---------------|--------|
| WO | WO-1990/02809 A1 | 3/1990 |
| WO | WO-1991/017271 A1 | 11/1991 |
| WO | WO-1992/001047 A1 | 1/1992 |
| WO | WO-1992/009690 A2 | 6/1992 |
| WO | WO-1992/015679 A1 | 9/1992 |
| WO | WO-1992/018619 A1 | 10/1992 |

(Continued)

OTHER PUBLICATIONS

Addo et al., Comprehensive epitope analysis of human immunodeficiency virus type 1 (HIV-1)-specific T-cell responses directed against the entire expressed HIV-1 genome demonstrate broadly directed responses, but no correlation to viral load. J Virol. Feb. 2003;77(3):2081-92.

(Continued)

*Primary Examiner* — Christine J Saoud
*Assistant Examiner* — Jon M Lockard
(74) *Attorney, Agent, or Firm* — McCarter & English, LLP; Jill Mello; Yelena Margolin

(57) ABSTRACT

Relapsed/refractory T-cell acute lymphoblastic leukemia (T-ALL) has a dismal outcome, and no effective targeted immunotherapies for T-ALL exist. The extension of chimeric antigen receptor T-cells (CARTs) to T-ALL remains challenging because the shared expression of target antigens between CARTs and T-ALL blasts leads to CARTs fratricide. CD 1a is exclusively expressed in cortical T-ALLs, a major subset of T-ALL. The expression of CD 1a is restricted to cortical thymocytes and neither CD34+ progenitors nor T-cells express CD 1a during ontogeny, confining the risk of on-target/off-tumor toxicity. The present invention provides CARs comprising a CD 1a-targeting moiety which may be transduced or transformed into T cells. The resultant CARTs are suitable for the treatment of cortical T-ALLs.

Figure 1:
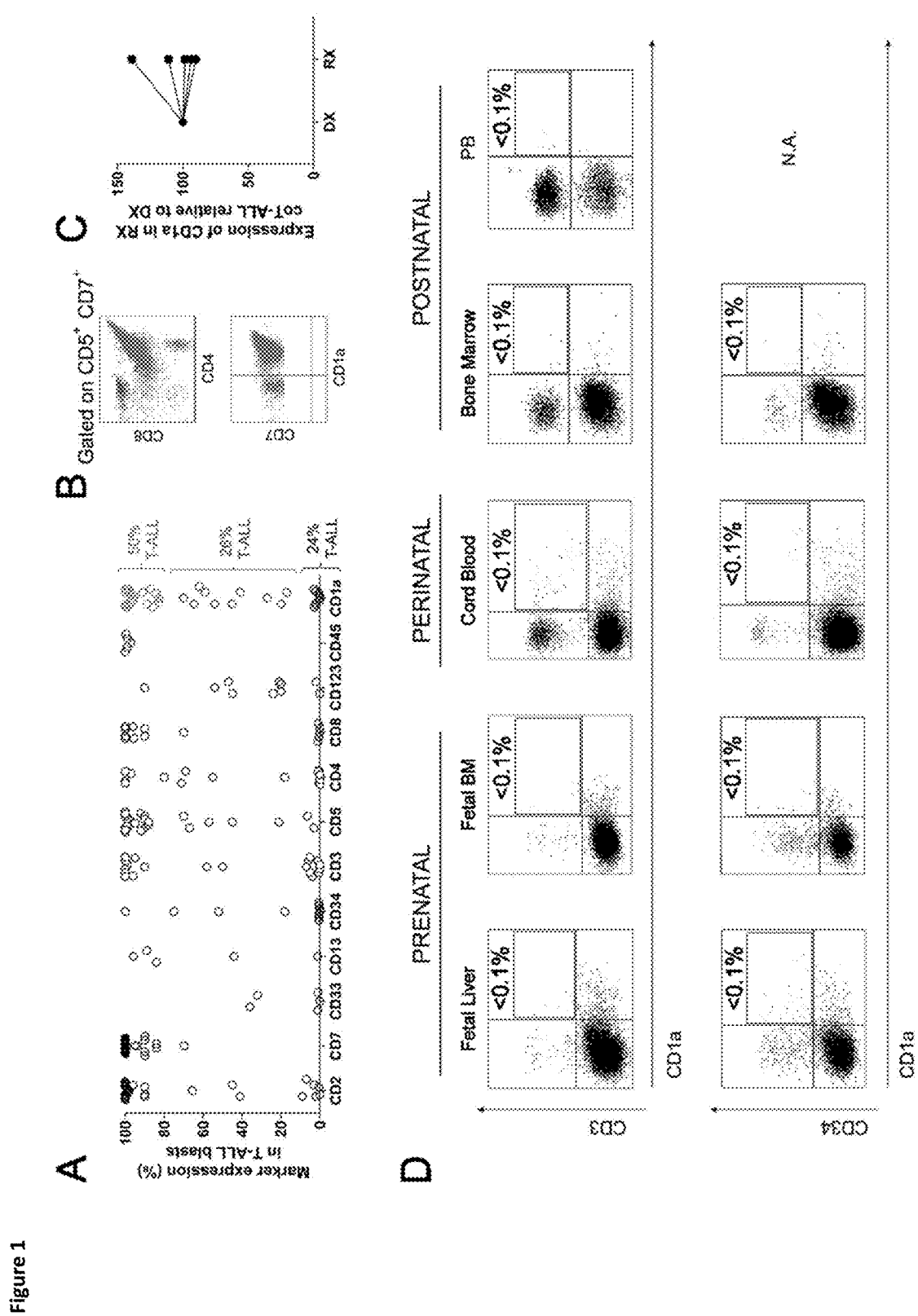
Figure 1:
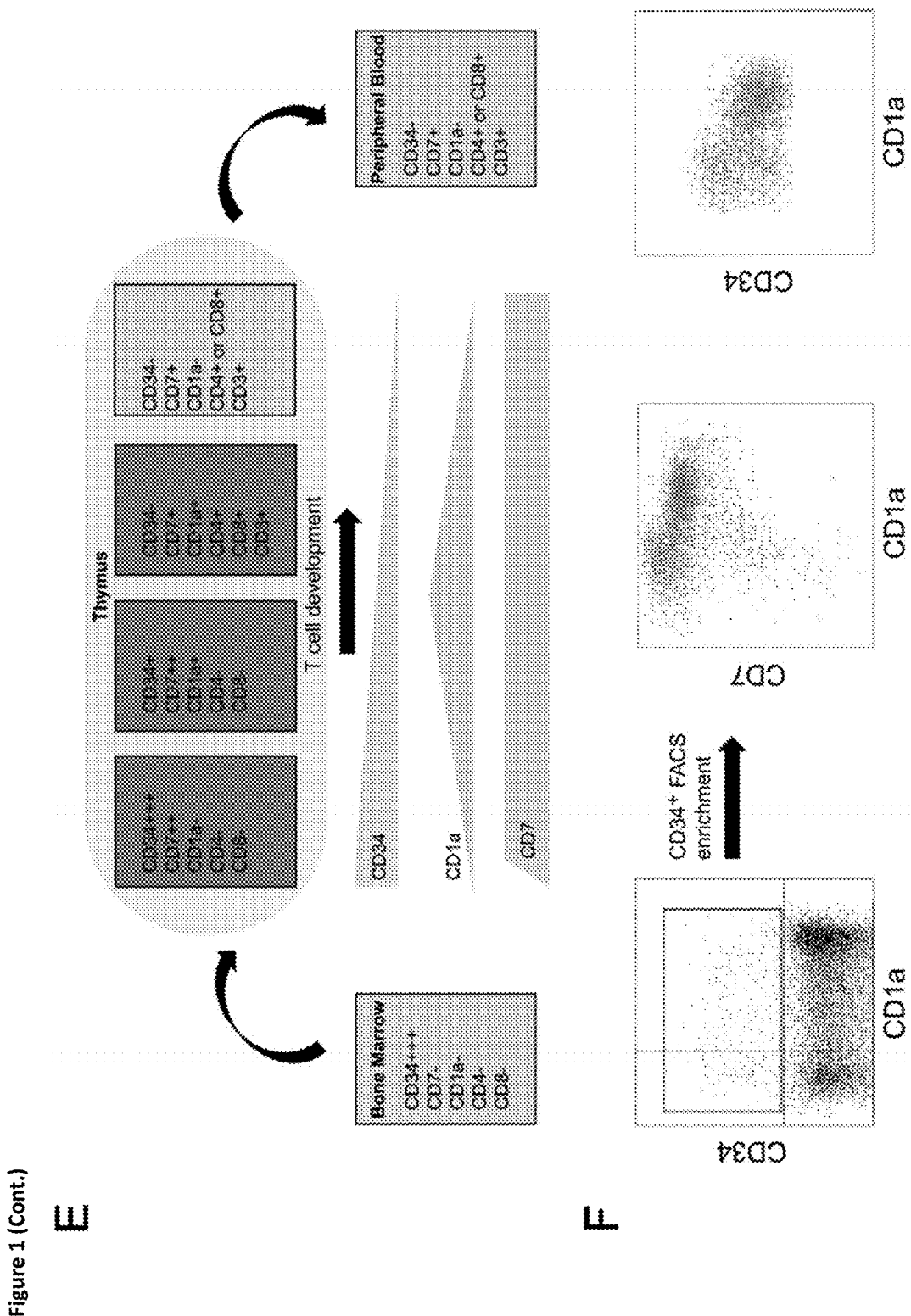

17 Claims, 26 Drawing Sheets
Specification includes a Sequence Listing.

(56) References Cited

FOREIGN PATENT DOCUMENTS

| WO | WO-1992/020791 A1 | 11/1992 |
|---|---|---|
| WO | WO-1993/001288 A1 | 1/1993 |
| WO | WO-2016/054555 A2 | 4/2016 |

OTHER PUBLICATIONS

Al-Lazikani et al., Standard conformations for the canonical structures of immunoglobulins. J Mol Biol. Nov. 7, 1997;273(4):927-48.
Amiot et al., Heterogeneity of the first cluster of differentiation: characterization and epitopic mapping of three CD1 molecules on normal human thymus cells. J Immunol. Mar. 1, 1986;136(5):1752-8.
Ballerini et al., Impact of genotype on survival of children with T-cell acute lymphoblastic leukemia treated according to the French protocol FRALLE-93: the effect of TLX3/HOX11L2 gene expression on outcome. Haematologica. Nov. 2008;93(11):1658-65.
Bannas et al., Nanobodies and Nanobody-Based Human Heavy Chain Antibodies as Antitumor Therapeutics. Front Immunol. Nov. 22, 2017;8:1603, 13 pages.
Barbas et al., Assembly of combinatorial antibody libraries on phage surfaces: the gene III site. Proc Natl Acad Sci U S A. Sep. 15, 1991;88(18):7978-82.
Bechan et al., A Human Anti-CD1a Monoclonal Antibody for Targeted Immunotherapy in Langerhans Cell Histiocytosis and Hematologic Malignancies. Blood. 2005;106(11):4815.
Bechan et al., Phage display generation of a novel human anti-CD1A monoclonal antibody with potent cytolytic activity. Br J Haematol. Nov. 2012;159(3):299-310.
Bene et al., Proposals for the immunological classification of acute leukemias. European Group for the Immunological Characterization of Leukemias (EGIL). Leukemia. Oct. 1995;9(10):1783-6.
Bertschinger et al., Selection of single domain binding proteins by covalent DNA display. Protein Eng Des Sel. Feb. 2007;20(2):57-68.
Brentjens et al., CD19-targeted T cells rapidly induce molecular remissions in adults with chemotherapy-refractory acute lymphoblastic leukemia. Sci Transl Med. Mar. 20, 2013;5(177):177ra38, 19 pages.
Bueno et al., Bone marrow mesenchymal stem cells from patients with aplastic anemia maintain functional and immune properties and do not contribute to the pathogenesis of the disease. Haematologica. Jul. 2014;99(7):1168-75.
Burger et al., Heterogeneity of T-acute lymphoblastic leukemia (T-ALL) cell lines: suggestion for classification by immunophenotype and T-cell receptor studies. Leuk Res. Jan. 1999;23(1):19-27.
Carrera Silva et al., CD207+CD1a+ cells circulate in pediatric patients with active Langerhans cell histiocytosis. Blood. Oct. 26, 2017;130(17):1898-1902.
Chantepie et al., Hematogones: an overview. Leuk Res. Nov. 2013;37(11):1404-11.
Cheson et al., Revised recommendations of the International Working Group for Diagnosis, Standardization of Response Criteria, Treatment Outcomes, and Reporting Standards for Therapeutic Trials in Acute Myeloid Leukemia. J Clin Oncol. Dec. 15 2003;21(24):4642-9.
Clackson et al., Making antibody fragments using phage display libraries. Nature. Aug. 15, 1991;352(6336):624-8.
Cooper et al., An "off-the-shelf" fratricide-resistant CAR-T for the treatment of T cell hematologic malignancies. Leukemia. Sep. 2018;32(9):1970-1983.
Dalmau et al., Highly pathogenic adapted HIV-1 strains limit host immunity and dictate rapid disease progression. AIDS. Jun. 1, 2014;28(9):1261-72, pre-publication edition.
Dohner et al., Diagnosis and management of acute myeloid leukemia in adults: recommendations from an international expert panel, on behalf of the European LeukemiaNet. Blood. Jan. 21, 2010;115(3):453-74.
Eisenhauer et al., New response evaluation criteria in solid tumours: revised RECIST guideline (version 1.1). Eur J Cancer. Jan. 2009;45(2):228-47.

Frankel et al., Therapy of patients with T-cell lymphomas and leukemias using an anti-CD7 monoclonal antibody-ricin A chain immunotoxin. Leuk Lymphoma. Jul. 1997;26(3-4):287-98.
Frejd et al., Affibody molecules as engineered protein drugs. Exp Mol Med. Mar. 24, 2017;49(3):e306, 8 pages.
Fry et al., CD22-targeted CAR T cells induce remission in B-ALL that is naive or resistant to CD19-targeted CAR immunotherapy. Nat Med. Jan. 2018;24(1):20-28.
Fuchs et al., Targeting recombinant antibodies to the surface of *Escherichia coli*: fusion to a peptidoglycan associated lipoprotein. Biotechnology (N Y). Dec. 1991;9(12):1369-72.
Furue et al., Epitopes for CD1a, CD1b, and CD1c antigens are differentially mapped on Langerhans cells, dermal dendritic cells, keratinocytes, and basement membrane zone in human skin. J Am Acad Dermatol. Sep. 1992;27(3):419-26.
Galy et al., Precursors of CD3+CD4+CD8+ cells in the human thymus are defined by expression of CD34. Delineation of early events in human thymic development. J Exp Med. Aug. 1, 1993;178(2):391-401.
Garcia-Peydro et al., The NOTCH1/CD44 axis drives pathogenesis in a T cell acute lymphoblastic leukemia model. J Clin Invest. Jul. 2, 2018;128(7):2802-2818.
Gardner et al., Intent-to-treat leukemia remission by CD19 CAR T cells of defined formulation and dose in children and young adults. Blood. Jun. 22, 2017;129(25):3322-3331.
Garrard et al., Fab assembly and enrichment in a monovalent phage display system. Biotechnology (N Y). Dec. 1991;9(12):1373-7.
Gokbuget et al., Inclusion and response criteria for clinical trials in relapsed/refractory acute lymphoblastic leukemia and usefulness of historical control trials. Haematologica. 2017;102:e118.
Gomes-Silva et al., CD7-edited T cells expressing a CD7-specific CAR for the therapy of T-cell malignancies. Blood. Jul. 20, 2017;130(3):285-296.
Gram et al., In vitro selection and affinity maturation of antibodies from a naive combinatorial immunoglobulin library. Proc Natl Acad Sci U S A. Apr. 15, 1992;89(8):3576-80.
Griffiths et al., Human anti-self antibodies with high specificity from phage display libraries. EMBO J. Feb. 1993; 12(2):725-34.
Hawkins et al., Selection of phage antibodies by binding affinity. Mimicking affinity maturation. J Mol Biol. Aug. 5, 1992;226(3):889-96.
Hay et al., Bacteriophage cloning and *Escherichia coli* expression of a human IgM Fab. Hum Antibodies Hybridomas. Apr. 1992;3(2):81-5.
Hoogenboom et al., Multi-subunit proteins on the surface of filamentous phage: methodologies for displaying antibody (Fab) heavy and light chains. Nucleic Acids Res. Aug. 11, 1991;19(15):4133-7.
Humphries, Adoptive cell therapy: Honing that killer instinct. Nature. Dec. 19, 2013;504(7480):S13-5.
Hunger et al., Acute Lymphoblastic Leukemia in Children. N Engl J Med. Oct. 15, 2015;373(16):1541-52.
Huse et al., Generation of a large combinatorial library of the immunoglobulin repertoire in phage lambda. Science. Dec. 8, 1989;246(4935):1275-81.
Junca et al., Adult T-cell leukemia/lymphoma with an unusual CD1a positive phenotype. Cytometry B Clin Cytom. 2014;86B:292-296.
Karrman et al., Clinical and cytogenetic features of a population-based consecutive series of 285 pediatric T-cell acute lymphoblastic leukemias: rare T-cell receptor gene rearrangements are associated with poor outcome. Genes Chromosomes Cancer. Sep. 2009;48(9):795-805.
Karrman et al., Pediatric T-cell acute lymphoblastic leukemia. Genes Chromosomes Cancer. Feb. 2017;56(2):89-116, pre-publication edition.
Kelly et al., Successful in vivo immunolocalization of Langerhans cell histiocytosis with use of a monoclonal antibody, NA1/34. J Pediatr. Nov. 1994;125(5 Pt 1):717-22.
Koide et al., Teaching an old scaffold new tricks: monobodies constructed using alternative surfaces of the FN3 scaffold. J Mol Biol. Jan. 13, 2012;415(2):393-405.

(56) References Cited

OTHER PUBLICATIONS

Kurobe et al., Complete but not partial thymectomy in early infancy reduces T-cell-mediated immune response: Three-year tracing study after pediatric cardiac surgery. J Thorac Cardiovasc Surg. 2013;145:656-62.
Lee et al., Design of a binding scaffold based on variable lymphocyte receptors of jawless vertebrates by module engineering. Proc Natl Acad Sci U S A. Feb. 28, 2012;109(9):3299-304.
LeMaistre et al., Phase I trial of H65-RTA immunoconjugate in patients with cutaneous T-cell lymphoma. Blood. Sep. 1, 1991;78(5):1173-82.
Lepretre et al., Adult T-type lymphoblastic lymphoma: Treatment advances and prognostic indicators. Exp Hematol. Jul. 2017;51:7-16, pre-publication edition.
Li et al., The EMBL-EBI bioinformatics web and programmatic tools framework. Nucleic Acids Res. Jul. 1, 2015;43(W1):W580-4.
Lim et al., The Principles of Engineering Immune Cells to Treat Cancer. Cell. Sep. 9, 2017. 168;724-740.
Litzow et al., How I treat T-cell acute lymphoblastic leukemia in adults. Blood. Aug. 13, 2015;126(7):833-41.
Maciocia et al., Targeting the T cell receptor beta-chain constant region for immunotherapy of T cell malignancies. Nat Med. Dec. 2017;23(12):1416-1423, pre-publication edition.
Mamonkin et al., A T-cell-directed chimeric antigen receptor for the selective treatment of T-cell malignancies. Blood. Aug. 20, 2015;126(8):983-92.
Marks et al., T-cell acute lymphoblastic leukemia in adults: clinical features, immunophenotype, cytogenetics, and outcome from the large randomized prospective trial (UKALL XII/ECOG 2993). Blood. Dec. 10, 2009;114(25):5136-45.
Martin-Gayo et al., Spatially restricted JAG1-Notch signaling in human thymus provides suitable DC developmental niches. J Exp Med. Nov. 6, 2017;214(11):3361-3379.
Maude et al., Chimeric antigen receptor T cells for sustained remissions in leukemia. N Engl J Med. Oct. 16, 2014;371(16):1507-17.
Mendes et al., The relevance of PTEN-AKT in relation to NOTCH1-directed treatment strategies in T-cell acute lymphoblastic leukemia. Haematologica. Sep. 2016;101(9):1010-7.
Menendez et al., Adoptive Cellular Immunotherapy Using CD1A Cart-Cells for Cortical T-Cell Acute Lymphoblastic Leukemia. Experimental Hematology. 2018;64:S85, Abstract No. 3107.
Menendez et al., Bone marrow mesenchymal stem cells from infants with MLL-AF4+ acute leukemia harbor and express the MLL-AF4 fusion gene. J Exp Med. Dec. 21, 2009;206(13):3131-41.
Miliotou et al., CAR T-cell Therapy: A New Era in Cancer Immunotherapy. Curr Pharm Biotechnol. 2018;19(1):5-18.
Munoz-Lopez et al., Cellular Ontogeny and Hierarchy Influence the Reprogramming Efficiency of Human B Cells into Induced Pluripotent Stem Cells. Stem Cells. Mar. 2016;34(3):581-7.
Munoz-Lopez et al., Development Refractoriness of MLL-Rearranged Human B Cell Acute Leukemias to Reprogramming into Pluripotency. Stem Cell Reports. Oct. 11, 2016;7(4):602-618.
Murray et al., Diagnostic and therapeutic evaluation of an anti-Langerhans cell histiocytosis monoclonal antibody (NA1/34) in a new xenograft model. J Invest Dermatol. Jan. 2000;114(1):127-34.
Niehues et al., A classification based on T cell selection-related phenotypes identifies a subgroup of childhood T-ALL with favorable outcome in the COALL studies. Leukemia. Apr. 1999;13(4):614-7.
Parret et al., Critical reflections on synthetic gene design for recombinant protein expression. Curr Opin Struct Biol. Jun. 2016;38:155-62.
Pluckthun et al., Designed ankyrin repeat proteins (DARPins): binding proteins for research, diagnostics, and therapy. Annu Rev Pharmacol Toxicol. 2015;55:489-511.
Png et al., Blockade of CD7 expression in T cells for effective chimeric antigen receptor targeting of T-cell malignancies. Blood advances. Nov. 28, 2017;1(25):2348-2360.
Prieto et al., Activated KRAS Cooperates with MLL-AF4 to Promote Extramedullary Engraftment and Migration of Cord Blood CD34+ HSPC but Is Insufficient to Initiate Leukemia. Cancer Res. Apr. 15, 2016;76(8):2478-89.
Qasim et al., Progress and prospects for engineered T cell therapies. Br J Haematol. Sep. 2014;166(6):818-29.
Rasaiyaah et al., TCRalphabeta/CD3 disruption enables CD3-specific antileukemic T cell immunotherapy. JCI Insight. 2018;3(13):e99442, 13 pages.
Recasens-Zorzo et al., Pharmacological modulation of CXCR4 cooperates with BET bromodomain inhibition in diffuse large B-cell lymphoma. Haematologica. Apr. 2019;104(4):778-788.
Reiter et al., Engineering antibody Fv fragments for cancer detection and therapy: disulfide-stabilized Fv fragments. Nat Biotechnol. Oct. 1996;14(10):1239-45.
Reverdatto et al., Peptide aptamers: development and applications. Curr Top Med Chem. 2015;15(12):1082-101.
Rice et al., EMBOSS: the European Molecular Biology Open Software Suite. Trends Genet. Jun. 2000;16(6):276-7.
Riviere et al., Chimeric Antigen Receptors: A Cell and Gene Therapy Perspective. Mol Ther. May 3, 2017;25(5):1117-1124.
Rodriguez et al., Expression of FUS-CHOP fusion protein in immortalized/transformed human mesenchymal stem cells drives mixoid liposarcoma formation. Stem Cells. Oct. 2013;31(10):2061-72.
Sanchez-Martinez et al., Adoptive Cellular Immunotherapy using CD1a CART-cells for Treatment of Cortical Pediatric T-cell Acute Lymphoblastic Leukemia. Klin Padiatr. 2018;230(3):174.
Sanchez-Martinez et al., Fratricide-resistant CD1a-specific CAR T cells for the treatment of cortical T-cell acute lymphoblastic leukemia. Blood. May 23, 2019;133(21):2291-2304.
Santa Cruz Biotechnology, Inc., CD1A (NA1/34):sc53035. Retrieved online at: www.scbt.com. 1 page. Apr. 25, 2017.
Schneider et al., New recurring cytogenetic abnormalities and association of blast cell karyotypes with prognosis in childhood T-cell acute lymphoblastic leukemia: a pediatric oncology group report of 343 cases. Blood. Oct. 1, 2000;96(7):2543-9.
Skerra et al., Alternative binding proteins: anticalins—harnessing the structural plasticity of the lipocalin ligand pocket to engineer novel binding activities. FEBS J. Jun. 2008;275(11):2677-83.
Skrlec et al., Non-immunoglobulin scaffolds: a focus on their targets. Trends Biotechnol. Jul. 2015;33(7):408-18, pre-publication edition.
Sutton et al., Persistent MRD before and after allogeneic BMT predicts relapse in children with acute lymphoblastic leukaemia. Br J Haematol. Feb. 2015;168(3):395-404.
Van Den Broek et al., Human neonatal thymectomy induces altered B-cell responses and autoreactivity. Eur J Immunol. Nov. 2017;47(11):1970-1981.
Van Den Broek et al., Neonatal thymectomy reveals differentiation and plasticity within human naive T cells. JCI. Mar. 2016;126(3):1126-1136.
Van Grotel et al., Prognostic significance of molecular-cytogenetic abnormalities in pediatric T-ALL is not explained by immunophenotypic differences. Leukemia. Jan. 2008;22(1):124-31.
Van Kroonenburgh et al., Human immunological response to mouse monoclonal antibodies in the treatment or diagnosis of malignant diseases. Nucl Med Commun. Nov. 1988;9(11):919-30.
Weber, Assessing tumor response to therapy. J Nucl Med. May 2009;50 Suppl 1:1S-10S.
Weng et al., Activating mutations of NOTCH1 in human T cell acute lymphoblastic leukemia. Science. Oct. 8, 2004;306(5694):269-71.
European Office Action for Application No. 19382104.8, dated Jul. 30, 2019, 6 pages.
International Search Report and Written Opinion for Application No. PCT/EP2020/053769, dated May 29, 2020, 14 pages.

SEQUENCE LISTING

```
<160> NUMBER OF SEQ ID NOS: 12

<210> SEQ ID NO 1
<211> LENGTH: 6
<212> TYPE: PRT
<213> ORGANISM: Artificial Sequence
<220> FEATURE:
<223> OTHER INFORMATION: LCDR1

<400> SEQUENCE: 1

Gln Asp Ile Asn Lys Tyr
1               5

<210> SEQ ID NO 2
<211> LENGTH: 493
<212> TYPE: PRT
<213> ORGANISM: Artificial Sequence
<220> FEATURE:
<223> OTHER INFORMATION: Full sequence of the CAR

<400> SEQUENCE: 2

Met Ala Leu Pro Val Thr Gly Leu Leu Leu Ser Leu Gly Leu Leu Leu
1               5                   10                  15

His Ala Ala Arg Pro Thr Gly Gln Val Gln Leu Gln Gln Ser Gly Ala
            20                  25                  30

Glu Leu Ala Arg Pro Gly Ala Ser Val Lys Met Ser Cys Lys Ala Ser
        35                  40                  45

Gly Tyr Ala Phe Ser Thr Tyr Thr Met His Trp Val Lys Gln Arg Pro
    50                  55                  60

Arg Gln Gly Leu Glu Trp Ile Gly Tyr Ile Asn Pro Asn Ser Ala Ser
65                  70                  75                  80

Thr Ser Tyr Asn Glu Asn Phe Lys Asp Lys Ala Thr Leu Thr Ala Asp
                85                  90                  95

Lys Ser Ser Asn Thr Ala Tyr Met His Leu Ser Ser Leu Thr Ser Glu
```

```
                  100                 105                  110
Asp Ser Ala Val Tyr Tyr Cys Ala Arg Gly Phe Tyr Thr Met Asp Tyr
                115                 120                 125
Trp Gly Gln Gly Thr Ser Val Thr Val Ser Ser Gly Gly Gly Gly Ser
                130                 135                 140
Gly Gly Gly Gly Ser Gly Gly Gly Ser Gly Gly Gly Gly Ser Arg
145                 150                 155                 160
Asp Ile Gln Met Thr Gln Ser Pro Ser Ser Leu Ser Ala Ser Leu Gly
                165                 170                 175
Gly Lys Val Thr Ile Thr Cys Gln Ala Ser Gln Asp Ile Asn Lys Tyr
                180                 185                 190
Ile Ala Trp Tyr Gln Phe Lys Pro Gly Lys Gly Pro Arg Leu Leu Ile
                195                 200                 205
His Tyr Thr Ser Thr Leu Gln Pro Ala Ile Pro Ser Arg Phe Ser Gly
                210                 215                 220
Ser Gly Ser Gly Arg Glu Tyr Ser Phe Ser Ile Ser Asn Leu Glu Pro
225                 230                 235                 240
Glu Asp Ile Ala Thr Tyr Tyr Cys Leu His Tyr Asp Asn Leu Pro Trp
                245                 250                 255
Thr Phe Gly Gly Gly Thr Lys Leu Glu Ile Lys Arg Ala Thr Thr Thr
                260                 265                 270
Pro Ala Pro Arg Pro Pro Thr Pro Ala Pro Thr Ile Ala Ser Gln Pro
                275                 280                 285
Leu Ser Leu Arg Pro Glu Ala Cys Arg Pro Ala Ala Gly Gly Ala Val
                290                 295                 300
His Thr Arg Gly Leu Asp Phe Ala Cys Asp Ile Tyr Ile Trp Ala Pro
305                 310                 315                 320
Leu Ala Gly Thr Cys Gly Val Leu Leu Leu Ser Leu Val Ile Thr Leu
                325                 330                 335
Tyr Cys Lys Arg Gly Arg Lys Lys Leu Leu Tyr Ile Phe Lys Gln Pro
                340                 345                 350
Phe Met Arg Pro Val Gln Thr Thr Gln Glu Glu Asp Gly Cys Ser Cys
                355                 360                 365
Arg Phe Pro Glu Glu Glu Gly Gly Cys Glu Leu Arg Val Lys Phe
                370                 375                 380
Ser Arg Ser Ala Asp Ala Pro Ala Tyr Gln Gln Gly Gln Asn Gln Leu
385                 390                 395                 400
Tyr Asn Glu Leu Asn Leu Gly Arg Arg Glu Glu Tyr Asp Val Leu Asp
                405                 410                 415
Lys Arg Arg Gly Arg Asp Pro Glu Met Gly Gly Lys Pro Gln Arg Arg
                420                 425                 430
Lys Asn Pro Gln Glu Gly Leu Tyr Asn Glu Leu Gln Lys Asp Lys Met
                435                 440                 445
Ala Glu Ala Tyr Ser Glu Ile Gly Met Lys Gly Glu Arg Arg Arg Gly
                450                 455                 460
Lys Gly His Asp Gly Leu Tyr Gln Gly Leu Ser Thr Ala Thr Lys Asp
465                 470                 475                 480
Thr Tyr Asp Ala Leu His Met Gln Ala Leu Pro Pro Arg
                485                 490

<210> SEQ ID NO 3
<211> LENGTH: 9
<212> TYPE: PRT
<213> ORGANISM: Artificial Sequence
```

```
<220> FEATURE:
<223> OTHER INFORMATION: LCDR3

<400> SEQUENCE: 3

Leu His Tyr Asp Asn Leu Pro Trp Thr
1               5

<210> SEQ ID NO 4
<211> LENGTH: 8
<212> TYPE: PRT
<213> ORGANISM: Artificial Sequence
<220> FEATURE:
<223> OTHER INFORMATION: HCDR1

<400> SEQUENCE: 4

Gly Tyr Ala Phe Ser Thr Tyr Thr
1               5

<210> SEQ ID NO 5
<211> LENGTH: 8
<212> TYPE: PRT
<213> ORGANISM: Artificial Sequence
<220> FEATURE:
<223> OTHER INFORMATION: HCDR2

<400> SEQUENCE: 5

Ile Asn Pro Asn Ser Ala Ser Thr
1               5

<210> SEQ ID NO 6
<211> LENGTH: 9
<212> TYPE: PRT
<213> ORGANISM: Artificial Sequence
<220> FEATURE:
<223> OTHER INFORMATION: HCDR3

<400> SEQUENCE: 6

Ala Arg Gly Phe Tyr Thr Met Asp Tyr
1               5

<210> SEQ ID NO 7
<211> LENGTH: 110
<212> TYPE: PRT
<213> ORGANISM: Artificial Sequence
<220> FEATURE:
<223> OTHER INFORMATION: VL domain

<400> SEQUENCE: 7

Arg Asp Ile Gln Met Thr Gln Ser Pro Ser Ser Leu Ser Ala Ser Leu
1               5                   10                  15

Gly Gly Lys Val Thr Ile Thr Cys Gln Ala Ser Gln Asp Ile Asn Lys
                20                  25                  30

Tyr Ile Ala Trp Tyr Gln Phe Lys Pro Gly Lys Gly Pro Arg Leu Leu
            35                  40                  45

Ile His Tyr Thr Ser Thr Leu Gln Pro Ala Ile Pro Ser Arg Phe Ser
        50                  55                  60

Gly Ser Gly Ser Gly Arg Glu Tyr Ser Phe Ser Ile Ser Asn Leu Glu
65                  70                  75                  80

Pro Glu Asp Ile Ala Thr Tyr Tyr Cys Leu His Tyr Asp Asn Leu Pro
                85                  90                  95

Trp Thr Phe Gly Gly Gly Thr Lys Leu Glu Ile Lys Arg Ala
            100                 105                 110
```

```
<210> SEQ ID NO 8
<211> LENGTH: 116
<212> TYPE: PRT
<213> ORGANISM: Artificial Sequence
<220> FEATURE:
<223> OTHER INFORMATION: VH domain

<400> SEQUENCE: 8

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Ala Phe Ser Thr Tyr
            20                  25                  30

Thr Met His Trp Val Lys Gln Arg Pro Arg Gln Gly Leu Glu Trp Ile
        35                  40                  45

Gly Tyr Ile Asn Pro Asn Ser Ala Ser Thr Ser Tyr Asn Glu Asn Phe
    50                  55                  60

Lys Asp Lys Ala Thr Leu Thr Ala Asp Lys Ser Ser Asn Thr Ala Tyr
65                  70                  75                  80

Met His Leu Ser Ser Leu Thr Ser Glu Asp Ser Ala Val Tyr Tyr Cys
                85                  90                  95

Ala Arg Gly Phe Tyr Thr Met Asp Tyr Trp Gly Gln Gly Thr Ser Val
            100                 105                 110

Thr Val Ser Ser
        115

<210> SEQ ID NO 9
<211> LENGTH: 246
<212> TYPE: PRT
<213> ORGANISM: Artificial Sequence
<220> FEATURE:
<223> OTHER INFORMATION: scFv derived from clone NA1/34.HLK

<400> SEQUENCE: 9

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Ala Phe Ser Thr Tyr
            20                  25                  30

Thr Met His Trp Val Lys Gln Arg Pro Arg Gln Gly Leu Glu Trp Ile
        35                  40                  45

Gly Tyr Ile Asn Pro Asn Ser Ala Ser Thr Ser Tyr Asn Glu Asn Phe
    50                  55                  60

Lys Asp Lys Ala Thr Leu Thr Ala Asp Lys Ser Ser Asn Thr Ala Tyr
65                  70                  75                  80

Met His Leu Ser Ser Leu Thr Ser Glu Asp Ser Ala Val Tyr Tyr Cys
                85                  90                  95

Ala Arg Gly Phe Tyr Thr Met Asp Tyr Trp Gly Gln Gly Thr Ser Val
            100                 105                 110

Thr Val Ser Ser Gly Gly Gly Gly Ser Gly Gly Gly Gly Ser Gly Gly
        115                 120                 125

Gly Gly Ser Gly Gly Gly Gly Ser Arg Asp Ile Gln Met Thr Gln Ser
        130                 135                 140

Pro Ser Ser Leu Ser Ala Ser Leu Gly Gly Lys Val Thr Ile Thr Cys
145                 150                 155                 160

Gln Ala Ser Gln Asp Ile Asn Lys Tyr Ile Ala Trp Tyr Gln Phe Lys
                165                 170                 175

Pro Gly Lys Gly Pro Arg Leu Leu Ile His Tyr Thr Ser Thr Leu Gln
            180                 185                 190
```

```
Pro Ala Ile Pro Ser Arg Phe Ser Gly Ser Gly Ser Gly Arg Glu Tyr
            195                 200                 205

Ser Phe Ser Ile Ser Asn Leu Glu Pro Glu Asp Ile Ala Thr Tyr Tyr
    210                 215                 220

Cys Leu His Tyr Asp Asn Leu Pro Trp Thr Phe Gly Gly Gly Thr Lys
225                 230                 235                 240

Leu Glu Ile Lys Arg Ala
                245

<210> SEQ ID NO 10
<211> LENGTH: 69
<212> TYPE: PRT
<213> ORGANISM: Artificial Sequence
<220> FEATURE:
<223> OTHER INFORMATION: Transmembrane domain derived from CD8

<400> SEQUENCE: 10

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65

<210> SEQ ID NO 11
<211> LENGTH: 113
<212> TYPE: PRT
<213> ORGANISM: Artificial Sequence
<220> FEATURE:
<223> OTHER INFORMATION: Intracellular signaling domain derived from
      CD3ζ

<400> SEQUENCE: 11

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 12
<211> LENGTH: 42
<212> TYPE: PRT
<213> ORGANISM: Artificial Sequence
<220> FEATURE:
<223> OTHER INFORMATION: Costimulatory signaling domain derived from
      CD137
```

```
<400> SEQUENCE: 12

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Gly Gly Cys Glu Leu
            35              40
```

CD1a ANTIBODY-EXPRESSING CAR T-CELLS FOR THE TREATMENT OF CD1a-POSITIVE CANCER

RELATED APPLICATIONS

This application is a 35 U.S.C. § 371 national stage filing of International Application No. PCT/EP2020/053769, filed on Feb. 13, 2020, which in turn claims the benefit of European Patent Application No. 19382104.8, filed on Feb. 14, 2019. The entire contents of each of the foregoing applications are incorporated herein by reference.

TECHNICAL FIELD

The present invention provides therapeutics for the treatment of CD1a-positive cancers such as T-cell acute lymphoblastic leukemia and T-cell lymphoblastic lymphoma. In particular, the present invention provides chimeric antigen receptor (CAR) T-cells that can target CD1a.

BACKGROUND ART

T-cell lineage acute lymphoblastic leukemia (T-ALL) is a malignant disorder resulting from leukemic transformation of thymic T-cell precursors[1]. T-ALL is phenotypically and genetically heterogeneous, and is commonly associated with genetic alterations/mutations in transcription factors involved in hematopoietic stem/progenitor cell (HSPC) homeostasis and in master regulators of T-cell development[2]. T-ALL comprises 10-15% and 20-25% of all acute leukemias diagnosed in children and adults, respectively[3,4] with a median diagnostic age of 9 years[5-7]. Intensive chemotherapy regimens have led to the improved survival of patients with T-ALL. However, the event-free (EFS) and overall (OS) survival remains <70%, and relapsed/refractory (R/R) T-ALL has a particularly poor outcome. There are currently no potential curative options beyond hematopoietic cell transplantation and conventional chemotherapy, which is linked to large trade-offs in toxicities[4,8], reinforcing the need for novel targeted therapies. T-cell lymphoblastic lymphomas (TCL) are etiologically and pathogenically different from T-ALL but phenotypically very similar. The main difference is that TCLs are found extramedullary while T-ALL is a bone marrow disease.

Immunotherapy has generated unprecedented expectations in cancer treatment and relies on the immune system as a powerful weapon against cancer. In recent years, adoptive cellular immunotherapy based on chimeric antigen receptors (CARs) has shown great potential. CAR therapy redirects genetically modified T-cells to specifically recognize and eliminate specific antigen-expressing tumor cells in a major histocompatibility complex-independent fashion[9,10]. The success of CAR T-cells (CARTs) redirected against CD19 or CD22 is now indisputable for B-cell malignancies (mainly B-ALL)[11-14]. But, strategies targeting T-cell malignancies using CARTs remain challenging because of the shared expression of target antigens between CARTs and T-lineage tumoral cells. In this regard, CARTs against pan T-cell antigens have two major drawbacks: i) CARTs self-targeting/fratricide and, ii) T-cell aplasia, leading to life-threating immunodeficiency[15-17].

Recent elegant studies demonstrated that T-cells transduced with either CD7, CD3, CD5 or TCR CARS, the most expressed pan-T-cell antigens, efficiently eliminate T-ALL blasts in vitro and are able to editing or protein expression blockers, were required for disruption of the target antigen in T-cells prior to CAR transduction, to avoid extensive self-antigen driven fratricide[15-17,19].

Thus, there remains a need for a therapy that can successfully treat T-ALL. The present invention aims to provide a therapy for treating CD1a-positive T-ALL.

FIGURES

FIG. 1. CD1a expression in T-ALL and normal hematopoiesis and thymopoiesis. (A) Immunophenotype of de novo T-ALL samples (n=38) for the indicated markers. Upper and intermediate curly brackets identify $CD1a^{+/++}$ and $CD1a^{low/+}$ coT-ALL patients, respectively. Black circles at bottom depict non-coTALL patients. (B) Representative FACS dot plot of a coT-ALL patient. CD7+CD1a+ cells are coT-ALL blasts and CD3+CD7+CD1a− (either CD4+ or CD8+) are normal mature T-cell present in the diagnostic sample. (C) CD1a is retained at relapse (n=5 diagnostic-relapse coT-ALL pairs). Data shown as CD1a expression in relapse samples relative to the diagnostic-matched samples (diagnostic shown as 100% expression). (D) T-cells and CD34+ HSPCs do not express CD1a across ontogeny. (E) Scheme depicting the phenotype of developing thymic T-cell populations. (F) Representative FACS for pre-cortical ($CD34^{high}CD7$++CD1a−) and cortical (CD34+CD7++CD1a+) thymocytes. DX: diagnostic. RX: relapse.

Figure 2:
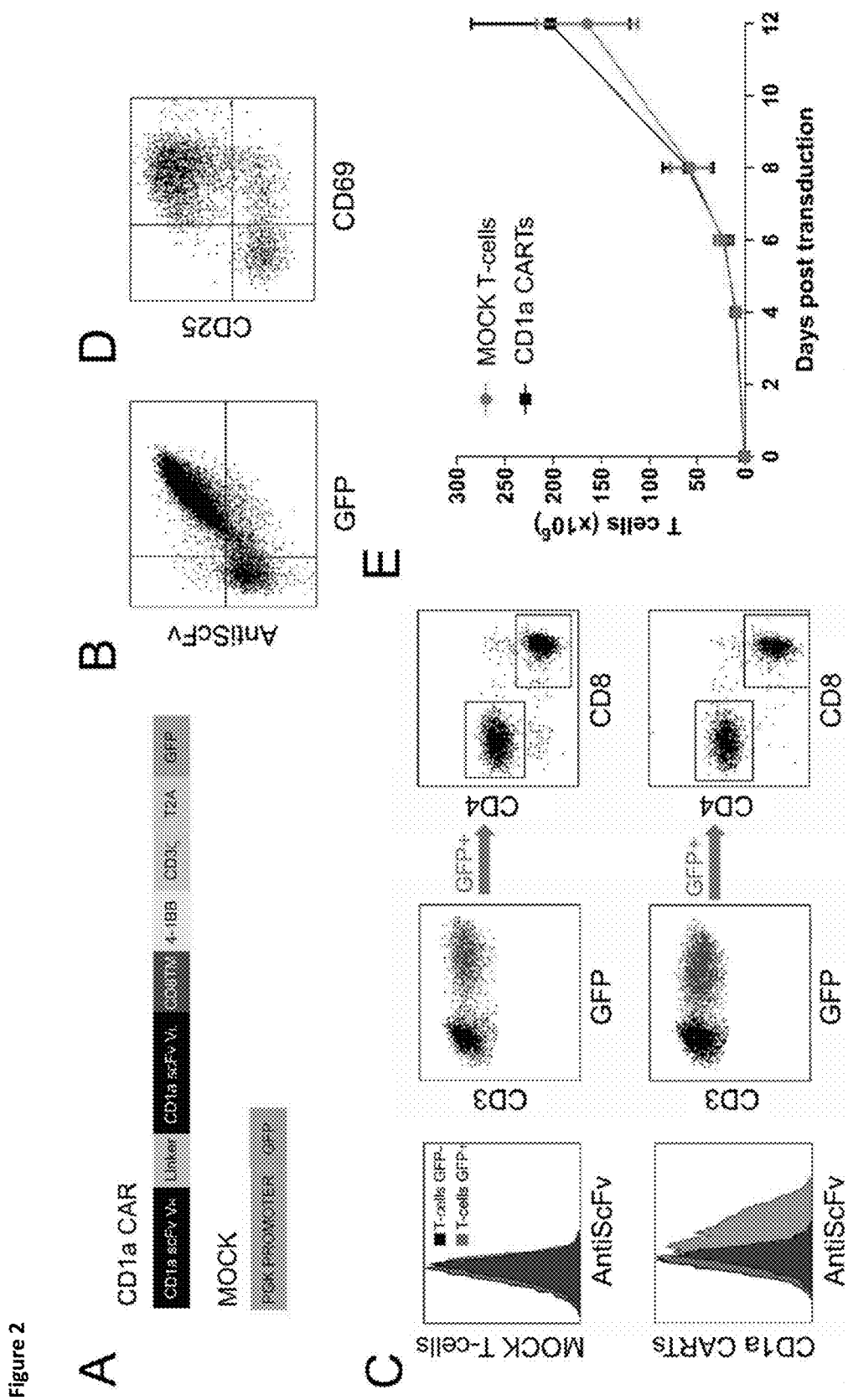
Figure 2:
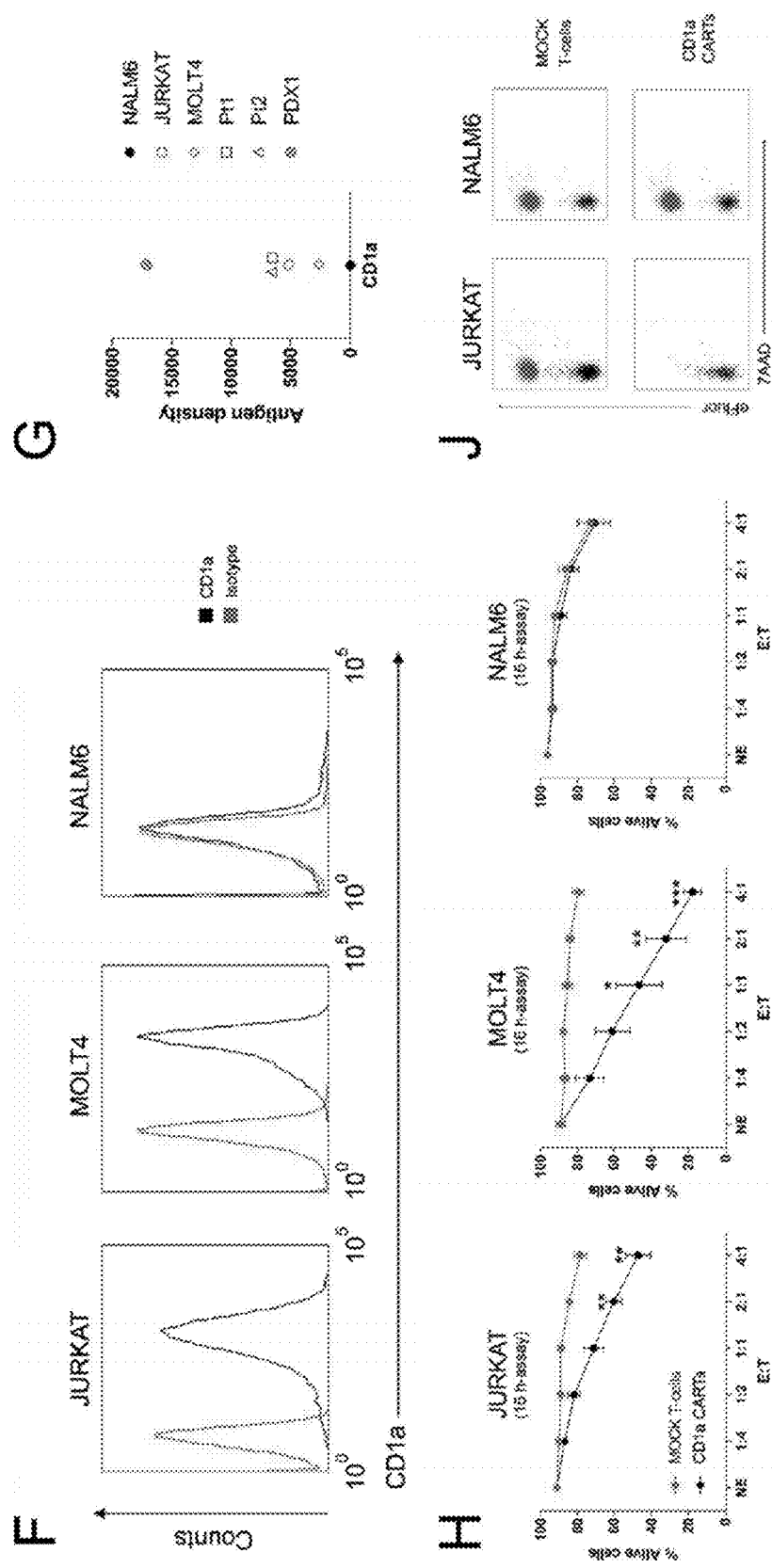
Figure 2:
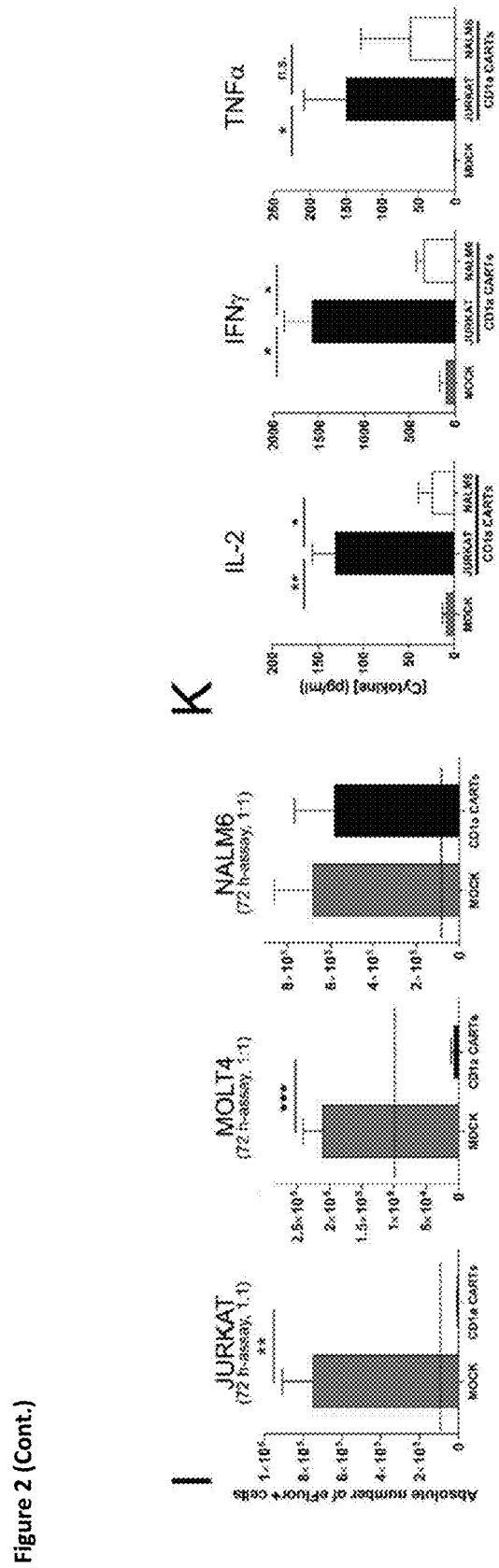

FIG. 2. CD1a CARTs specifically target and eliminate CD1a+ T-ALL cell lines in vitro. (A) Scheme of the CD1aCAR construct used. (B) CAR detection in 293T cells using an anti-scFv MoAb and GFP. (C) Representative CAR transduction and detection in CD4+ and CD8+ T-cells (n=6). (D) Proper T-cell activation (n=3). (E) Robust expansion of activated T-cells transduced with either mock or CD1a CAR reveals no signs of fratricide (n=4). (F) Surface expression of CD1a (black line) in Jurkat, MOLT4 and NALM6 cell lines. (G) CD1a antigen density in cell lines, primary coT-ALL samples and primografts. (H) Cytotoxicity of CD1a CARTs and MOCK T-cells against coT-ALL and B-ALL cell lines at the indicated E:T ratios in 16 h assays (n=4). (I) Absolute counts of alive eFluor+ target cells measured by FACS in 72 h cytotoxicity assays at 1:1 E:T ratio. (J) Representative FACS analysis of cytotoxicity with target cells labeled with eFluor670. (K) ELISA showing high-level production of the inflammatory cytokines IL-2, TNFα and IFNγ by CD1a CARTs exposed to Jurkat and NALM6 (negative control) cells in 16 h assays at 1:1 E:T ratio (n=4). *p<0.05, p<0.01, *p<0.001.

Figure 3:
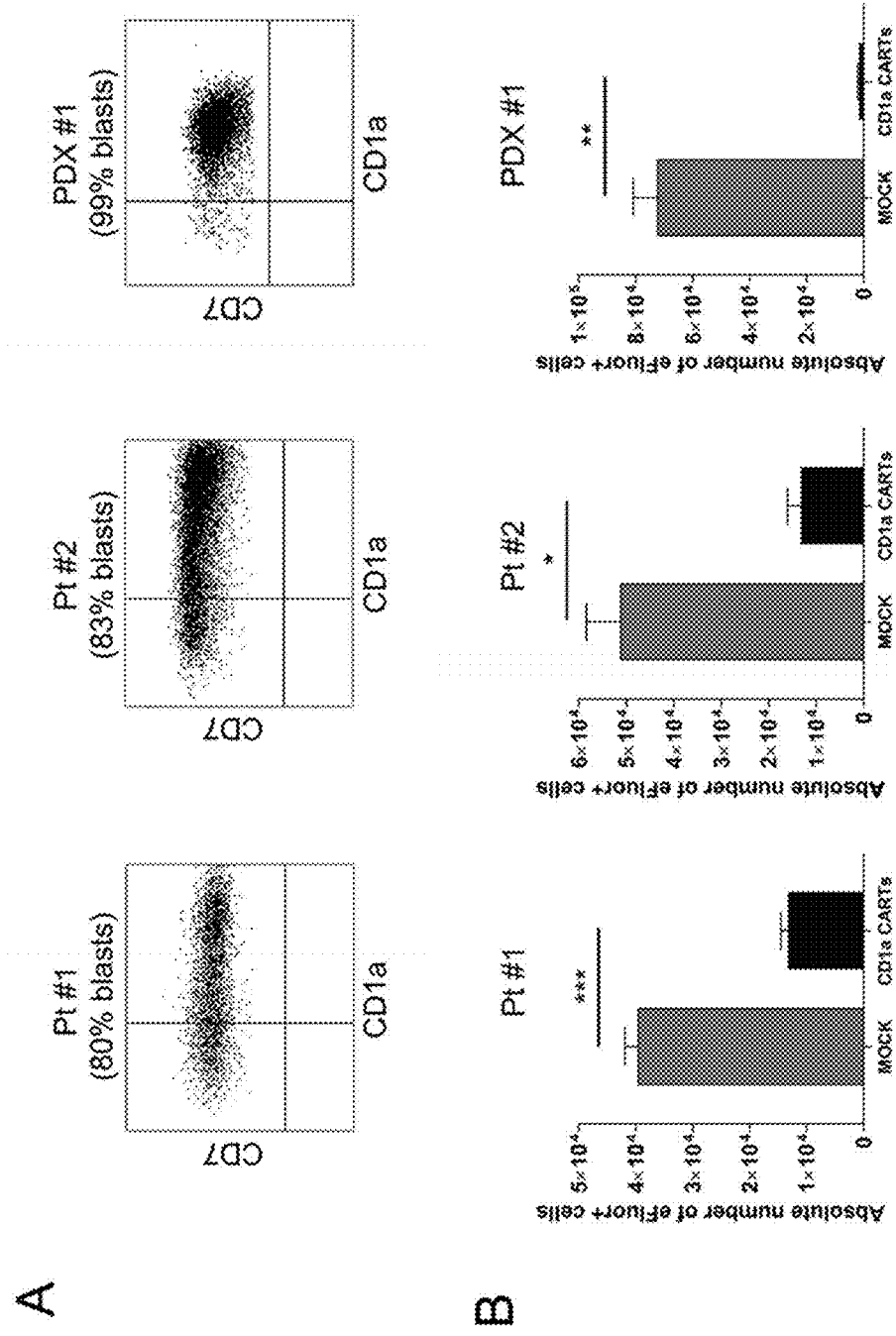
Figure 3:
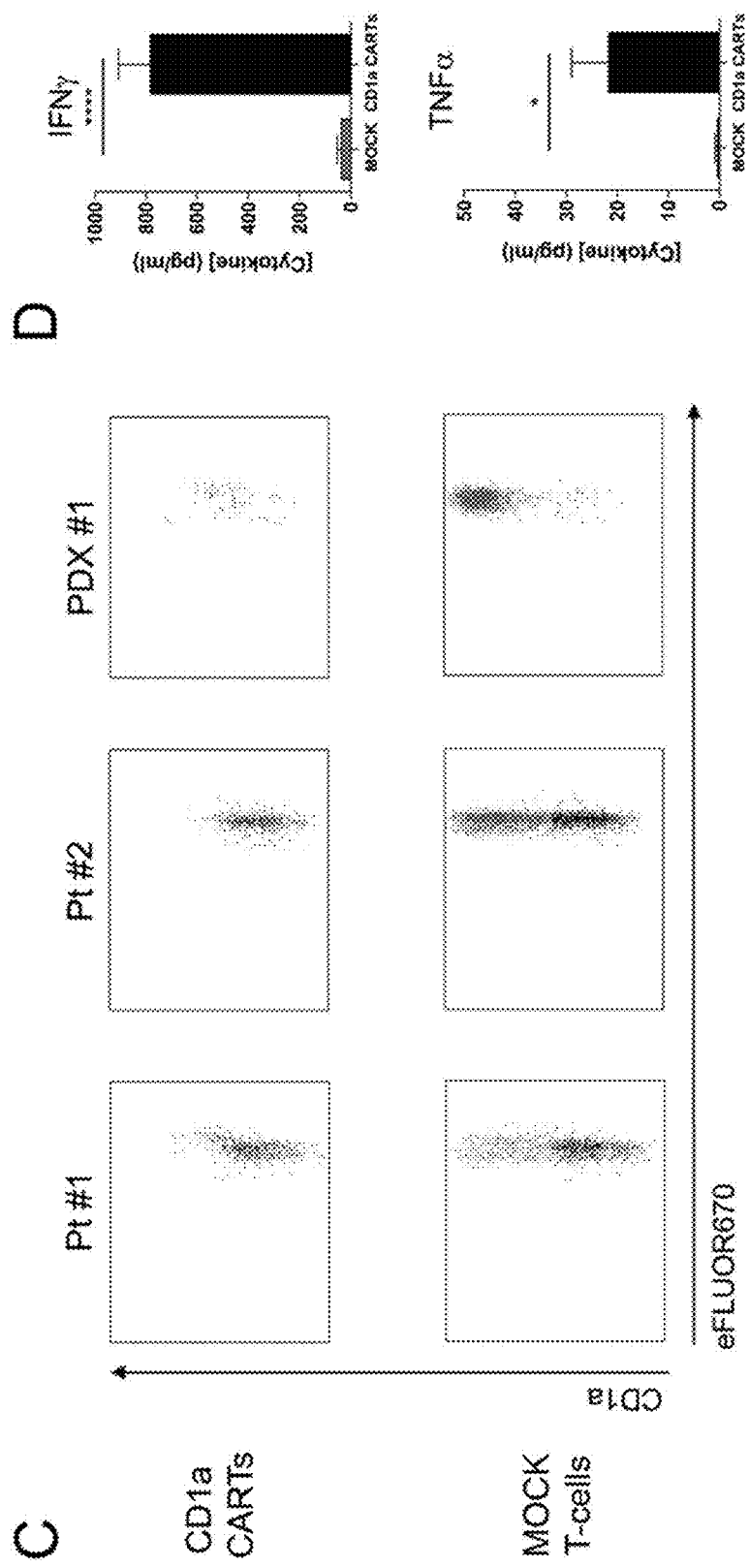

FIG. 3. CD1a CARTs specifically target and eliminate in vitro CD1a+ T-ALL blasts from primary samples or PDX models. (A) Expression of CD1a vs CD7 in coT-ALL blasts from primary patients/primografts. The % of CD1a+ blasts is indicated. (B) Cytotoxicity (in absolute counts of eFluor+ cells) measured by FACS in 48 h cytotoxicity assays at 4:1 E:T ratio (n=3). (C) Representative FACS analysis of CD1a within the eFluor-labeled target cells at the end of the cytotoxicity assay, revealing specificity of CD1a CARTs (n=3). (D) High-level production of pro-inflammatory cytokines by CD1a CARTs analyzed by ELISA (n=3 independent supernatants) in 16 h assays at 4:1 E:T ratio. *p<0.05, p<0.01, *p<0.001, ****p<0.0001.

Figure 4:
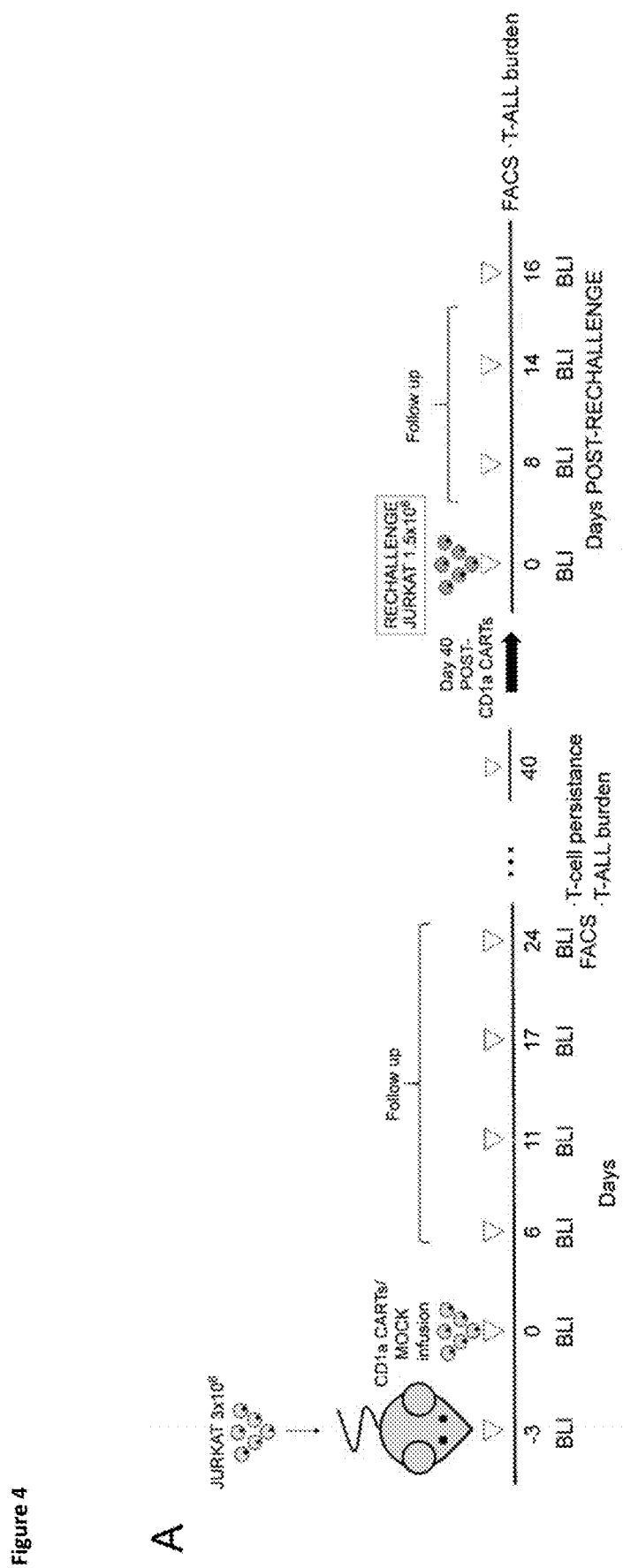
Figure 4:
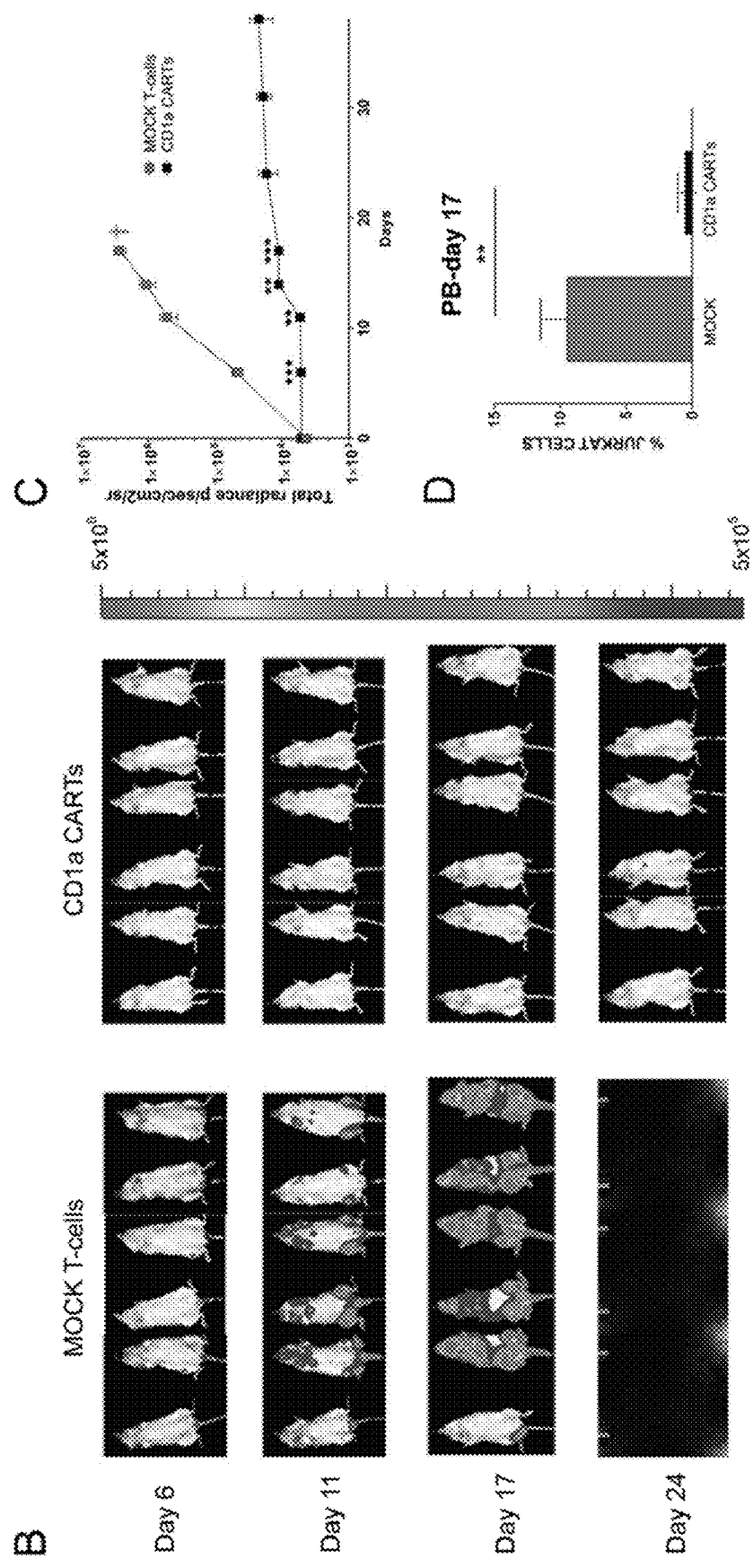
Figure 4:
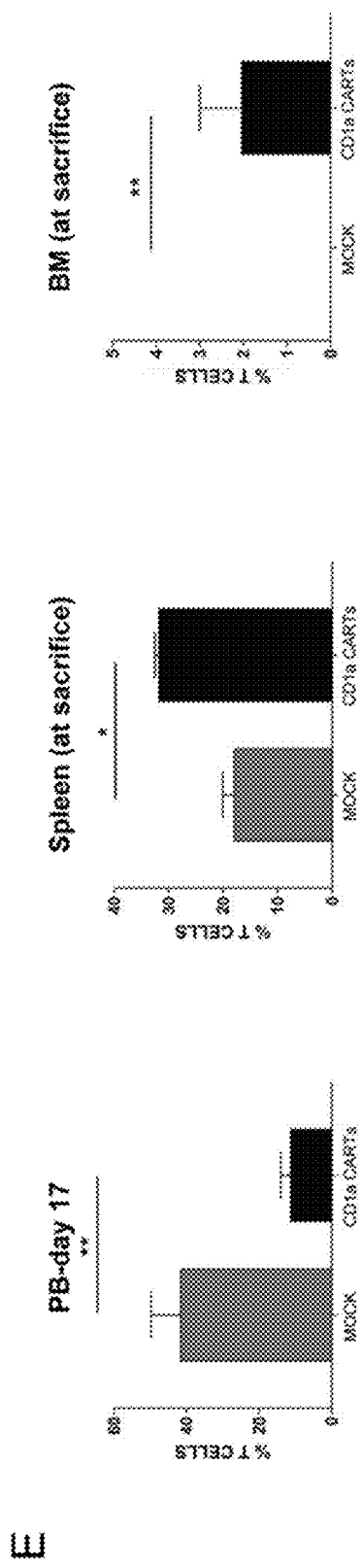

FIG. 4. CD1a CARTs fully control the progression of coT-ALL cells in a mouse xenograft setting. (A) Scheme of the xenograft model. NSG mice (n=6/group) were i.v. injected with $3\times10^6$ Luc-GFP-expressing Jurkat cells followed 3 days after by a single i.v. injection of $5\times10^6$ mock or CD1a CARTs. Tumor burden was monitored every 4-6 days by bioluminescence (BLI) using IVIS imaging. When MOCK-treated animals were fully leukemic, one-half of the CD1a CARTs-treated animals were sacrificed and analyzed by FACS (BM, PB and spleen) for leukemic burden and CARTs persistence. The remaining animals were re-challenged 6 weeks after with $1.5 \times 10^6$ Luc-Jurkat and were followed-up as before. (B) IVIS imaging of tumor burden monitored by BLI at the indicated timepoints. (C) Total radiance quantification (p/sec/cm$^2$/sr) at the indicated timepoints. †: sacrifice. (D) Circulating Jurkat cells in PB 17 days after CARTs infusion. (E) T-cell persistence in PB at day 17, and spleen and BM at sacrifice. Data is shown as mean±SD (n=6 mice/group). *p<0.05, p<0.01, *p<0.001.

Figure 5:
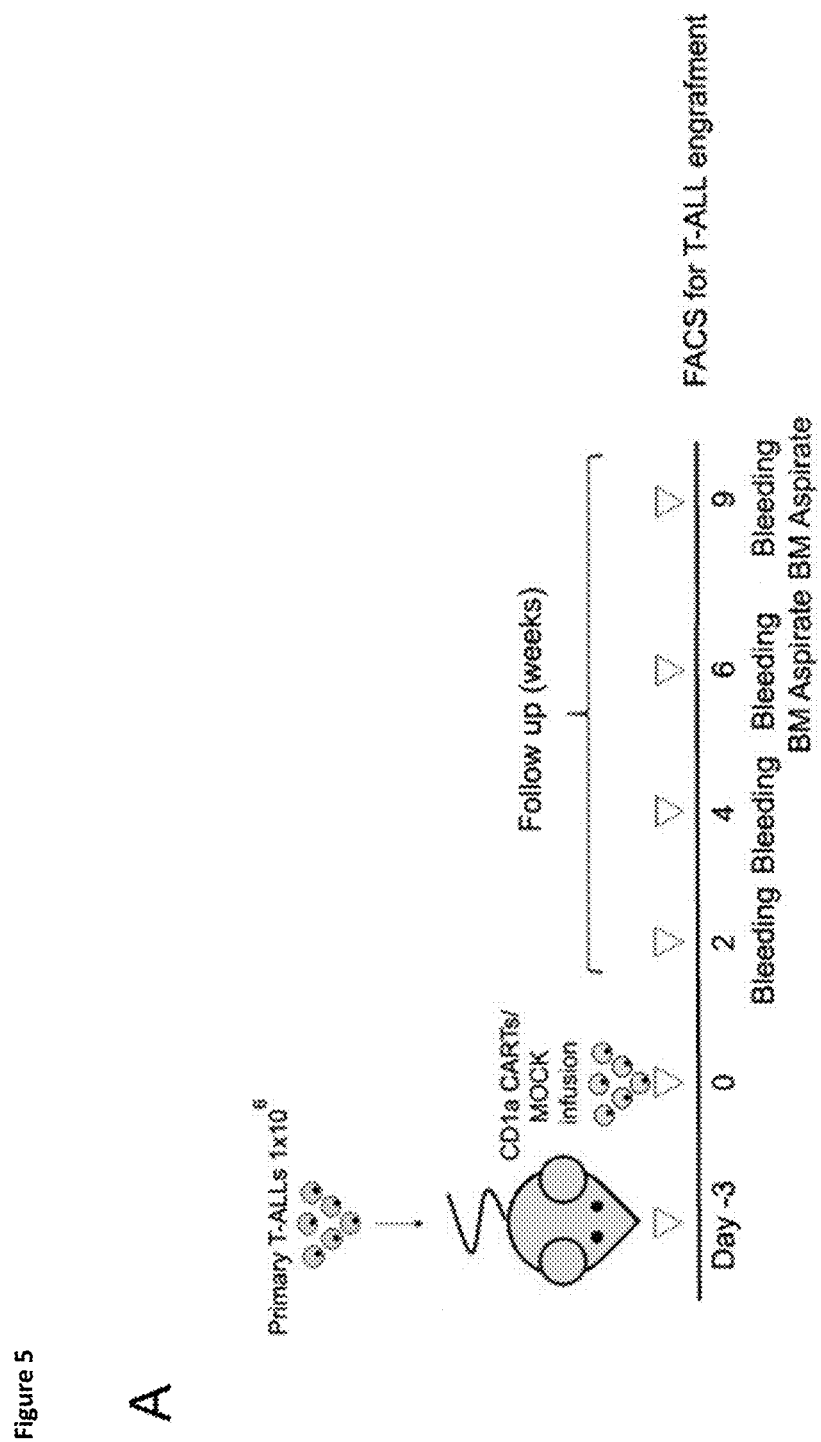
Figure 5:
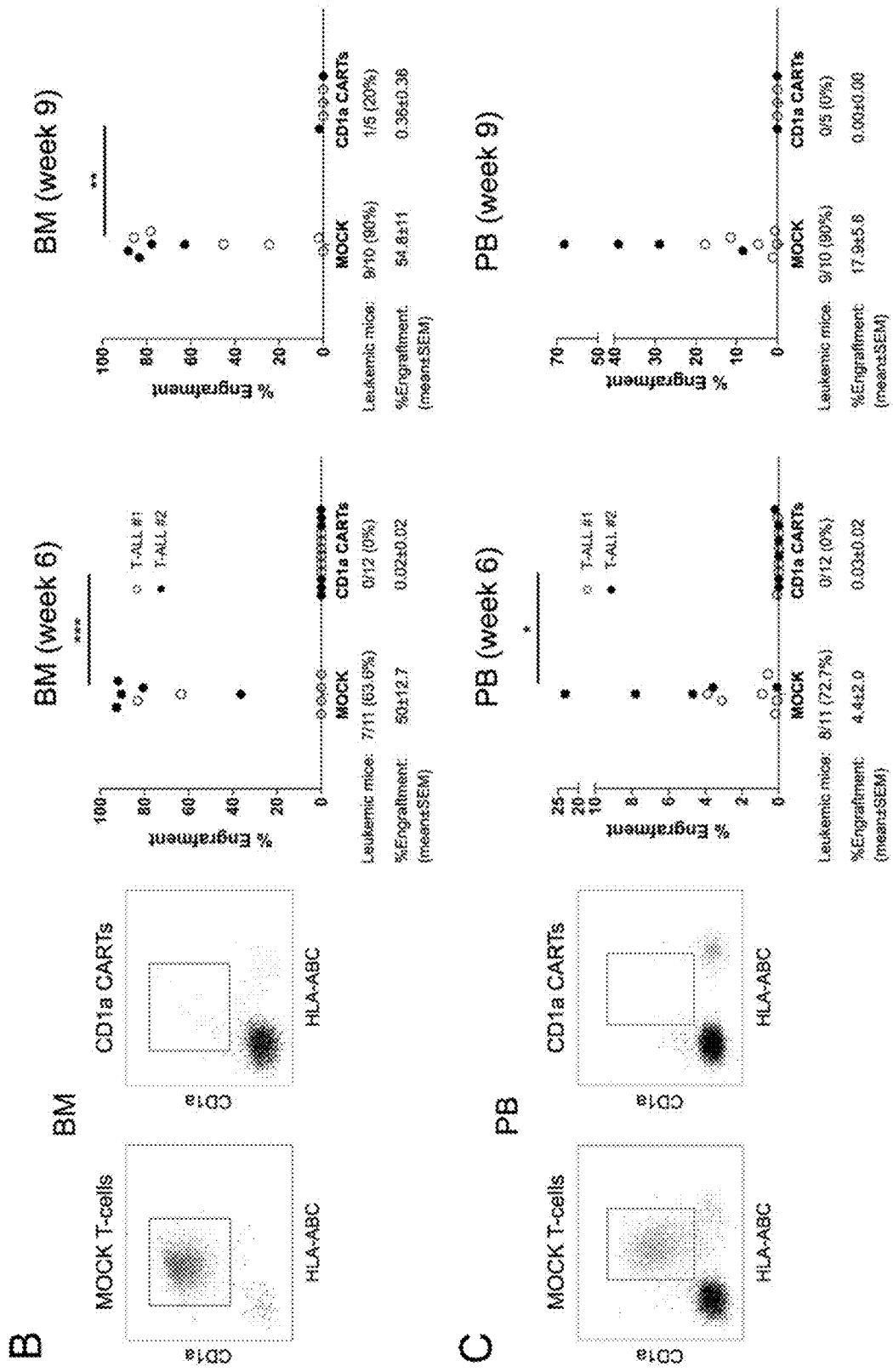
Figure 5:
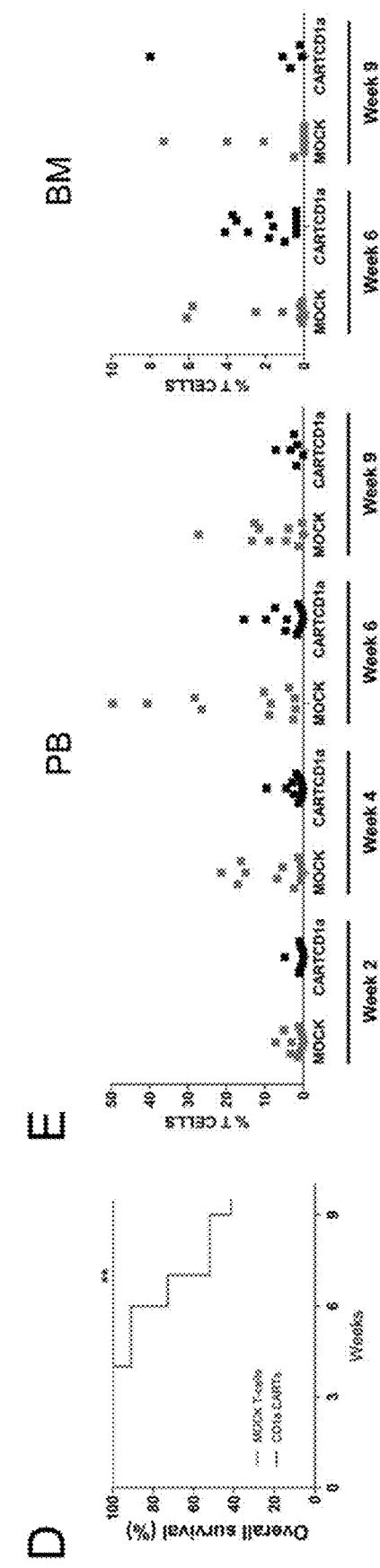

FIG. 5. CD1a CARTs fully abolish the progression of primary CD1a+ coT-ALL blasts in a PDX setting. (A) Scheme of the PDX model. NSG mice (n=5-6/group) were i.v. injected with $1 \times 10^6$ primary coT-ALL cells followed three days after by a single i.v. injection of $1 \times 10^6$ mock or CD1a CARTs. Tumor burden was monitored by FACS every other week by bleeding and BM aspirate after 6 and 9 weeks. (B,C) Frequency of leukemic mice and levels of leukemia in BM (B) and PB (C) 6 and 9 weeks after infusion of CARTs. The left panels show representative FACS plots. Primary CD1a+ T-ALL blasts are shown inside the box (grey). Effector T-cells are shown outside the box in grey. Mouse cells are shown in black. (D) 9-week OS of coT-ALL primografts receiving either CD1a CARTs or MOCK T-cells. (E) Effector T-cell persistence overtime in PB (week 2 towards week 9) and BM (week 6 and 9). Each dot represents an independent mouse. **p<0.01, Malcolm-Cox test.

Figure 6:
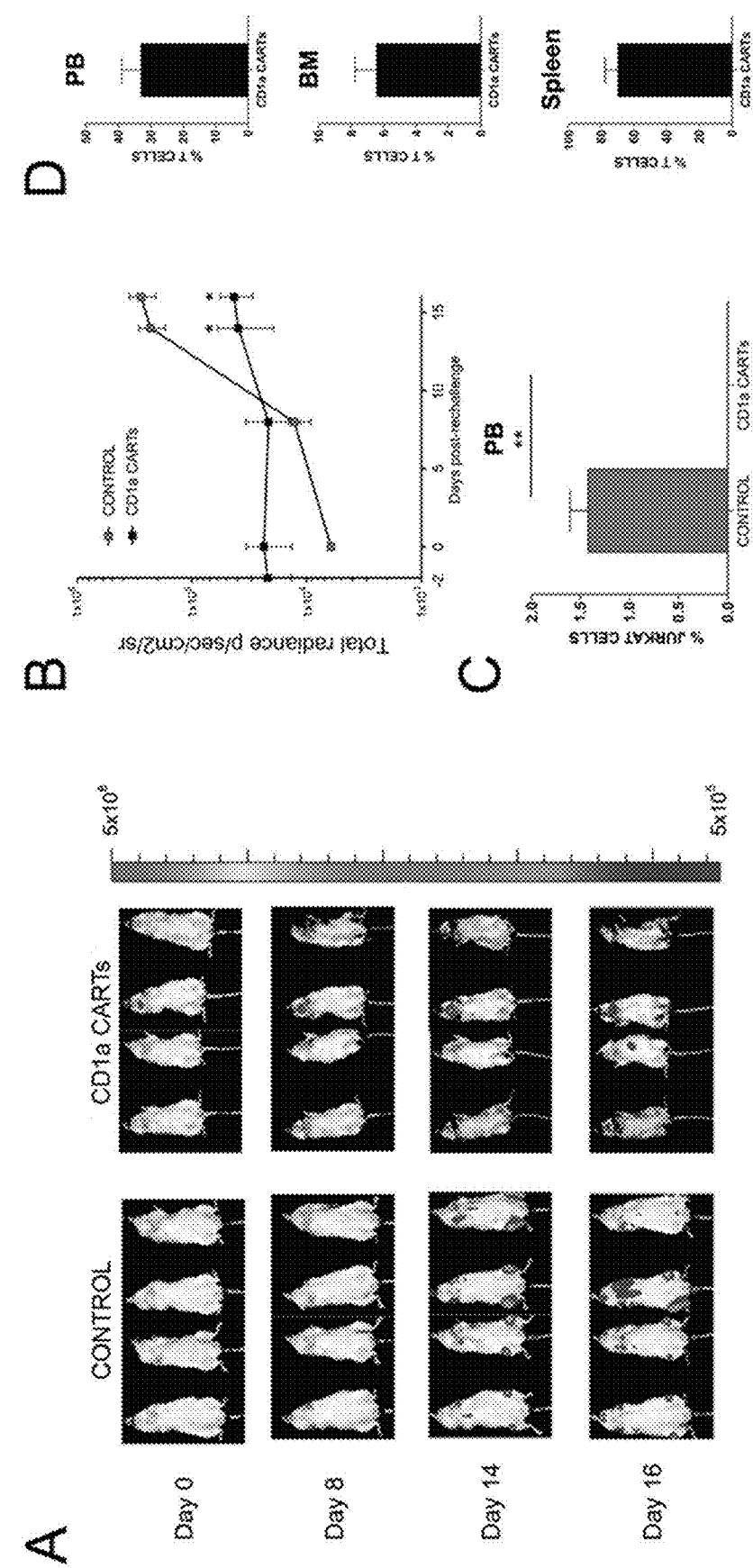
Figure 6:
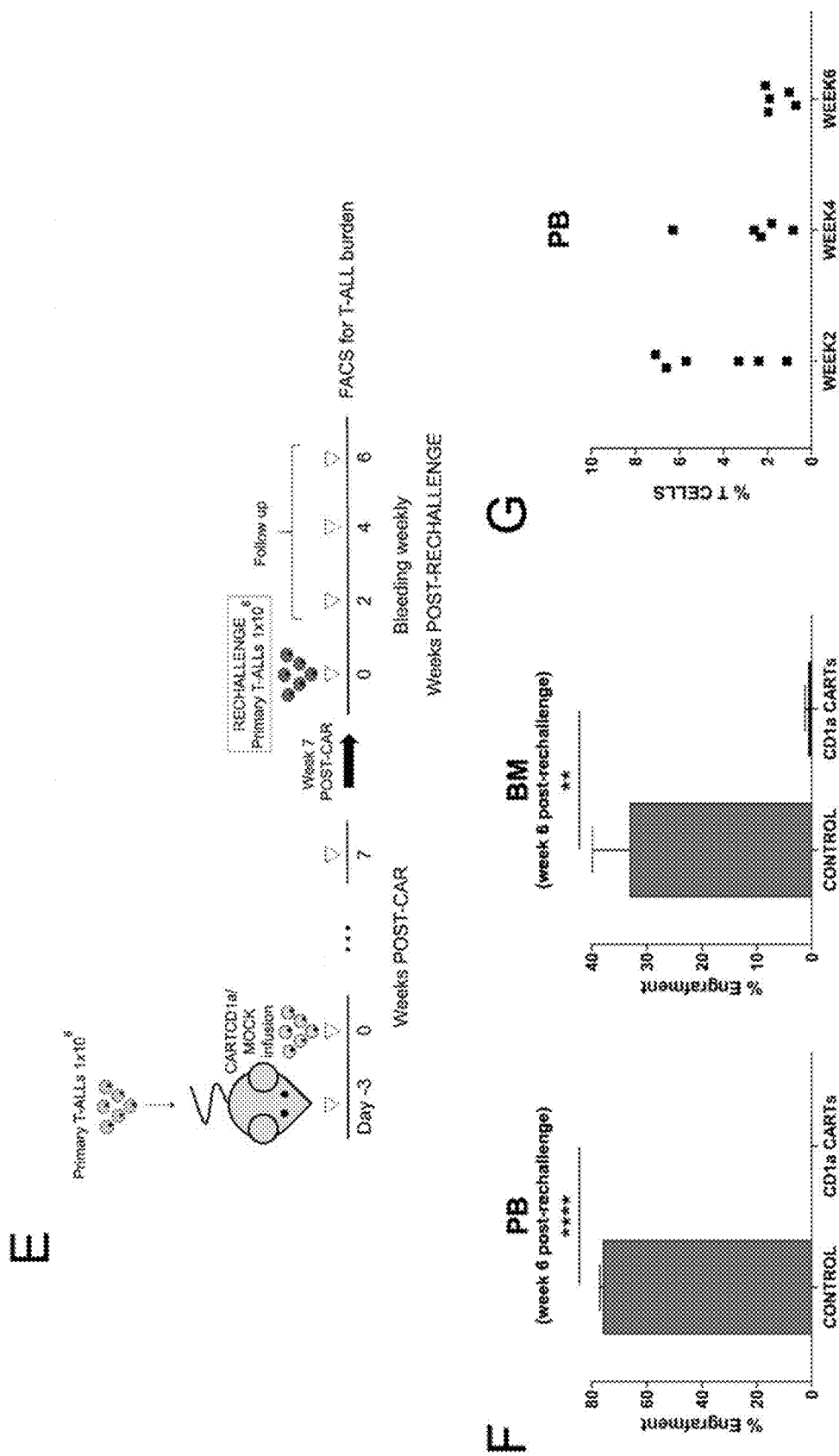

FIG. 6. CD1a CARTs retain the ability to control progression of CD1a+ cell lines and coT-ALL primary samples in a re-challenge PDX setting. (A) IVIS imaging of Jurkat cells burden in the re-challenged mice. (B) Total radiance quantification (p/sec/cm$^2$/sr) overtime in the mice re-challenged with Jurkat cells. (C) Circulating Jurkat cells in PB 16 days after re-challenge. (D) Robust effector T-cell persistence in PB, BM and spleen at sacrifice of the re-challenged animals. (E) Scheme of the re-challenge PDX experiments using coT-ALL primary samples. CARTs-bearing PDX mice were re-challenged with $1 \times 10^6$ primary CD1a+ T-ALL seven weeks after initial CARTs infusion. (F) Secondary coT-ALL burden in engrafted PB (left panel) and BM (right panel) 6 weeks after leukemia re-challenge. (G) Effector T-cell persistence overtime in PB (week 2, 4 and 6) from PDXs re-challenged with coT-ALL primary samples. Each dot represents an independent mouse. *p<0.05, p<0.01, *p<0.001, ****<0.0001.

Figure 7:
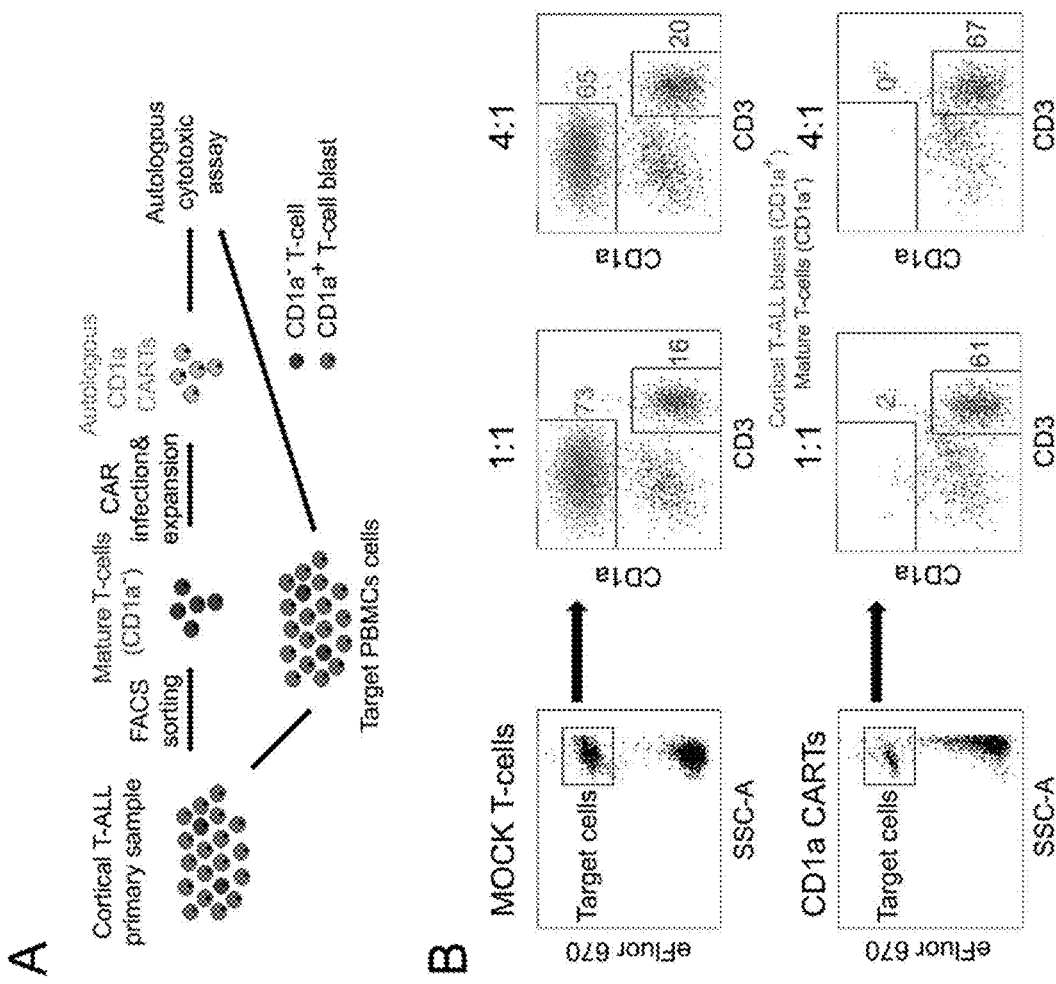
Figure 7:
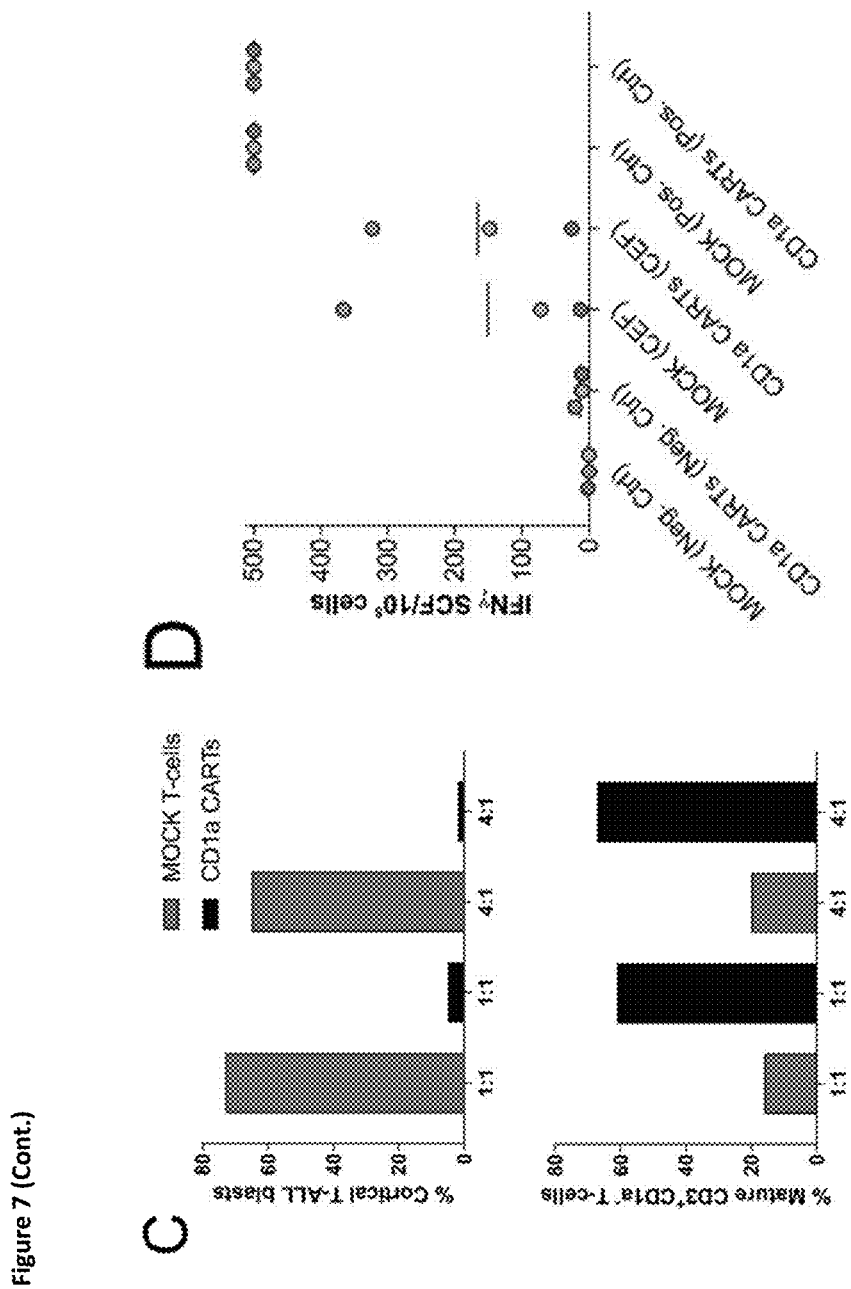

FIG. 7. CD1a CARTs derived from coT-ALL patients at presentation specifically lyse autologous CD1a+ T-ALL blasts. (A) Scheme depicting the experimental design for the autologous cytotoxic assay. Mature (normal) CD3+CD1a$^-$ T-cells were FACS-purified from the PB of a coT-ALL patient, infected with CD1a CAR, expanded, and exposed to autologous total PBMCs. (B) FACS analysis of autologous cytotoxic 48 h-assay at 1:1 and 4:1 E:T. eFluor670-labeled total PBMC target population contains CD1a+ T-ALL blasts (upper box) and mature CD3+CD1a– T-cells (bottom box). (C) Quantification of CD1a CARTs-mediated specific lysis for coT-ALL blasts (upper panel) and CD3+CD1a– mature T-cells (bottom panel). (D) ELISpot showing the number of IFNγ SFC from mock versus CD1a CARTs stimulated with a pool of peptides from CMV, EBV and Flu (CEF). Staphylococcal enterotoxin B (SEB) was used as positive control.

Figure 8:
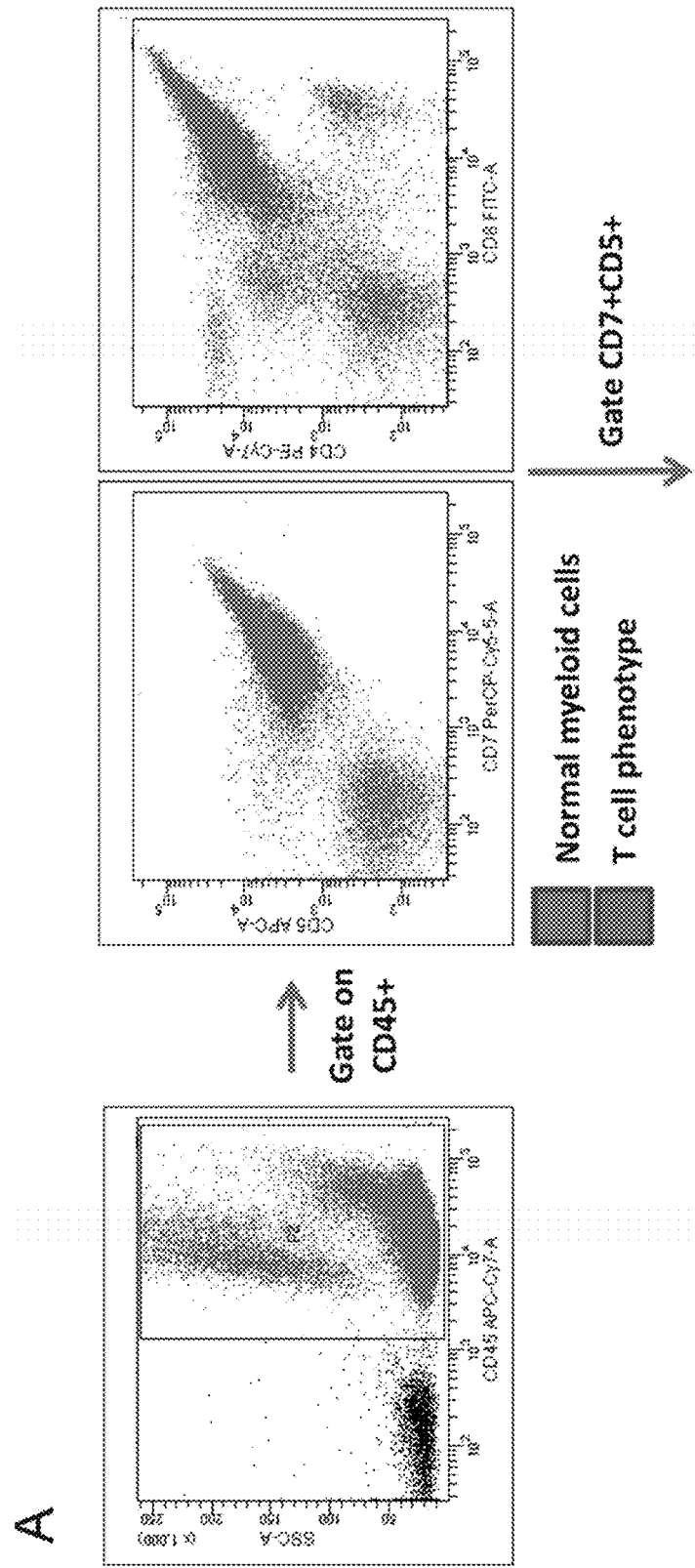
Figure 8:
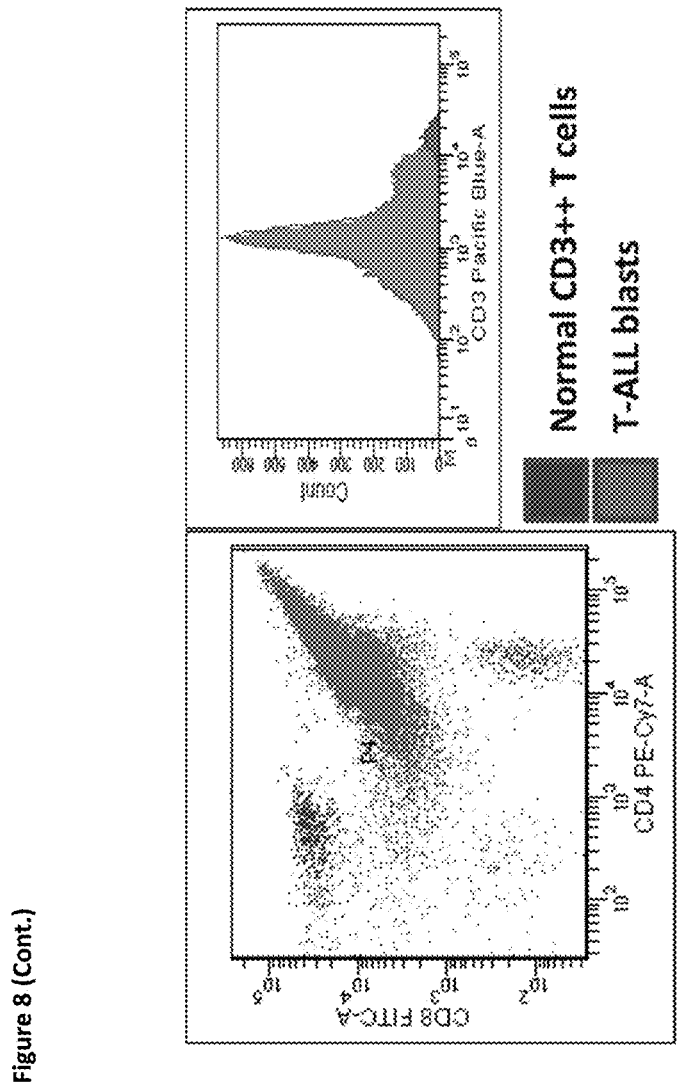
Figure 8:
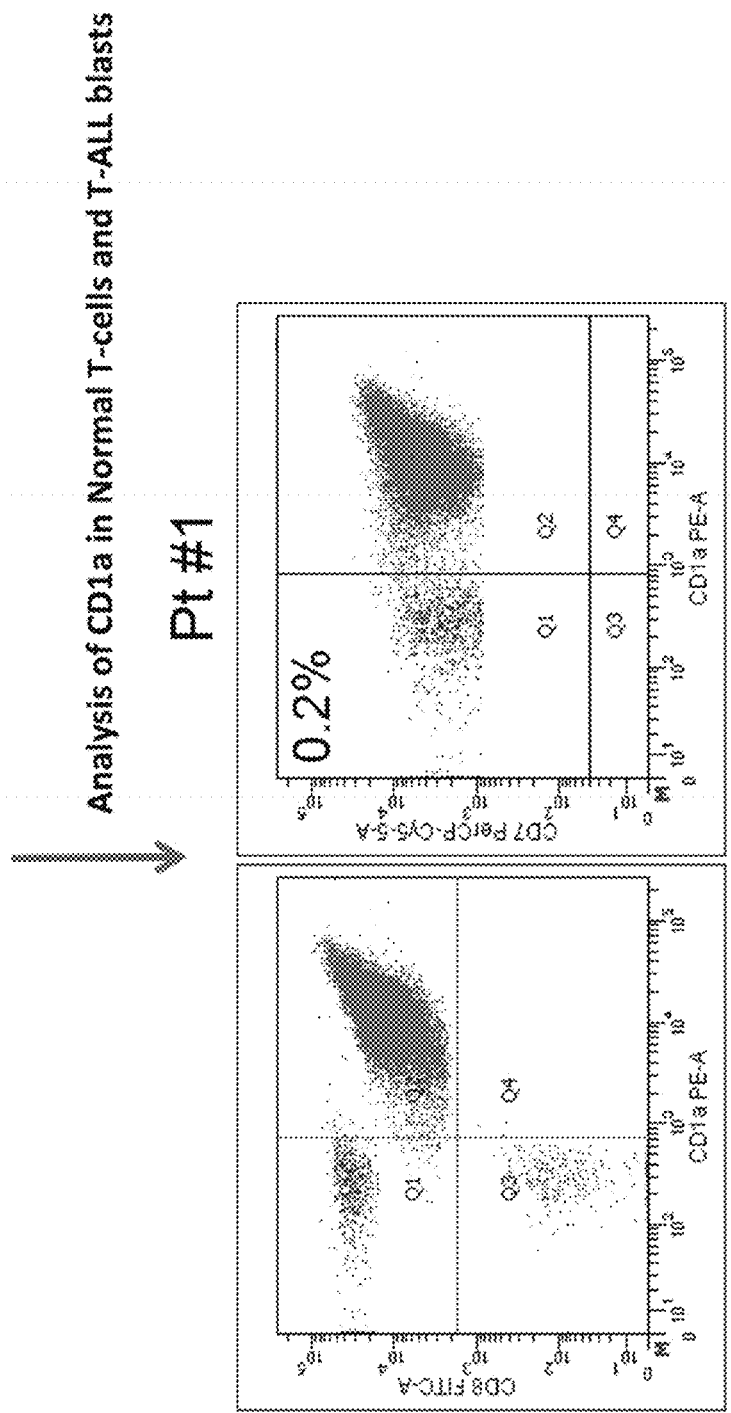
Figure 8:
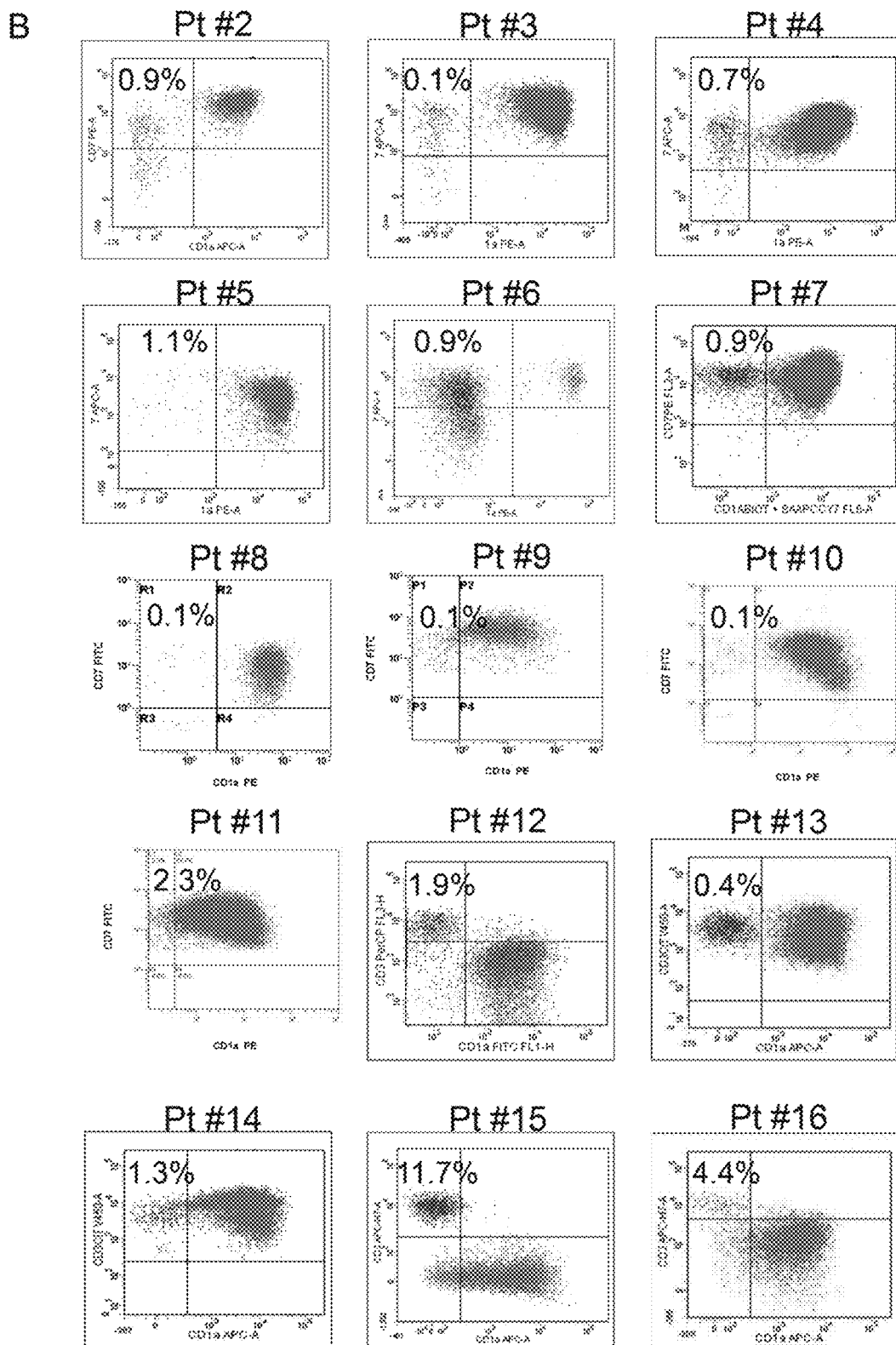

FIG. 8. Immunophenotype for each individual CD1a++ coT-ALL patient presented in this study. (A) Gating strategy distinguishing mature normal T-cells (CD3++CD1a– either CD4+ or CD8+) and coT-ALLs blasts (CD7+CD1a+). Note that coT-ALL blasts commonly have aberrant expression for CD3 and/or CD4/CD8). (B) CD7/CD3 vs CD1a FACS dot plots for n=16 available CD1a++ coT-ALL patients showing the percentage of mature normal T-cells (left quadrant) and coT-ALLs blasts (right quadrant).

Figure 9:
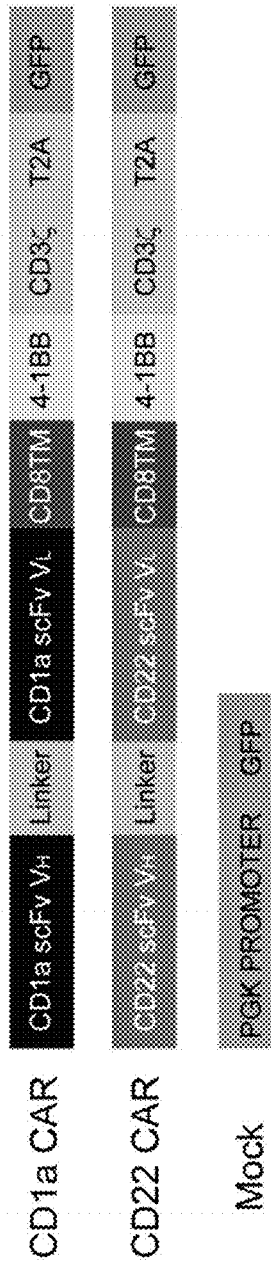
Figure 9:
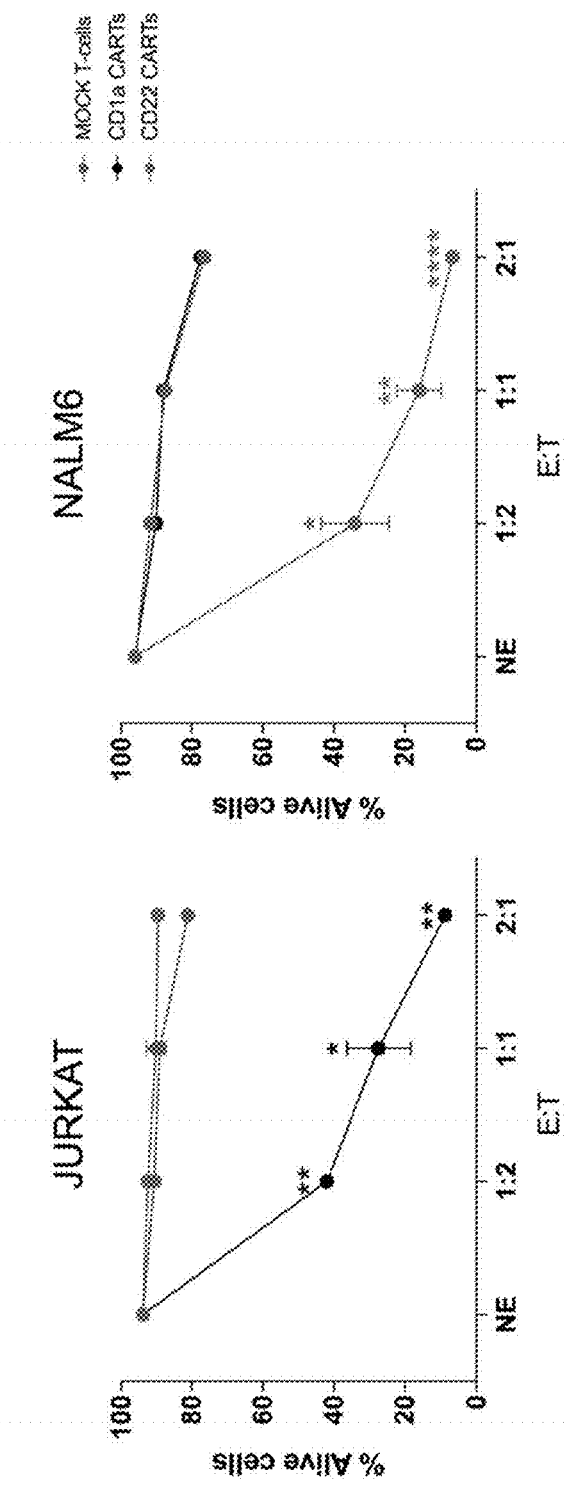

FIG. 9. In vitro specificity of CD1a CARTs. (A) Scheme of the CD1aCAR, CD22CAR and MOCK constructs used in the present study. (B) CD1a CARTs but not CD22 CARTs lyse the T-ALL cell line Jurkat. CD22 CARTs but not CD1a CARTs lyse the B-ALL line NALM6. *p<0.05, p<0.01, *p<0.001, ****p<0.0001.

Figure 10:
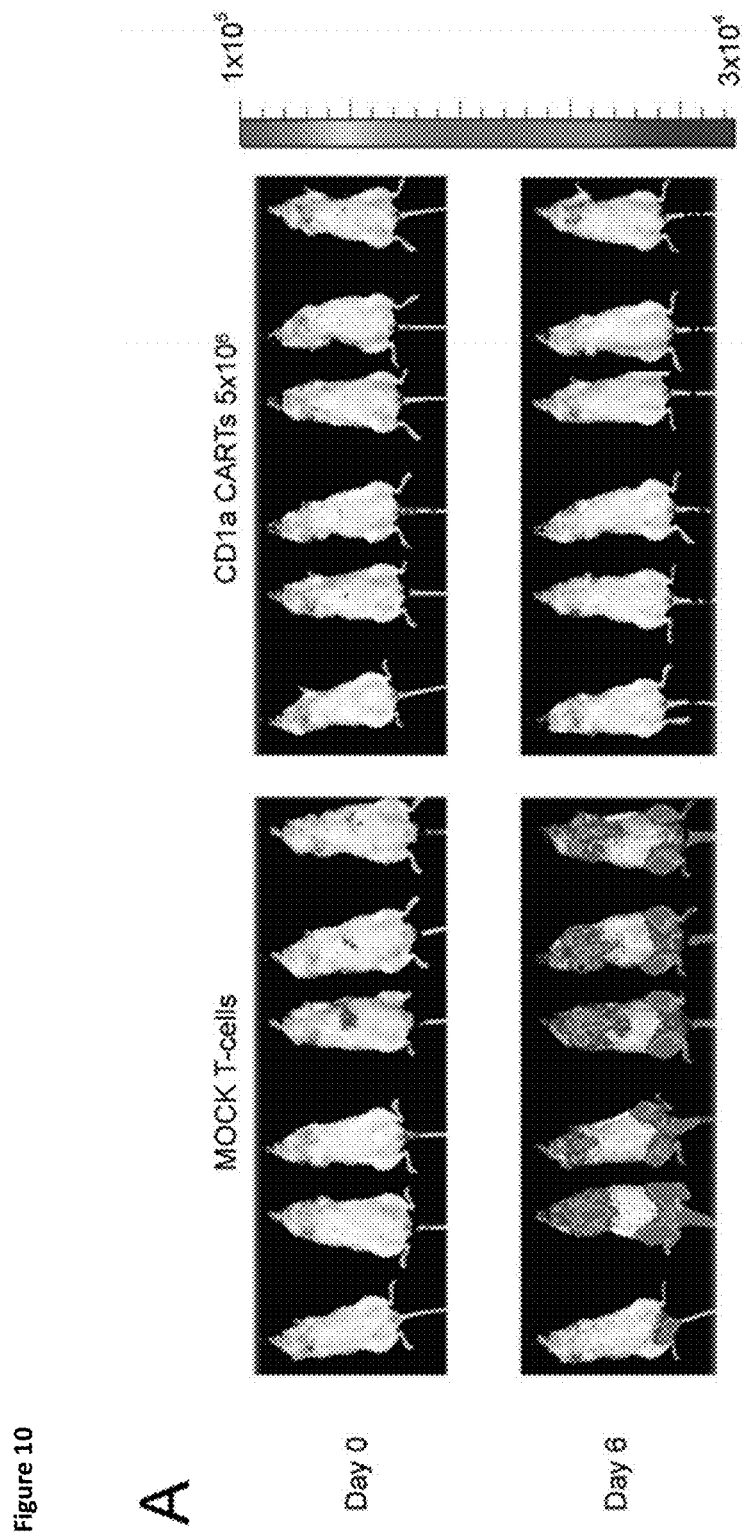
Figure 10:
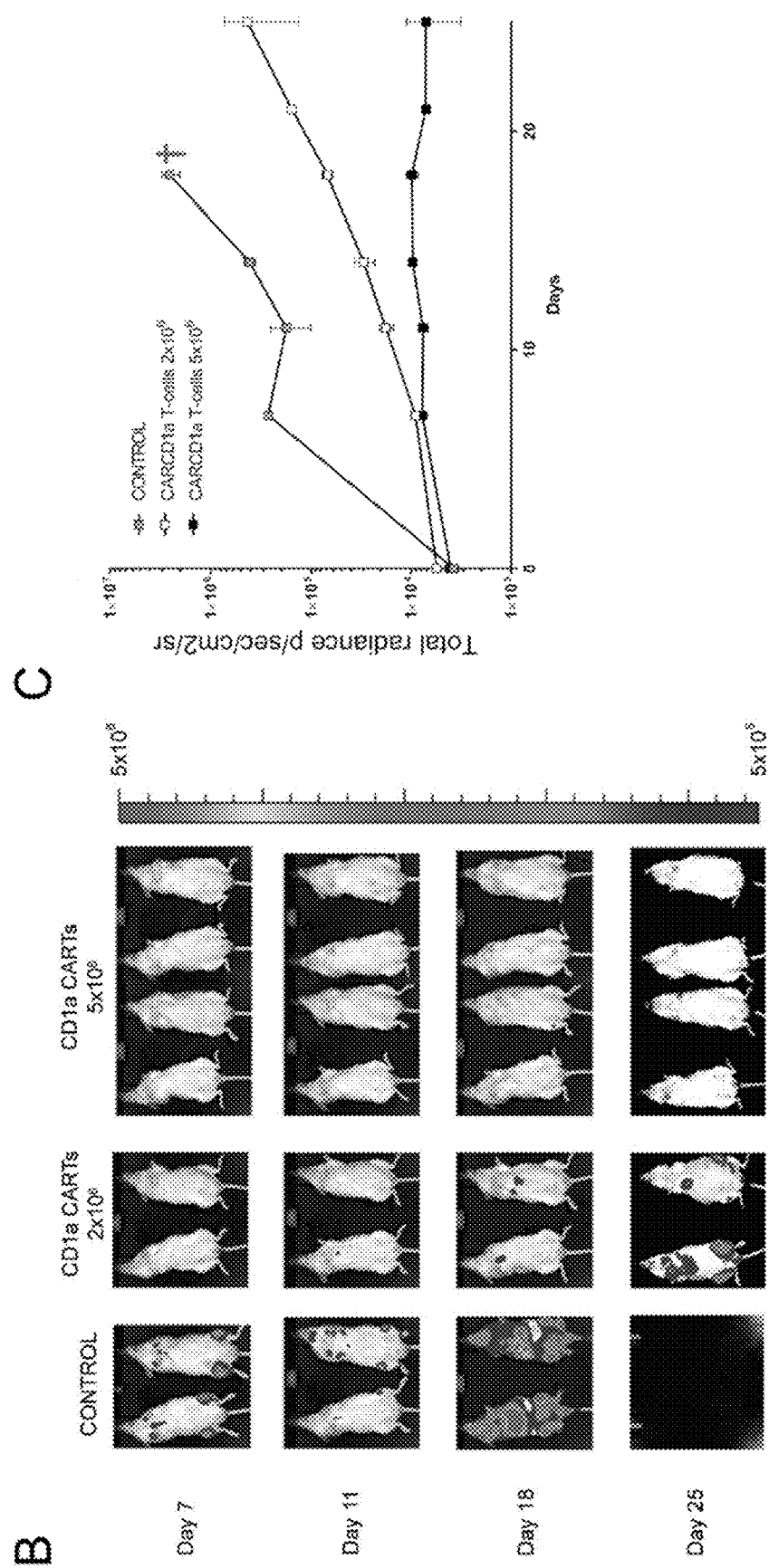

FIG. 10. In vivo cytotoxicity of CD1a CARTs is dose-dependent. (A) Tumor burden monitored by BLI at the beginning of the experiment (scale: $3 \times 10^4$ to $1 \times 10^5$ p/sec/cm$^2$/sr) confirming early and efficient T-ALL engraftment. (B) IVIS imaging of tumor burden monitored by BLI at the indicated time points for CARTs doses of $2 \times 10^6$ and $5 \times 10^6$ p/sec/cm$^2$/sr. (C) Total radiance quantification (p/sec/cm$^2$/sr) at the indicated time points for CARTs doses of $2 \times 10^6$ and $5 \times 10^6$. N=3-4 mice/group. †: sacrifice. *p<0.05, p<0.01, *p<0.001, ****p<0.0001.

Figure 11:
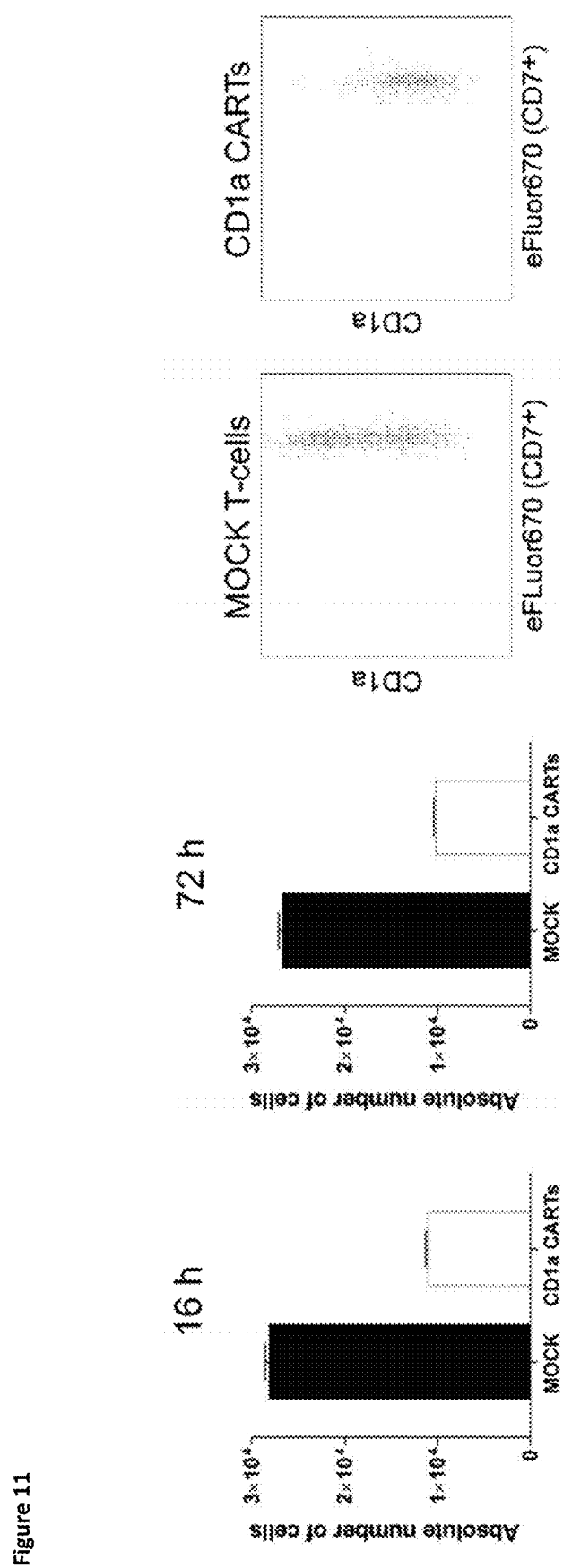

FIG. 11. CD1a CARTs do not target CD7+CD1a– thymocytes. Cytotoxicity assays against fetal thymic cells were performed at 16 h and 72 h at 4:1 E:T for CD1a CARTs and MOCK T-cells (n=2).

Figure 12:
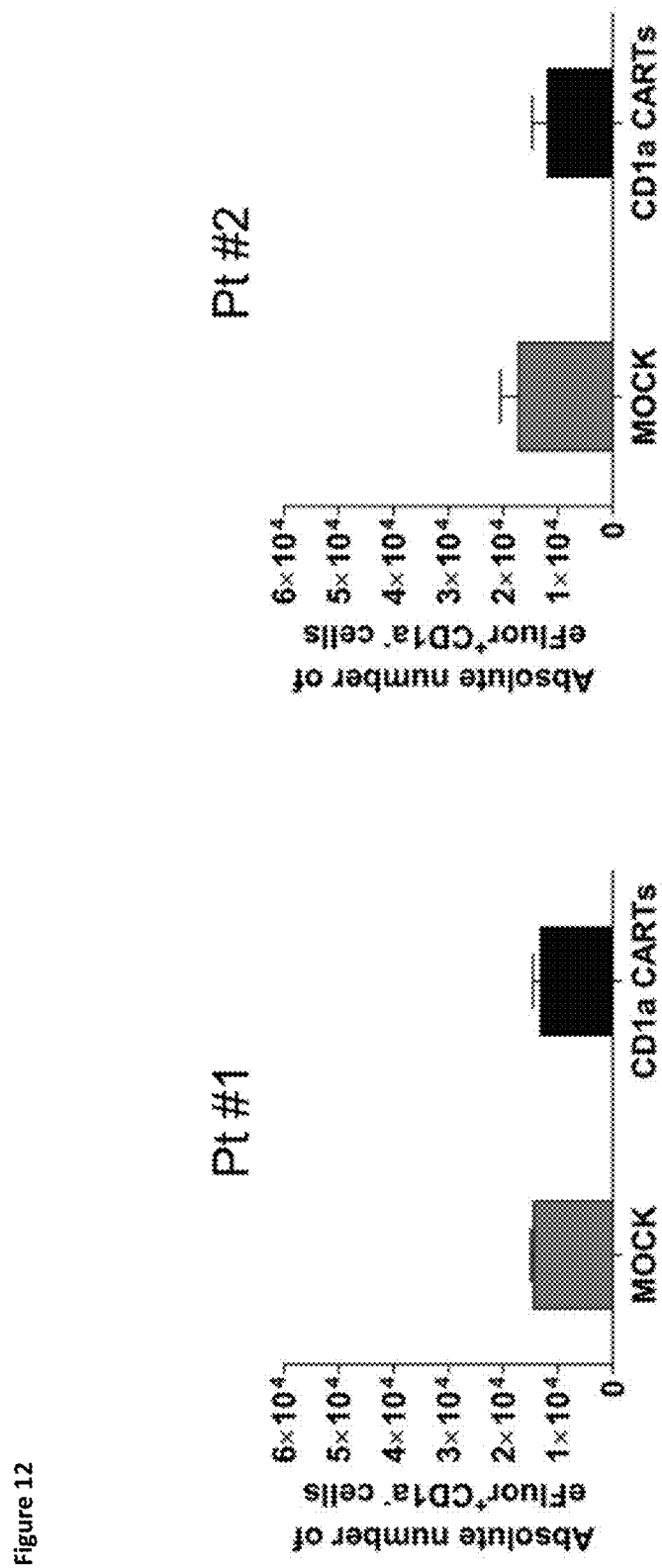

FIG. 12. The absolute number of CD1a– primary coT-ALL cells remains identical after either MOCK or CD1a CART exposure. This confirms that CD1a expression was not lost/downregulated by immune pressure.

SUMMARY OF THE INVENTION

The choice of the antigen against which we wish to re-direct T-cells represents a major advance to solve the problems associated with the shared expression of T-cell markers between normal and malignant T-cells. We identified that CD1a, a lipid-presenting molecule, is a suitable target for treating a large subset of T-ALL, i.e. cortical T-ALL.

We developed and functionally characterized CD1a-specific CARTs, which displayed robust cytotoxicity against T-ALL cell lines and primary cortical CD1a+ T-ALL cells both in vitro and in vivo in xenograft models. The CD1a CARTs continuously expanded 200-fold, similar to MOCK T-cells, demonstrating that redirecting CARTs against CD1a antigen does not induce T-cell fratricide. Also, the use of CD1a CARTs for cortical T-ALL bypasses the need for sophisticated genome editing-based disruption of target antigens in T-cells prior to CAR transduction as a strategy to avoid self-antigen-driven fratricide[15-17,19]. We further demonstrated that in steady-state hematopoiesis, CD1a is exclusively expressed in a subset of cortical CD34+CD7+ thymic T progenitors, whereas earlier CD34[high]CD7[high] T-progenitors lack CD1a. In addition, neither normal CD34+ HSPCs nor mature T-cells from multiple tissues express CD1a during ontogeny, thereby minimizing the risk of on-target/off-tumor toxicity. Indeed, when human fetal thymus-derived CD7+ thymocytes were exposed to CD1a CARTs, only the CD1a+ cortical thymocytes were eliminated by the CD1a CARTs, while developmentally earlier and later thymic T-lineage populations (CD34+ and CD34–) were not targeted, limiting the on-target/off-tumor effects to a developmentally transient thymic population of cortical thymocytes and further confirming the fratricide resistant nature of CD1a CARTs.

The exclusive thymic localization of cortical thymocytes, and the fact that thymic subpopulations of CD34+CD7+ CD1a− T-cell progenitors physiologically/constantly maturing into functional T cells reside upstream of CD1a+ cortical thymocytes, provides an additional level of safety for the use of CD CARTs in patients with R/R T-ALL. We do not expect irreversible toxicities or severe T-cell aplasia attributed to CD1a CARTs for the following reasons: i) the CD1a+ thymocyte population is a transient thymic T-cell fraction, eventually regenerated by upstream CD1a− T-cell progenitors; ii) CD1a CARTs themselves respond normally to viral antigens and therefore are likely to be protective against pathogens; iii) the clinical use of specific antibodies against CD5 or CD7[42] did not reveal severe or irreversible toxicities; iv) there are multiple studies that demonstrate extra-thymic maturation of T-cells and a balance between the innate and adaptive immune system that may, at least in part, guarantee immunological protection in patients who have undergone partial or total thymectomy[45-47].

Thus, in one aspect, the present invention provides a chimeric antigen receptor (CAR) comprising an extracellular domain comprising a CD1a targeting-moiety, a transmembrane domain, and an intracellular signaling domain.

The present invention also provides a nucleic acid encoding the CAR of the present invention. Further, the present invention provides a cell comprising the nucleic acid and/or CAR of the present invention. And, the present invention provides a pharmaceutical composition comprising a plurality of cells in accordance with the present invention and a pharmaceutically acceptable carrier or diluent.

The cell of the present invention or pharmaceutical composition of the present invention is provided for use as a medicament. In particular, the present invention provides a method of treating a CD1a-positive cancer comprising administering the cell of the present invention or the pharmaceutical composition of the present invention to a patient in need thereof.

DETAILED DESCRIPTION OF THE INVENTION

Definitions

"Administering" or "administration of" a medicament to a patient (and grammatical equivalents of this phrase) refers to direct administration, which may be administration to a patient by a medical professional or may be self-administration, and/or indirect administration, which may be the act of prescribing a drug. E.g., a physician who instructs a patient to self-administer a medicament or provides a patient with a prescription for a drug is administering the drug to the patient.

The term "affibody" refers to a protein that is derived from the Z domain of protein A and that been engineered to bind to a specific target (see Frejd & Kim, 2017. Exp Mol Med. 49(3): e306).

The term "antibody" refers to a molecule comprising at least one immunoglobulin domain that binds to, or is immunologically reactive with, a particular target. The term includes whole antibodies and any antigen binding portion or single chains thereof and combinations thereof; for instance, the term "antibody" in particular includes bivalent antibodies and bivalent bispecific antibodies.

A typical type of antibody comprises at least two heavy chains ("HC") and two light chains ("LC") interconnected by disulfide bonds.

Each "heavy chain" comprises a "heavy chain variable domain" (abbreviated herein as "VH") and a "heavy chain constant domain" (abbreviated herein as "CH"). The heavy chain constant domain typically comprises three constants domains, CH1, CH2, and CH3.

Each "light chain" comprises a "light chain variable domain" (abbreviated herein as "VL") and a "light chain constant domain" ("CL"). The light chain constant domain (CL) can be of the kappa type or of the lambda type. The VH and VL domains can be further subdivided into regions of hypervariability, termed Complementarity Determining Regions ("CDR"), interspersed with regions that are more conserved, termed "framework regions" ("FW").

Each VH and VL is composed of three CDRs and four FWs, arranged from amino-terminus to carboxy-terminus in the following order: FW1, CDR1, FW2, CDR2, FW3, CDR3, FW4. The present disclosure inter alia presents VH and VL sequences as well as the subsequences corresponding to CDR1, CDR2, and CDR3.

The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) JMB 273, 927-948 ("Chothia" numbering scheme).

Accordingly, a person skilled in the art would understand that the sequences of FW1, FW2, FW3 and FW4 are equally disclosed. For a particular VH, FW1 is the subsequence between the N-terminus of the VH and the N-terminus of H-CDR1, FW2 is the subsequence between the C-terminus of H-CDR1 and the N-terminus of H-CDR2, FW3 is the subsequence between the C-terminus of H-CDR2 and the N-terminus of H-CDR3, and FW4 is the subsequence between the C-terminus of H-CDR3 and the C-terminus of the VH. Similarly, for a particular VL, FW1 is the subsequence between the N-terminus of the VL and the N-terminus of L-CDR1, FW2 is the subsequence between the C-terminus of L-CDR1 and the N-terminus of L-CDR2. FW3 is the subsequence between the C-terminus of L-CDR2 and the N-terminus of L-CDR3, and FW4 is the subsequence between the C-terminus of L-CDR3 and the C-terminus of the VL.

The variable domains of the heavy and light chains contain a region that interacts with a binding target, and this region interacting with a binding target is also referred to as an "antigen-binding site" or "antigen binding site" herein. The constant domains of the antibodies can mediate the binding of the antibody to host tissues or factors, including various cells of the immune system (e.g., effector cells) and the first component (C1q) of the classical complement system. Exemplary antibodies of the present disclosure include typical antibodies, but also bivalent fragments and variations thereof such as a F(ab')2.

As used herein, the term "antibody" encompasses intact polyclonal antibodies, intact monoclonal antibodies, bivalent antibody fragments (such as F(ab')2), multispecific antibodies such as bispecific antibodies, chimeric antibodies, humanized antibodies, human antibodies, and any other modified immunoglobulin molecule comprising an antigen binding site.

An antibody can be of any the five major classes (isotypes) of immunoglobulins: IgA, IgD, IgE, IgG, and IgM, or subclasses thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as therapeutic agents or diagnostic agents to form immunoconjugates.

The term "anticalin" refers to a protein that is derived from the lipocalin and that been engineered to bind to a specific target (see Skerra, 2008. FEBS J. 275(11):2677-83).

The term "antigen-binding fragment" or "Fab" refers to an antibody fragment comprising one constant and one variable domain of each of the heavy and light chain. A Fab fragment may be obtained by digesting an intact monoclonal antibody with papain.

The term "cancer" refers to a group of diseases, which can be defined as any abnormal benign or malignant new growth of tissue that possesses no physiological function and arises from uncontrolled usually rapid cellular proliferation and has the potential to invade or spread to other parts of the body.

The term "CD1a" refers to a non-polymorphic MHC Class 1 related cell surface glycoprotein, expressed in association with β-2-microglobulin. CD1a is expressed by cortical thymocytes, Langerhans cells and by interdigitating cells. CD1a is also expressed by some malignancies of T cell lineage and in Langerhans cell histiocytosis. CD1a is expressed on cortical thymocytes, epidermal Langerhans cells, dendritic cells, on certain T-cell leukemias, and in various other tissues. CD1a is structurally related to the major histocompatibility complex (MHC) proteins and form heterodimers with β-2-microglobulin. Exemplary sequence and data related to human CD1a has been deposited in the UniProtKB database under ID number P06126.

"CD1a-positive" cancer, including a "CD1a-positive" cancerous disease, is one comprising cells, which have CD1a present at their cell surface. The term "CD1a-positive" also refers to a cancer that produces sufficient levels of CD1a at the surface of cells thereof, such that a CAR-comprising cell of the present invention has a therapeutic effect, mediated by the binding of the CAR to CD1a. In some embodiments, the CD1a-positive cancer is cortical T-cell acute lymphoblastic leukemia, and T-cell lymphoblastic lymphoma or Langerhans cell histiocytosis (LCH).

The term "CD1a-targeting moiety" refers to a substance that is able to bind CD1a. Within the context of a CAR, a CD1a-targeting moiety targets T cells to a CD1a-positive cell, preferably a cancer cell. Within the context of a CAR, it is to be understood that the CD1a-targeting moiety is genetically encodable.

The term "chimeric antigen receptor" or "CAR" refers to a synthetic receptor that targets T cells to a chosen antigen and reprograms T cell function, metabolism and persistence (see Riviére & Sadelain, 2017. *Mol Ther.* 25(5):1117-1124). Similarly, the term "CART" refers to a T cell that comprises a CAR.

"Combination therapy", "in combination with" or "in conjunction with" as used herein denotes any form of concurrent, parallel, simultaneous, sequential or intermittent treatment with at least two distinct treatment modalities (i.e., compounds, components, targeted agents or therapeutic agents). As such, the terms refer to administration of one treatment modality before, during, or after administration of the other treatment modality to the subject. The modalities in combination can be administered in any order. The therapeutically active modalities are administered together (e.g., simultaneously in the same or separate compositions, formulations or unit dosage forms) or separately (e.g., on the same day or on different days and in any order as according to an appropriate dosing protocol for the separate compositions, formulations or unit dosage forms) in a manner and dosing regimen prescribed by a medical care taker or according to a regulatory agency. In general, each treatment modality will be administered at a dose and/or on a time schedule determined for that treatment modality. Optionally, three or more modalities may be used in a combination therapy. Additionally, the combination therapies provided herein may be used in conjunction with other types of treatment. For example, other anti-cancer treatment may be selected from the group consisting of chemotherapy, surgery, radiotherapy (radiation) and/or hormone therapy, amongst other treatments associated with the current standard of care for the subject.

A "complete response" or "complete remission" or "CR" indicates the disappearance of all target lesions as defined in the RECIST v1.1 guideline. This does not always mean the cancer has been cured.

The term "costimulatory signaling domain" refers to a signaling moiety that provides to T cells a signal which, in addition to the primary signal provided by for instance the CD3ζ chain of the TCR/CD3 complex, mediates a T cell response, including, but not limited to, activation, proliferation, differentiation, cytokine secretion, and the like. A co-stimulatory domain can include all or a portion of, but is not limited to, CD27, CD28, 4-1BB (CD137), OX40 (CD134), CD30, CD40, 1COS, lymphocyte function-associated antigen-1 (LFA-1), CD2, CD7, LIGHT, NKG2C, B7-H3, and a ligand that specifically binds with CD83. In some embodiments, the co-stimulatory signaling domain is an intracellular signaling domain that interacts with other intracellular mediators to mediate a cell response including activation, proliferation, differentiation and cytokine secretion, and the like.

The term "designed ankyrin repeat proteins" or "DARPin" refers to a protein that is derived from an ankyrin repeat that has been engineered to bind to a specific target (see Plückthun, 2015. Annu Rev Pharmacol Toxicol. 55:489-511).

"Disease free survival" (DFS) refers to the length of time during and after treatment that the patient remains free of disease.

As used herein, the term "effective amount" of an agent, e.g., a therapeutic agent such as a CART, is that amount sufficient to effect beneficial or desired results, for example, clinical results, and, as such, an "effective amount" depends upon the context in which it is being applied. For example, in the context of administering a therapeutic agent that treats T-ALL, an effective amount can reduce the number of cancer cells; reduce the tumor size or burden; inhibit (i.e., slow to some extent and in a certain embodiment, stop) cancer cell infiltration into peripheral organs; inhibit (i.e., slow to some extent and in a certain embodiment, stop) tumor metastasis; inhibit, to some extent, tumor growth; relieve to some extent one or more of the symptoms associated with the cancer; and/or result in a favorable response such as increased progression-free survival (PFS), disease-free survival (DFS), or overall survival (OS), complete response (CR), partial response (PR), or, in some cases, stable disease (SD), a decrease in progressive disease (PD), a reduced time to progression (TTP) or any combination thereof. The term "effective amount" can be used interchangeably with "effective dose," "therapeutically effective amount," or "therapeutically effective dose".

The term "fynomer" refers to a protein that is derived from the SH3 domain of human Fyn kinase that has been engineered to bind to a specific target (see Bertschinger et al., 2007. Protein Eng Des Sel. 20(2):57-68).

The terms "individual", "patient" or "subject" are used interchangeably in the present application to designate a human being and are not meant to be limiting in any way. The "individual", "patient" or "subject" can be of any age, sex and physical condition. The term "patient in need thereof" usually refers to a patient who suffers from a CD1a-positive cancer.

"Infusion" or "infusing" refers to the introduction of a therapeutic agent-containing solution into the body through a vein for therapeutic purposes. Generally, this is achieved via an intravenous bag.

"Intracellular signaling domain" as used herein refers to all or a portion of one or more domains of a molecule (here the chimeric receptor molecule) that provides for activation of a lymphocyte. Intracellular domains of such molecules mediate a signal by interacting with cellular mediators to result in proliferation, differentiation, activation and other effector functions. Examples of intracellular signaling domains for use in a CAR of the invention include the intracellular sequences of the CD3 chain, and/or co-receptors that act in concert to initiate signal transduction following CAR engagement, as well as any derivative or variant of these sequences and any synthetic sequence that has the same functional capability. T cell activation can be said to be mediated by two distinct classes of cytoplasmic signaling sequence: those that initiate antigen-dependent primary activation and provide a T cell receptor like signal (primary cytoplasmic signaling sequences) and those that act in an antigen-independent manner to provide a secondary or co-stimulatory signal (secondary cytoplasmic signaling sequences). Primary cytoplasmic signaling sequences that act in a stimulatory manner may contain signaling motifs which are known as receptor tyrosine-based activation motifs or ITAMs. Examples of ITAM containing primary cytoplasmic signaling sequences include those derived from CD3ζ, FcRγ, CD3γ, CD3δ, CD3ε, CD5, CD22, CD79a, CD79b, and CD66d.

The term "monobody" refers to a protein that is derived from a fibronectin type III domain that has been engineered to bind to a specific target (see Koide et al., 2013. J Mol Biol. 415(2):393-405).

The term "nanobody" refers to a protein comprising the soluble single antigen-binding V-domain of a heavy chain antibody, preferably a camelid heavy chain antibody (see Bannas et al., 2017. Front Immunol. 8:1603).

"Overall Survival" (OS) refers to the time from patient enrollment to death or censored at the date last known alive. OS includes a prolongation in life expectancy as compared to naive or untreated individuals or patients. Overall survival refers to the situation wherein a patient remains alive for a defined period of time, such as one year, five years, etc., e.g., from the time of diagnosis or treatment.

A "partial response" or "PR" refers to at least a 30% decrease in the sum of diameters of target lesions, taking as reference the baseline sum diameter, in response to treatment, as defined in the RECIST v1.1 guideline.

The term "peptide aptamer" refers to a short, 5-20 amino acid residue sequence that can bind to a specific target. Peptide aptamers are typically inserted within a loop region of a stable protein scaffold (see Reverdatto et al., 2015. Curr Top Med Chem. 15 (12): 1082-101).

As used herein, "pharmaceutically acceptable carrier" or "pharmaceutically acceptable diluent" means any and all solvents, dispersion media, coatings, antibacterial and antifungal agents, isotonic and absorption delaying agents, compatible with pharmaceutical administration. The use of such media and agents for pharmaceutically active substances is well known in the art. Acceptable carriers, excipients, or stabilizers are nontoxic to recipients at the dosages and concentrations employed and, without limiting the scope of the present invention, include: additional buffering agents; preservatives; co-solvents; antioxidants, including ascorbic acid and methionine; chelating agents such as EDTA; metal complexes (e.g., Zn-protein complexes); biodegradable polymers, such as polyesters; salt-forming counterions, such as sodium, polyhydric sugar alcohols; amino acids, such as alanine, glycine, glutamine, asparagine, histidine, arginine, lysine, ornithine, leucine, 2-phenylalanine, glutamic acid, and threonine; organic sugars or sugar alcohols, such as lactitol, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, [alpha]-monothioglycerol, and sodium thio sulfate; low molecular weight proteins, such as human serum albumin, bovine serum albumin, gelatin, or other immunoglobulins; and hydrophilic polymers, such as polyvinylpyrrolidone. Other pharmaceutically acceptable carriers, excipients, or stabilizers, such as those described in Remington's Pharmaceutical Sciences 16th edition, Osol, A. Ed. (1980) may also be included in a pharmaceutical composition described herein, provided that they do not adversely affect the desired characteristics of the pharmaceutical composition.

"Progressive disease" or "disease that has progressed" refers to the appearance of one more new lesions or tumors and/or the unequivocal progression of existing non-target lesions as defined in the RECIST v1.1 guideline. Progressive disease or disease that has progressed can also refer to a tumor growth of more than 20 percent since treatment began, either due to an increase in mass or in spread of the tumor.

"Progression free survival" (PFS) refers to the time from enrollment to disease progression or death. PFS is generally measured using the Kaplan-Meier method and Response Evaluation Criteria in Solid Tumors (RECIST) 1.1 standards. Generally, progression free survival refers to the situation wherein a patient remains alive, without the cancer getting worse.

The term "RECIST" means Response Evaluation Criteria in Solid Tumours. RECIST guideline, criteria, or standard, describes a standard approach to solid tumor measurement and definitions for objective assessment of change in tumor size for use in adult and pediatric cancer clinical trials. RECIST v1.1 means version 1.1 of the revised RECIST guideline and it is published in European Journal of Cancers 45 (2009) 228-247.

The term "repebody" refers to a protein that is derived from a leucine-rich repeat module and that been engineered to bind to a specific target (see Lee et al., 2012. PNAS. 109(9): 3299-3304).

The term "respond favorably" generally refers to causing a beneficial state in a subject. With respect to cancer treatment, the term refers to providing a therapeutic effect on the subject. Positive therapeutic effects in cancer can be measured in a number of ways (See, Weber, 2009. J Nucl Med. 50 Suppl 1:1S-10S). For example, tumor growth inhibition, molecular marker expression, serum marker expression, and molecular imaging techniques can all be used to assess therapeutic efficacy of an anti-cancer therapeutic. With respect to tumor growth inhibition, according to NCI standards, a T/C≤42% is the minimum level of antitumor activity. A T/C≤10% is considered a high anti-tumor activity level, with T/C (%)=Median tumor volume of the treated/Median tumor volume of the control×100. A favorable response can be assessed, for example, by increased progression-free survival (PFS), disease-free survival (DFS), or overall survival (OS), complete response (CR), partial response (PR), or, in some cases, stable disease (SD), a decrease in progressive disease (PD), a reduced time to progression (TTP) or any combination thereof.

The term "sequence identity" refers to a percentage value obtained when two sequences are compared using a pairwise sequence alignment tool. In the present case, the sequence identity is obtained using the global alignment tool "EMBOSS Needle" using the default settings (Rice et al., 2000. Trends Genet. 16(6):276-7; Li et al., 2015. Nucleic Acids Res. 43(W1):W580-4). The global alignment tool is available at: https://www.ebi.ac.uk/Tools/psa/.

The term "single-chain antigen-binding fragment" or "scFab" refers to a fusion protein comprising one variable and one constant domain of the light chain of an antibody attached to one variable and one constant domain of the heavy chain of an antibody, wherein the heavy and light chains are linked together through a short peptide.

The term "single-chain variable fragment" or "scFv" refers to a fusion protein comprising the variable domains of the heavy chain and light chain of an antibody linked to one another with a peptide linker. The term also includes a disulfide stabilized Fv (dsFv). Methods of stabilizing scFvs with disulfide bonds are disclosed in Reiter et al., 1996. Nat Biotechnol. 14(10):1239-45.

"Stable disease" refers to disease without progression or relapse as defined in the RECIST v1.1 guideline. In stable disease there is neither sufficient tumor shrinkage to qualify for partial response, nor sufficient tumor increase to qualify as progressive disease.

"Time to Tumor Progression" (TTP) is defined as the time from enrollment to disease progression. TTP is generally measured using the RECIST v1.1 criteria.

The terms "treatment" and "therapy", as used in the present application, refer to a set of hygienic, pharmacological, surgical and/or physical means used with the intent to cure and/or alleviate a disease and/or symptoms with the goal of remediating the health problem. The terms "treatment" and "therapy" include preventive and curative methods, since both are directed to the maintenance and/or reestablishment of the health of an individual or animal. Regardless of the origin of the symptoms, disease and disability, the administration of a suitable medicament to alleviate and/or cure a health problem should be interpreted as a form of treatment or therapy within the context of this application.

Chimeric Antigen Receptor

In one aspect, the present invention provides a chimeric antigen receptor (CAR) comprising an extracellular domain comprising a CD1a targeting-moiety, a transmembrane domain, and an intracellular signaling domain.

CD1a Targeting-Moiety

In some embodiments, the CD1a-targeting moiety is an antibody, anticalin, repebody, monobody, scFv, Fab, scFab, affibody, fynomer, DARPin, nanobody, or peptide aptamer that specifically binds to CD1a.

Binding molecules that bind specifically to CD1a may be very useful in the diagnosis and treatment of the disorders mentioned above. Several murine monoclonal antibodies against CD1a are known in the field (Kelly (1994), Amiot et al. (1986), Fume et al. (1992)). However, murine antibodies are limited for in vivo use due to issues associated with the administration of murine antibodies to humans, such as short serum half-life, the inability to trigger certain human effector functions and the generation of an undesired immune response against the murine antibody (Van Kroonenburgh and Pauwels (1988)). New human antibodies have been developed (Bechan (2012), and Gitanjali (2005) in recent years overcoming these previously mentioned drawbacks. Besides NA1/34.HLK, other hybridomas are commercially available, e.g. OKT6 (IgG1 isotype), from SIGMA ALDRICH.

Please refer to:

Amiot M., Bernard A., Raynal B., Knapp W., Deschildre C. and Boumsell L. (1986), *J. Immunol.* 136:1752-1757.

Fume M., Nindl M., Kawabe K., Nakamura K., Ishibashi Y. and Sagawa K. (1992), *J. Am. Acad. Dermatol.* 27:419-42

Kelly K. M., Beverly P. C., Chu A. C., Davenport V., Gordon I., Smith M. and Pritchard J. (1994), *J. Pediatr.* 125:717-722

Van Kroonenburgh M. J. and Pauwels E. K. (1988), *Nucl. Med. Commun.* 9:919-930.

Gitanjali Bechan, David W. Lee, R. Maarten Egeler and Robert J. Arceci Blood 2005 106:4815

Bechan, G. I., Lee, D. W., Zajonc, D. M., Heckel, D., Xian, R., Throsby, M., Meijer, M., Germeraad, W. T., Kruisbeek, A. M., Maarten Egeler, R. and Arceci, R. J. (2012), Br J Haematol, 159: 299-310.

Phage display and combinatorial methods for generating antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) Bio/Technology 9:1370-1372; Hay et al. (1992) Hum Antibod Hybridomas 3:81-85; Huse et al. (1989) Science 246:1275-1281; Griffths et al. (1993) EMBO J 12:725-734; Hawkins et al. (1992) J Mol Biol 226:889-896; Clackson et al. (1991) Nature 352:624-628; Gram et al. (1992) PNAS 89:3576-3580; Garrad et al. (1991) Bio/Technology 9:1373-1377; Hoogenboom et al. (1991) Nuc Acid Res 19:4133-4137; and Barbas et al. (1991) PNAS 88:7978-7982, the contents of all of which are incorporated by reference herein).

Further, methods of generating and selecting non-immunglobulin scaffolds that bind to a particular target are known in the art (see, for example, Škrlec, et al., 2015. Trends Biotechnol. 33(7):408-18).

In some embodiments, the CD1a-targeting moiety is an antibody, scFv, Fab, or scFab comprising a VL domain and VH domain, wherein said VL domain comprises LCDR1, LCDR2 and LCDR3 polypeptides and said VH domain comprises HCDR1, HCDR2 and HCDR3 polypeptides, and LCDR1 consists of [QDINKY] (SEQ ID NO: 1), LCDR2 consists of [YTS], LCDR3 consists of [LHYDNLPWT] (SEQ ID NO: 3), HCDR1 consists of [GYAFSTYT] (SEQ ID NO: 4), HCDR2 consists of [INPNSAST] (SEQ ID NO: 5), and HCDR3 consists of [ARGFYTMDY] (SEQ ID NO: 6).

In some embodiments, the CD1a-targeting moiety is a scFv comprising a VL domain and VH domain, wherein said VL domain comprises LCDR1, LCDR2 and LCDR3 polypeptides and said VH domain comprises HCDR1, HCDR2 and HCDR3 polypeptides, and LCDR1 consists of [QDINKY] (SEQ ID NO: 1), LCDR2 consists of [YTS], LCDR3 consists of [LHYDNLPWT] (SEQ ID NO: 3), HCDR1 consists of [GYAFSTYT] (SEQ ID NO: 4), HCDR2 consists of [INPNSAST] (SEQ ID NO: 5), and HCDR3 consists of [ARGFYTMDY] (SEQ ID NO: 6).

In some embodiments, the CD1a-targeting moiety is an antibody, scFv, Fab, or scFab comprising a VL domain and VH domain, wherein the VL domain consists of SEQ ID NO: 7 and the VH domain consists of SEQ ID NO: 8.

In some embodiments, the CD1a-targeting moiety is a scFv comprising a VL domain and VH domain, wherein the VL domain consists of SEQ ID NO: 7 and the VH domain consists of SEQ ID NO: 8.

VL domain
(SEQ ID NO: 7)
[RDIQMTQSPSSLSASLGGKVTITCQASQDINKYIAWYQFKPGKGPRLLIH

YTSTLQPAIPSRFSGSGSGREYSFSISNLEPEDIATYYCLHYDNLPWTFGG

GTKLEIKRA]

VH domain
(SEQ ID NO: 8)
[QVQLQQSGAELARPGASVKMSCKASGYAFSTYTMHWVKQRPRQGLEWIGY

INPNSASTSYNENFKDKATLTADKSSNTAYMHLSSLTSEDSAVYYCARGFY

TMDYWGQGTSVTVSS]

In some embodiments, the CD1a-targeting moiety is a scFv comprising or consisting of SEQ ID NO: 9.

scFv derived from clone NA1/34.HLK
(SEQ ID NO: 9)
[QVQLQQSGAELARPGASVKMSCKASGYAFSTYTMHWVKQRPRQGLEWIGY

INPNSASTSYNENFKDKATLTADKSSNTAYMHLSSLTSEDSAVYYCARGFY

TMDYWGQGTSVTVSSGGGGSGGGGSGGGGSGGGGSRDIQMTQSPSSLSASL

GGKVTITCQASQDINKYIAWYQFKPGKGPRLLIHYTSTLQPAIPSRFSGSG

SGREYSFSISNLEPEDIATYYCLHYDNLPWTFGGGTKLEIKRA]

Transmembrane Domain

The transmembrane domain may be derived either from a natural or a synthetic source. When the source is natural, the domain may be derived from any membrane-bound or transmembrane protein. Transmembrane regions may comprise at least the transmembrane region(s) of the α-, β- or ζ-chain of CD28, CD3, CD45, CD4, CD8, CD9, CD16, CD22, CD33, CD37, CD64, CD80, CD86, CD134, CD137, or CD154.

A transmembrane domain may be synthetic or a variant of a naturally occurring transmembrane domain. In some embodiments, synthetic or variant transmembrane domains comprise predominantly hydrophobic residues such as leucine and valine.

In some embodiments, the transmembrane domain comprises the transmembrane domain of CD28, CD3, CD45, CD4, CD8, CD9, CD16, CD22, CD33, CD37, CD64, CD80, CD86, CD134, CD137, or CD154, or a variant thereof, wherein the variant thereof has a 95% sequence identity.

In some embodiments, the transmembrane domain comprises the transmembrane domain of CD28, CD3, CD45, CD4, CD8, CD9, CD16, CD22, CD33, CD37, CD64, CD80, CD86, CD134, CD137, CD154, or a variant thereof, wherein the variant thereof has a 98% sequence identity.

In some embodiments, the transmembrane domain comprises the transmembrane domain of CD28, CD3, CD45, CD4, CD8, CD9, CD16, CD22, CD33, CD37, CD64, CD80, CD86, CD134, CD137, or CD154.

In some embodiments, the transmembrane domain comprises the transmembrane domain of CD8 or a variant thereof, wherein the variant thereof has a 95% sequence identity.

In some embodiments, the transmembrane domain comprises the transmembrane domain of CD8 or a variant thereof, wherein the variant thereof has a 98% sequence identity.

In some embodiments, the transmembrane domain comprises the transmembrane domain of CD8.

In some embodiments, the transmembrane domain comprises SEQ ID NO: 10 or a sequence that has 95% sequence identity to SEQ ID NO: 10.

In some embodiments, the transmembrane domain comprises SEQ ID NO: 10 or a sequence that has 98% sequence identity to SEQ ID NO: 10.

In some embodiments, the transmembrane domain comprises SEQ ID NO: 10. In some embodiments, the transmembrane domain consists of SEQ ID NO: 10.

Transmembrane domain derived from CD8
(SEQ ID NO: 10)
[TTTPAPRPPTPAPTIASQPLSLRPEACRPAAGGAVHTRGLDFACDIYIWA

PLAGTCGVLLLSLVITLYC]

Intracellular Signaling Domain

The intracellular signaling domain provides for the activation of at least one function of the cell expressing the CAR upon binding to the ligand expressed on tumor cells. In some embodiments, the intracellular signaling domain contains one or more intracellular signaling domains. In some embodiments, the intracellular signaling domain is a portion of and/or a variant of an intracellular signaling domain that provides for activation of at least one function of the CAR-comprising cell.

In some embodiments, the intracellular signaling domain comprises the intracellular domain of CD3ζ, FcRγ, CD3γ, CD3δ, CD3ε, CD5, CD22, CD79a, CD79b, CD66b, or a variant thereof, wherein the variant thereof has a 95% sequence identity.

In some embodiments, the intracellular signaling domain comprises the intracellular domain of CD3ζ, FcRγ, CD3γ, CD3δ, CD3ε, CD5, CD22, CD79a, CD79b, CD66b, or a variant thereof, wherein the variant thereof has a 98% sequence identity.

In some embodiments, the intracellular signaling domain comprises the intracellular domain of CD3ζ, FcRγ, CD3γ, CD3δ, CD3ε, CD5, CD22, CD79a, CD79b or CD66b.

In some embodiments, the intracellular signaling domain comprises the intracellular domain of CD3 or a variant thereof, wherein the variant thereof has a 95% sequence identity.

In some embodiments, the intracellular signaling domain comprises the intracellular domain of CD3 or a variant thereof, wherein the variant thereof has a 98% sequence identity.

In some embodiments, the intracellular signaling domain comprises the intracellular domain of CD3.

In some embodiments, the intracellular signaling domain comprises SEQ ID NO: 11 or a sequence that has 95% sequence identity to SEQ ID NO: 11.

In some embodiments, the intracellular signaling domain comprises SEQ ID NO: 11 or a sequence that has 98% sequence identity to SEQ ID NO: 11.

In some embodiments, the intracellular signaling domain comprises SEQ ID NO: 11 or a sequence that has 99% sequence identity to SEQ ID NO: 11.

In some embodiments, the intracellular signaling domain comprises SEQ ID NO: 11. In some embodiments, the intracellular signaling domain consists of SEQ ID NO: 11.

Intracellular signaling domain derived from CD3ζ
(SEQ ID NO: 11)
[RVKFSRSADAPAYQQGQNQLYNELNLGRREEYDVLDKRRGRDPEMGGKPQ

RRKNPQEGLYNELQKDKMAEAYSEIGMKGERRRGKGHDGLYQGLSTATKDT

YDALHMQALPPR]

Costimulatory Signaling Domain

In some embodiments, the CAR may further comprise a costimulatory signaling domain. In some embodiments, the costimulatory signaling domain comprises the intracellular domain of CD27, CD28, CD137, CD134, CD30, CD40, lymphocyte function-associated antigen-1 (LFA-1), CD2, CD7, LIGHT, NKG2C, CD276 or a variant thereof, wherein the variant thereof has a 95% sequence identity.

In some embodiments, the costimulatory signaling domain comprises the intracellular domain of CD27, CD28, CD137, CD134, CD30, CD40, lymphocyte function-associated antigen-1 (LFA-1), CD2, CD7, LIGHT, NKG2C, CD276 or a variant thereof, wherein the variant thereof has a 98% sequence identity.

In some embodiments, the costimulatory signaling domain comprises the intracellular domain of CD27, CD28, CD137, CD134, CD30, CD40, lymphocyte function-associated antigen-1 (LFA-1), CD2, CD7, LIGHT, NKG2C, or CD276.

In some embodiments, the costimulatory signaling domain comprises the intracellular domain of CD137 or a variant thereof, wherein the variant thereof has a 95% sequence identity.

In some embodiments, the costimulatory signaling domain comprises the intracellular domain of CD137 or a variant thereof, wherein the variant thereof has a 98% sequence identity.

In some embodiments, the costimulatory signaling domain comprises the intracellular domain of CD137.

In some embodiments, the costimulatory signaling domain comprises SEQ ID NO: 12 or a sequence that has 95% sequence identity to SEQ ID NO: 12.

In some embodiments, the costimulatory signaling domain comprises SEQ ID NO: 12 or a sequence that has 98% sequence identity to SEQ ID NO: 12.

In some embodiments, the costimulatory signaling domain comprises SEQ ID NO: 12 or a sequence that has 99% sequence identity to SEQ ID NO: 12.

In some embodiments, the costimulatory signaling domain comprises SEQ ID NO: 12. In some embodiments, the costimulatory signaling domain consists of SEQ ID NO: 12.

Costimulatory signaling domain derived from CD137
(SEQ ID NO: 12)
[KRGRKKLLYIFKQPFMRPVQTTQEEDGCSCRFPEEEEGGCEL]

Full Sequence CARs According to the Present Invention

In some embodiments, the CAR comprises:
(i) a scFv comprising a VL domain and VH domain, wherein said VL domain comprises LCDR1, LCDR2 and LCDR3 polypeptides and said VH domain comprises HCDR1, HCDR2 and HCDR3 polypeptides, and LCDR1 consists of [QDINKY] (SEQ ID NO: 1), LCDR2 consists of [YTS], LCDR3 consists of [LHYDNLPWT] (SEQ ID NO: 3), HCDR1 consists of [GYAFSTYT] (SEQ ID NO: 4), HCDR2 consists of [INPNSAST] (SEQ ID NO: 5), and HCDR3 consists of [ARGFYTMDY] (SEQ ID NO: 6);
(ii) a transmembrane domain comprising SEQ ID NO: 10 or a sequence that has 95% sequence identity to SEQ ID NO: 10;
(iii) an intracellular signaling domain comprising SEQ ID NO: 11 or a sequence that has 95% sequence identity to SEQ ID NO: 11; and
(iv) a costimulatory signaling domain comprising SEQ ID NO: 12 or a sequence that has 95% sequence identity to SEQ ID NO: 12.

In some embodiments, the CAR comprises:
(i) a scFv comprising a VL domain and VH domain, wherein said VL domain comprises LCDR1, LCDR2 and LCDR3 polypeptides and said VH domain comprises HCDR1, HCDR2 and HCDR3 polypeptides, and LCDR1 consists of [QDINKY] (SEQ ID NO: 1), LCDR2 consists of [YTS], LCDR3 consists of [LHYDNLPWT] (SEQ ID NO: 3), HCDR1 consists of [GYAFSTYT] (SEQ ID NO: 4), HCDR2 consists of [INPNSAST] (SEQ ID NO: 5), and HCDR3 consists of [ARGFYTMDY] (SEQ ID NO: 6);
(ii) a transmembrane domain comprising SEQ ID NO: 10 or a sequence that has 98% sequence identity to SEQ ID NO: 10;
(iii) an intracellular signaling domain comprising SEQ ID NO: 11 or a sequence that has 98% sequence identity to SEQ ID NO: 11; and
(iv) a costimulatory signaling domain comprising SEQ ID NO: 12 or a sequence that has 98% sequence identity to SEQ ID NO: 12.

In some embodiments, the CAR comprises:
(i) a scFv comprising a VL domain and VH domain, wherein said VL domain comprises LCDR1, LCDR2 and LCDR3 polypeptides and said VH domain comprises HCDR1, HCDR2 and HCDR3 polypeptides, and LCDR1 consists of [QDINKY] (SEQ ID NO: 1), LCDR2 consists of [YTS], LCDR3 consists of [LHYDNLPWT] (SEQ ID NO: 3), HCDR1 consists of [GYAFSTYT] (SEQ ID NO: 4), HCDR2 consists of [INPNSAST] (SEQ ID NO: 5), and HCDR3 consists of [ARGFYTMDY] (SEQ ID NO: 6);
(ii) a transmembrane domain comprising SEQ ID NO: 10 or a sequence that has 98% sequence identity to SEQ ID NO: 10;
(iii) an intracellular signaling domain comprising SEQ ID NO: 11 or a sequence that has 99% sequence identity to SEQ ID NO: 11; and
(iv) a costimulatory signaling domain comprising SEQ ID NO: 12 or a sequence that has 99% sequence identity to SEQ ID NO: 12.

In some embodiments, the CAR comprises:
(i) a scFv comprising a VL domain and VH domain, wherein said VL domain comprises LCDR1, LCDR2 and LCDR3 polypeptides and said VH domain comprises HCDR1, HCDR2 and HCDR3 polypeptides, and LCDR1 consists of [QDINKY] (SEQ ID NO: 1), LCDR2 consists of [YTS], LCDR3 consists of [LHYDNLPWT] (SEQ ID NO: 3), HCDR1 consists of [GYAFSTYT] (SEQ ID NO: 4), HCDR2 consists of [INPNSAST] (SEQ ID NO: 5), and HCDR3 consists of [ARGFYTMDY] (SEQ ID NO: 6);
(ii) a transmembrane domain comprising SEQ ID NO: 10;
(iii) an intracellular signaling domain comprising SEQ ID NO: 11; and
(iv) a costimulatory signaling domain comprising SEQ ID NO: 12.

In some embodiments, the CAR comprises:
(i) a scFv comprising a VL domain and VH domain, wherein said VL domain comprises LCDR1, LCDR2 and LCDR3 polypeptides and said VH domain comprises HCDR1, HCDR2 and HCDR3 polypeptides, and LCDR1 consists of [QDINKY] (SEQ ID NO: 1), LCDR2 consists of [YTS], LCDR3 consists of [LHYDNLPWT] (SEQ ID NO: 3), HCDR1 consists of [GYAFSTYT] (SEQ ID NO: 4), HCDR2 consists of [INPNSAST] (SEQ ID NO: 5), and HCDR3 consists of [ARGFYTMDY] (SEQ ID NO: 6);
(ii) a transmembrane domain consisting of SEQ ID NO: 10;
(iii) an intracellular signaling domain consisting of SEQ ID NO: 11; and
(iv) a costimulatory signaling domain consisting of SEQ ID NO: 12.

In some embodiments, the CAR comprises:
(i) a scFv comprising a VL domain and VH domain, wherein the VL domain consists of SEQ ID NO: 7 and the VH domain consists of SEQ ID NO: 8;
(ii) a transmembrane domain comprising SEQ ID NO: 10 or a sequence that has 95% sequence identity to SEQ ID NO: 10;
(iii) an intracellular signaling domain comprising SEQ ID NO: 11 or a sequence that has 95% sequence identity to SEQ ID NO: 11; and
(iv) a costimulatory signaling domain comprising SEQ ID NO: 12 or a sequence that has 95% sequence identity to SEQ ID NO: 12.

In some embodiments, the CAR comprises:
(i) a scFv comprising a VL domain and VH domain, wherein the VL domain consists of SEQ ID NO: 7 and the VH domain consists of SEQ ID NO: 8;
(ii) a transmembrane domain comprising SEQ ID NO: 10 or a sequence that has 98% sequence identity to SEQ ID NO: 10;
(iii) an intracellular signaling domain comprising SEQ ID NO: 11 or a sequence that has 98% sequence identity to SEQ ID NO: 11; and
(iv) a costimulatory signaling domain comprising SEQ ID NO: 12 or a sequence that has 98% sequence identity to SEQ ID NO: 12.

In some embodiments, the CAR comprises:
(i) a scFv comprising a VL domain and VH domain, wherein the VL domain consists of SEQ ID NO: 7 and the VH domain consists of SEQ ID NO: 8;
(ii) a transmembrane domain comprising SEQ ID NO: 10 or a sequence that has 98% sequence identity to SEQ ID NO: 10;
(iii) an intracellular signaling domain comprising SEQ ID NO: 11 or a sequence that has 99% sequence identity to SEQ ID NO: 11; and
(iv) a costimulatory signaling domain comprising SEQ ID NO: 12 or a sequence that has 99% sequence identity to SEQ ID NO: 12.

In some embodiments, the CAR comprises:
(i) a scFv comprising a VL domain and VH domain, wherein the VL domain consists of SEQ ID NO: 7 and the VH domain consists of SEQ ID NO: 8;
(ii) a transmembrane domain comprising SEQ ID NO: 10;
(iii) an intracellular signaling domain comprising SEQ ID NO: 11; and
(iv) a costimulatory signaling domain comprising SEQ ID NO: 12.

In some embodiments, the CAR comprises:
(i) a scFv comprising a VL domain and VH domain, wherein the VL domain consists of SEQ ID NO: 7 and the VH domain consists of SEQ ID NO: 8;
(ii) a transmembrane domain consisting of SEQ ID NO: 10;
(iii) an intracellular signaling domain consisting of SEQ ID NO: 11; and
(iv) a costimulatory signaling domain consisting of SEQ ID NO: 12.

In some embodiments, the CAR comprises or consists of SEQ ID NO: 2 or a sequence that has 95% sequence identity with SEQ ID NO: 2. In some embodiments, the CAR comprises or consists of SEQ ID NO: 2 or a sequence that has 98% sequence identity with SEQ ID NO: 2. In some embodiments, the CAR comprises or consists of SEQ ID NO: 2 or a sequence that has 99% sequence identity with SEQ ID NO: 2. In some embodiments, the CAR comprises or consists of SEQ ID NO: 2.

```
Full sequence of the CAR
                                        (SEQ ID NO: 2)
[MALPVTGLLLSLGLLLHAARPTGQVQLQQSGAELARPGASVKMSCKASGY

AFSTYTMHWVKQRPRQGLEWIGYINPNSASTSYNENFKDKATLTADKSSNT

AYMHLSSLTSEDSAVYYCARGEYTMDYWGQGTSVTVSSGGGGSGGGGSGGG

GSGGGGSRDIQMTQSPSSLSASLGGKVTITCQASQDINKYIAWYQFKPGKG

PRLLIHYTSTLQPAIPSRFSGSGSGREYSFSISNLEPEDIATYYCLHYDNL

PWTFGGGTKLEIKRATTTPAPRPPTPAPTIASQPLSLRPEACRPAAGGAVH

TRGLDFACDIYIWAPLAGTCGVLLLSLVITLYCKRGRKKLLYIFKQPFMRP

VQTTQEEDGCSCRFPEEEEGGCELRVKFSRSADAPAYQQGQNQLYNELNLG

RREEYDVLDKRRGRDPEMGGKPQRRKNPQEGLYNELQKDKMAEAYSEIGMK

GERRRGKGHDGLYQGLSTATKDTYDALHMQALPPR]
```

Nucleic Acid

In one aspect, the present invention provides a nucleic acid encoding any one of the CARS of the present invention, including any one of the CARS disclosed above. The nucleic acid sequence that encodes the chimeric receptor links together a number of modular components that can be excised and replaced with other components in order to customize the chimeric receptor for efficient T cell activation and recognition of CD1a.

In some embodiments, the nucleic acid is suitable for transducing or transforming a cell. In some embodiments, the nucleic acid is suitable for transducing or transforming a T cell for use in adoptive immunotherapy.

In some embodiments, the nucleic acid is codon optimized for expression in mammalian cells. Codon optimization methods are known in the art (see, for example, Parret et al., 2016. Curr Opin Struct Biol. 39: 155-162).

The nucleic acid of the present invention may be comprised in a γ-retroviral or lentiviral vector which can be used to transduce or transform a T cell (see Riviére & Sadelain, 2017. Mol Ther. 25(5):1117-1124). The nucleic acid may also be inserted into a cell through the use of DNA transposons, RNA transfection or genome editing techniques such as TALEN, ZFN and CRISPR/Cas9 (see Riviére & Sadelain, 2017. Mol Ther. 25(5):1117-1124).

Cells

In one aspect, the present invention provides a cell comprising the nucleic acid of the present invention and/or the CAR of the present invention. In some embodiments, the cell is a T-cell (referred to as a CART).

In some embodiments, the cell is a naïve T cell, memory stem T cell or central memory T cell. It is currently thought that these cells are better suited for adaptive immunotherapy (see Rivière & Sadelain, 2017. Mol Ther. 25(5):1117-1124).

In some embodiments, the cell is an autologous T cell. The term "autologous cell" refers to a cell obtained from the same patient that is to be treated using any one of the methods of the present invention. It is noted that flow cytometric analysis of peripheral blood obtained from 40 patients with active T-cell acute lymphoblastic leukemia revealed the presence of normal CD3+CD1a− T-cells in all the patients. Thus, it is entirely possible to treat a patient using an autologous T cell comprising the nucleic acid and/or CAR of the present invention.

In some embodiments, the cell is an allo-tolerant T cell. The term "allo-tolerant cell" refers to a cell that has been engineered to decrease the risk of a Graft-versus-host disease response. In some embodiments, this is achieved by genomic editing-mediated deletion of TCR and/or β2-microglobulin[15,19]. Allo-tolerant cells are known in the art (see section of allogeneic T cells in Riviére & Sadelain, 2017. Mol Ther. 25(5):1117-1124).

In some embodiments, the T cell is a CD3-positive and CD1a-negative T cell.

In some embodiments, the cell is a lymphoid precursor, embryonic stem cell or an induced pluripotent stem cell with the capacity to differentiate into a mature T cell (see Riviére & Sadelain, 2017. Mol Ther. 25(5):1117-1124).

Pharmaceutical Composition

In one aspect, the present invention provides a pharmaceutical composition comprising a plurality of cells of the present invention and a pharmaceutically acceptable carrier or diluent.

A pharmaceutical composition as described herein may also contain other substances. These substances include, but are not limited to, cryoprotectants, surfactants, anti-oxidants, and stabilizing agents. The term "cryoprotectant" as used herein, includes agents which provide stability to the CARTs against freezing-induced stresses. Non-limiting examples of cryoprotectants include sugars, such as sucrose, glucose, trehalose, mannitol, mannose, and lactose; polymers, such as dextran, hydroxyethyl starch and polyethylene glycol; surfactants, such as polysorbates (e.g., PS-20 or PS-80); and amino acids, such as glycine, arginine, leucine, and serine. A cryoprotectant exhibiting low toxicity in biological systems is generally used.

In some embodiments, the cells are formulated by first harvesting them from their culture medium, and then washing and concentrating the cells in a medium and container system suitable for administration (a "pharmaceutically acceptable" carrier) in a therapeutically effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumin, fetal bovine serum or other human serum components.

In one aspect, the present invention provides a cell according to the present invention or a pharmaceutical composition according to the present invention for use as a medicament.

Methods of Treatment

In one aspect, the present invention provides a method of treating a CD1a-positive cancer comprising administering the cell of the present invention or the pharmaceutical composition of the present invention to a patient in need thereof.

In some embodiments, the patient is administered a therapeutically effective amount of cells. In some embodiments, the patient is administered at least $10^2$, $10^3$, $10^4$, $10^5$, $10^6$, $10^7$, $10^8$, $10^9$ or $10^{10}$ cells. The number of cells will depend upon the ultimate use for which the composition is intended as will the type of cells included therein. For example, if cells that are specific for a particular antigen are desired, then the population will contain greater than 70%, generally greater than 80%, 85% and 90-95% of such cells. For uses provided herein, the cells are generally in a volume of a liter or less, can be 500 ml or less, even 250 ml or less, or 100 ml or less. The clinically relevant number of cells can be apportioned into multiple infusions that cumulatively equal or exceed $10^2$, $10^3$, $10^4$, $10^5$, $10^6$, $10^7$, $10^8$, $10^9$ or $10^{10}$ cells.

In some embodiments, the cell or pharmaceutical composition is administered intravenously, intraperitoneally, into the bone marrow, into the lymph node, and/or into cerebrospinal fluid.

In some embodiments, the method comprises a combination therapy. In some embodiments, the method comprises further administering an immune checkpoint inhibitor (see Lim & June, 2017. Cell. 168(4):724-740). In a further embodiment, the method comprises further administering an immune checkpoint inhibitor and/or an IAP inhibitor (see WO 2016/054555).

In some embodiments, the cell or pharmaceutical composition as described herein is administered in combination with chemotherapeutic agents and/or immunosuppressants. In an embodiment, a patient is first treated with a chemotherapeutic agent that inhibits or destroys other immune cells followed by the cell or pharmaceutical composition described herein. In some cases, chemotherapy may be avoided entirely.

In some embodiments, the CD1a-positive cancer is cortical T-cell acute lymphoblastic leukemia or Langerhans cell histiocytosis. In some embodiments, the CD1a-positive cancer is cortical T-cell acute lymphoblastic leukemia. In some embodiments, the CD1a-positive cancer is relapsed/refractory cortical T-cell acute lymphoblastic leukemia.

In general, the relapse of leukemia can manifest several months or years after the initial remission; however, most relapses occur within two years after the initial treatment. Refractoriness is a term that implies that the patient has no longer responded to at least one therapy strategy after a relapse.

There is a broad consensus in first-line trials for ALL, specifically in adults that a relapse is defined as "detection of more than 5% of blast cells in the bone marrow after a previous achievement of complete remission (CR) or unequivocal demonstration of extramedullary leukemia participation" (see Gökbuget (2017)). The European Working Group on Adult ALL (EWALL) has documented this statement in a consensus recommendation, (see Dohner (2010)) with the additional explanation that "in the case of 5 to 20% of cell blasts at some stage during the intensive treatment phase and/or during regeneration, the evaluation of the bone marrow should be repeated one week later to distinguish among bone marrow relapse and regeneration phenomenon". The cited definition is based on international recommendations for outcome parameters in acute myeloid leukemia (see Cheson (2003) and Chantepie (213)); that has been extrapolated to several subtypes of ALL, as in the case of T-ALL.

More recently, some trials did not even define the concept of relapse. Therefore, studies with chimeric antigen receptor (CAR) T cells included patients with "measurable disease" and also included patients with haematological relapse (no additional specification) or minimal residual disease (MRE) (see Lee (2015) and Maude (2014) and Gökbuget (2017)). Please refer to:

Dohner H, Estey E H, Amadori S, et al, Diagnosis and management of acute myeloid leukemia in adults: recommendations from an international expert panel, on behalf of the European Leukemia Net. Blood 2010; 115:453-74.

Cheson B D, Bennett J M, Kopecky K J, et al. Revised recommendations of the International Working Group for Diagnosis, Standardization of Response Criteria, Treatment Outcomes, and Reporting Standards for Therapeutic Trials in Acute Myeloid Leukemia. J Clin Oncol 2003; 21:4642-9.

Chantepie S P, Cornet E, Salaun V, Reman O. Hematogones: an overview. Leuk Res 2013; 37:1404-11.

13. Maude S L, Frey N, Shaw P A, et al. Chimeric antigen receptor T cells for sustained remissions in leukemia. N Engl J Med 2014; 371:1507-17.

Gökbuget N, Dombret H, Bassan R, Wadleigh M, Doubek M, Ribera J. Inclusion and response criteria for clinical trials in relapsed/refractory acute lymphoblastic leukemia and usefulness of historical control trials. *Haematologica.* 2017; 102(3): e118-e119.

In some embodiments, the patient to be treated with the method of the present invention is in complete or near-complete remission after treatment with another therapy. It may be preferable desirable to decrease the tumor burden before using the methods of the present invention because since there are several alternative effector T-cells in cases of patients with highly active relapsed/refractory cortical T-cell acute lymphoblastic leukemia. In some embodiments, the patient to be treated with the method of the present invention has previously been treated with another therapy which resulted in a partial response, complete response, stable disease, decrease in progressive disease, reduced time to tumor progression or any combination thereof.

EXAMPLES

Materials and Methods

CD1a-Specific scFv Generation and CAR Design

The CD1a-specific single-chain variable fragment (scFv) derived from the NA1/34.HLK clone of CD1a-specific antibody was obtained using commercial synthesis (Sigma-Aldrich) with the mouse IgG Library Primer Set (Progen), and was cloned into a pCCL lentiviral-based second-generation CAR backbone containing a human CD8 transmembrane (TM) domain, human CD137 and CD3 endodomains, and a T2A-GFP cassette. Identical lentiviral vectors expressing either GFP alone (mock vector) or CD22 CAR backbone were used as controls (FIGS. 1D & 8A).

CAR-Expressing Lentiviral Production, T-Cell Transduction, Activation and Expansion CAR-expressing viral particles pseudotyped with VSV-G were generated in 293T cells using a standard polyethylenimine transfection protocol, and were concentrated by ultracentrifugation as described elsewhere[27]. Viral titers were consistently in the range of $10^8$ TU/mL. Peripheral blood mononuclear cells (PBMCs) were isolated from buffy coats from healthy volunteers by Ficoll-Hypaque gradient centrifugation. Buffy coats were obtained from the Barcelona Blood and Tissue Bank (BST) upon IRB approval (HCB/2018/0030). T-cells were activated by plate-bound anti-CD3 (OKT3) and anti-CD28 antibodies (BD Biosciences) for 2 days and were then transduced with CAR-expressing lentivirus (MOI=10) in the presence of interleukin-7 (IL-7) and IL-15 (10 ng/mL, Mitenyi Biotec)[16,18]. The cell surface expression of CD1aCAR was traced by fluorescence-activated cell sorting (FACS) coexpression of GFP and was confirmed using an AffiniPure F(ab')2 Fragment Goat Anti-Mouse IgG (H+L) (Jackson ImmunoResearch). Proper activation of CAR-transduced T cells was demonstrated by staining for CD25 and CD69 after 2-day expansion.

Immunophenotyping of Healthy CD34+ Progenitors, T-Cells and Primary T-ALL Samples The expression of CD1a antigen in CD34+ stem/progenitor cells (HSPCs), CD34+CD7+ thymic T-cell progenitors and CD3+ T-cells was prospectively analyzed in fresh human thymus, fetal liver and bone marrow (BM), cord blood and adult BM and peripheral blood (PB) (n=3). Fetal tissue was collected as previously described[28,29] from developing embryos aborted at 18-22 weeks of pregnancy, obtained from the MRC/Wellcome Trust Human Developmental Biology Resource upon informed consent and approval by our local ethics and biozahard board committee (CMRBCEIC-26/2013). Neonatal and adult tissues were obtained from the BST upon IRB approval (HCB/2018/0030). Primary T-ALL samples and diagnostic immunophenotyping data were obtained from the local hospitals Sant Joan de Den, Germans Trias i Pujol, and Santa Creu i San Pau (Barcelona, Spain). For immunophenotyping of T-ALL primary samples, the following fluorochrome-conjugated monoclonal antibodies (MoAb) were used: anti-CD2-PE, CD7-FITC/PE, CD13-PerCP-Cy5.5, CD34-APC, CD3-PE, CD5-FITC, CD4-BV-421, CD8-APC-Cy7, CD45-AmCyan, CD1 a-BV-421/APC/PE, CD33-APC and CD123-APC (BDBiosciencies or Miltenyi Biotec). Isotype-matched, non-reactive fluorochrome-conjugated MoAb were always used as a fluorescence reference. Briefly, PB mononuclear cells (PBMCs, $5\times10^5$) were incubated with erythrocyte-lysing solution (BDBiosciencies) for 10 min and then stained with MoAb (20 min at 4° C. in the dark). Stained cells were washed in phosphate buffered saline (PBS) and analyzed by FACS on a FACSCanto-II flow cytometer equipped with FACSDiva software (BDBiosciencies)[30-32].

In Vitro Cytotoxicity Assays and Cytokine Release Determination

Cell lines Jurkat, MOLT4 and NALM6 were purchased from DSMZ (Braunschweig, Germany) and expanded according to DSMZ recommendations. Luciferase (Luc)/GFP-expressing cells were stably generated by retroviral transduction and FACS purification of GFP+ cells[33]. Target cells (cell lines and primary T-ALL blasts) were labeled with 3 μM eFluor670 (eBioscience) and incubated with CD1a, CD22 or mock CARTs at different Effector:Target (E:T) ratios for the indicated time periods. CART-mediated cytotoxicity was determined by analyzing the residual alive (7-AAD-) eFluor670+ target cells at each time point and E:T ratio. Absolute cell counts were determined using Trucount absolute count beads (BD Biosciences). Additionally, FACS-sorted CD3+CD1a– mature T-cells from the PB of cortical T-ALL patients at presentation were activated, transduced with CD1a CAR and tested against their eFluor670-labeled autologous CD1a+ T-ALL blasts. The production of the pro-inflammatory cytokines IL-2, TNFα and IFNγ was measured by ELISA (Human ELISA SET, BD Biosciences) in supernatants harvested after 16 hours.

In Vivo Jurkat and T-ALL Patient-Derived Xenograft (PDX) Models

Six- to 12-week-old nonobese diabetic (NOD)-Cg-Prkdcscid Il2rgtm1Wjl/SzJ (NSG) mice (The Jackson Laboratory) were bred and housed under pathogen-free conditions in the animal facility of the Barcelona Biomedical Research Park (PRBB). Mice were irradiated (2 Gy) and intravenously (i.v.) transplanted with 3×10⁶ Luc-GFP-expressing Jurkat cells or with 1×10⁶ primary cortical CD1a+ T-ALL blasts (primary and primograft-expanded)[34]. Between 1.5×10⁶ to 5×10⁶ CD1a or mock CARTs were i.v. infused 3 days later. When Luc-Jurkat cells were used, tumor burden was followed by bioluminescence (BLI) using the Xenogen IVIS 50 Imaging System (Perkin Elmer). To measure luminescence, mice received 150 mg/kg of D-luciferin intraperitoneally, and tumor burden was monitored at the indicated time points. Living Image software (Perkin Elmer) was used to visualize and calculate total luminescence. Tumor burden of primary T-ALL samples was followed-up by biweekly bleeding and FACS analysis. Mice were sacrificed when mock CARTs-treated animals were leukemic, and tumor burden (hHLA-ABC+hCD45+hCD1a+ graft) and CART persistence (hHLA-ABC+hCD45+hCD3+hCD1a–GFP+) was analysed in BM, PB and spleen by FACS. In re-challenge experiments, leukemia-free animals that had received an infusion of CD1a CARTs 5-6 weeks before were re-infused with either 1.5×10⁶ Luc-Jurkat cells or 1×10⁶ CD1a+ T-ALL primografts, and disease reappearance was followed-up by BLI and FACS, as above. All procedures were performed in compliance with the institutional animal care and usage committee of the PRBB (DAAM7393).

Enzyme-Linked Immunospot Assay (ELISpot)

ELISpot plates (Millipore) were coated with anti-human IFNγ antibody (1-D1K, Mabtech) and kept overnight at 4° C. Plates were then washed six times with PBS containing 1% fetal calf serum and then cells from three independent donors were plated at 5×10⁵ to 1×10⁶ cells/well and cultured in triplicate for 20 h at 37° C. and 5% CO2. We measured IFNγ-secreting cells in response to CEF at 1 μg/mL, a peptide pool of T-cell epitopes of Cytomegalovirus (CMV), Epstein-Barr virus (EBV) and Flu and to staphylococcal enterotoxin B (SEB) at 1 μg/mL as a positive control. Plates were then revealed with biotinylated anti-human IFNγ, streptavidin-alkaline phosphatase (Mabtech), as previously described[35,36]. The frequency of IFNγ-secreting cells was quantified using ImmunoCapture and ImmunoSpot software to calculate the number of IFNγ Spot Forming Units per 10⁵ (SFU).

Statistical Analysis

Data from at least three individual donors are shown in all figures, and experimental duplicates were always performed. At least five animals were used in each in vivo condition. All p-values were calculated by unpaired two-tailed Student's t-test using Prism software (GraphPad). Event-free-survival (EFS) of mice was determined using a Mantle-Cox test. A p-value <0.05 was considered statistically significant.

Example 1: CD1a Specifically Marks Cortical T-ALL Blasts

The shared expression of target antigens between CARTs and T-lineage blasts has limited immunotherapy approaches in T-ALL due to CART-related fratricide and potential life-threating T-cell aplasia. However, CD1a antigen is expressed in cortical T-ALLs, a major subset of T-ALLs (FIG. 1A,B), but is completely absent in functional T-cells in all extra-thymic tissues[25], and steady-state CD34+HSPCs lack CD1a expression in multiple hematopoietic sites across ontogeny (FIG. 1C). T-cell development is initiated within the thymus by a first colonizing $CD34^{high}CD7-CD1a-$ primitive HSPC with lympho-myeloid potential, which then differentiate in response to the thymic microenvironment into $CD34^{high}CD7+CD1a-$ early T-cell progenitors[37]. As they progress through thymic differentiation, T-cell progenitors maintain CD7 expression and gradually lose CD34 expression, whereas CD1a expression emerges and is transiently confined to cortical thymocytes[38] (FIG. 1E,F). Within the CD34+ thymic population, ~50% is represented by pre-cortical T-cell progenitors (CD34highCD7+CD1a–, 1 E,F (grey cells)), allowing us to hypothesize that CD1a may be a feasible and safe target for immunotherapy in R/R cortical T-ALL, which have a fatal outcome[3,39-41].

Example 2: CD1a-Redirected T-Cells (CD1a CARTs) Expand without T-Cell Fratricide We designed a second-generation CD1a CAR consisting of anti-CD1a scFv, a CD8 TM spacer, and intracellular signaling domains from 4-1BB (CD137) and CD3 coupled in-frame with GFP through a T2A sequence (FIG. 2A). The expression of the CD1a CAR was easily detected through coexpression of both scFv and GFP in 293T cells (FIG. 2B) and in primary CD4+ and CD8+ T-cell subsets (FIG. 2C). Importantly, activated (CD69+CD25+) CD1a CARTs (FIG. 2D) continuously expanded 200-fold over a 12-day period, similar to MOCK T-cells (FIG. 2E), demonstrating that redirecting CARTs against CD1a antigen does not induce T-cell fratricide.

Example 3: CD1a CARTs Specifically Eradicate T-ALL Cell Lines and Primary Blasts In Vitro CD1a CARTs were then tested in vitro using the CD1a+ T-ALL cell lines Jurkat and MOLT4, and the B-ALL cell line NALM6 as a negative control (FIG. 2F). Compared with control CARTs (either MOCK T-cells or CD22 CARTs), CD1a CARTs specifically eliminated CD1a+ T-ALL cells in a manner dependent on the E:T ratio. A relatively low E:T ratio of 2:1 or 4:1 induced 50-80% specific cell lysis in 16 h-assays (FIGS. 2H,I, 9). Importantly, barely any CD1a+ T-ALL cells survived exposure to CD1a CARTs in a 72 h-assay at a 1:1 E:T ratio (FIG. 2I). CD1a CARTs produced high levels of the pro-inflammatory cytokines IL-2, TNFα and IFNγ on co-culture with CD1a+ T-ALL cells confirming their action (FIG. 2K).

To further address their ability to eliminate primary tumors, CD1a CARTs were co-cultured with primary cortical T-ALL samples (either freshly harvested or PDX-derived), with a proportion of CD1a+ blasts ranging between 80% and 98% (FIG. 3A). Compared with MOCK T-cells, CD1a CARTs specifically eliminated primary CD1a+ cortical T-ALL cells in 72 h cytotoxicity assays at 4:1 E:T ratio (FIG. 3B,C). Normal hematopoietic cells (CD1a−) co-existing in BM with CD1a+ T-ALL blasts were not lysed by CD1a CARTs (FIG. 3C). High-levels of IFNγ and TNFα were also secreted on co-culture with CD1a+ primary T-ALL cells (FIG. 3D). Collectively, these results show that CD1a CARTs have a potent and specific anti-leukemic activity against T-ALL cell lines and primary blasts in vitro.

Example 4: CD1a CARTs Demonstrate Potent Anti-Leukemia Activity In Vivo

We next evaluated the activity of CD1a CARTs in vivo using both Luc-expressing Jurkat T-ALL cells (FIG. 4, 10) and a primary cortical T-ALL xenograft model[34] (FIG. 5). NSG mice were transplanted with $3 \times 10^6$ Luc-expressing Jurkat cells three days prior to i.v. infusion of either $2 \times 10^6$ or $5 \times 10^6$ CD1a (or MOCK) CARTs, and leukemia establishment was followed-up weekly by BLI (FIG. 4A, 10). In contrast to the mice receiving MOCK T-cells, which showed massive tumor burden by BLI, those mice receiving CD1a CARTs were practically leukemia-free by day 25 (FIG. 4B,C, 10). The control of leukemia progression was CD1a CART cell dose-dependent (FIG. 10B,C). Flow cytometry analysis of tumor burden in PB at sacrifice confirmed the BLI data (FIG. 4D). Importantly, FACS analysis revealed T-cell persistence in all hematopoietic tissues analyzed (FIG. 4E); however, we found a significantly increased biodistribution of CD1a CARTs in BM and spleen, as compared with T-cell biodistribution in mice receiving MOCK T-cells (FIG. 4E), indicative of an active control of disseminated leukemia by CD1a CARTs.

In a clinically more relevant PDX model of cortical T-ALL, NSG mice were first transplanted with $1 \times 10^6$ primary CD1a+ T-ALL blasts followed three days later by infusion of $1 \times 10^6$ CD1a (or MOCK) CARTs, and leukemia engraftment was then followed-up bi-weekly by bleeding and endpoint BM analysis (FIG. 5A). Engraftment of CD1a+ cortical T-ALL cells gradually increased over time both in BM (FIG. 5B, 50%±13% and 55%±11% on week 6 and 9, respectively) and PB (FIG. 5C, 4.4%±2% and 18%±6% on week 6 and 9, respectively) in MOCK T-cells-treated PDXs, and associated with a significantly lower 9-week OS (42% vs 100%, p=0.01; FIG. 5D). In contrast, CD1a CARTs fully abolished T-ALL growth/engraftment (0.36% and 0% T-ALL blasts in BM and PB, respectively) and they persisted in BM and PB after 9 weeks (FIG. 5B,C,E).

Example 5: In Vivo Persistent CD1a CARTs are Functional in Re-Challenge Assays

Because the persistence of CARTs in hematopoietic tissues is a major biological parameter for their clinical success, we next assessed whether CD1a CARTs persisting after 40-50 days remained functional and efficient in controlling T-ALL progression. To do this, T-ALL-transplanted mice in which the leukemia was abolished on treatment with CD1a CARTs were rechallenged with either Luc-Jurkat cells (FIG. 6A-D) or primary T-ALLs from a primograft (FIG. 6E-G). In contrast to controls in which the secondary leukemias rapidly (as soon as 2 weeks after) and massively engrafted, T-ALL engraftment was barely detectable by either BLI or FACS in the Jurkat (FIG. 6C) or primograft model after 6 weeks (FIG. 6F).

Example 6: Patient-Derived CD1a CARTs Specifically Target Autologous CD1a+ Blasts and Retain Antiviral Activity The proper choice of the target antigen and avoiding T-cell fratricide are crucial for the success of CARTs in the treatment of T-ALL. Accordingly, we examined whether PB-derived CD3+CD1a− T-cells from patients with cortical T-ALL can be isolated and genetically modified to express CD1a CAR (FIG. 7). Thus, CD3+CD1a− T-cells from patients were isolated (>95% purity, data not shown), activated with CD3/CD28 and lentivirally transduced (31-70% transduction) with CD1a CAR or MOCK. Next, we investigated the cytolytic capacity of CD1a CARTs derived from primary T-ALLs against active T-ALL patient-matched PBMCs (FIG. 7A). Total PBMCs were used as targets because it allows us to assess both the autologous cytotoxicity potential and the degree of fratricide. Within eFluor670-labelled target PBMCs, the great majority are CD1a+ blasts and ~15% are CD3+CD1a− normal T-cells (FIG. 7B). As compared with MOCK T-cells, the CD1a CARTs showed a massive and specific cytolytic capacity against autologous CD1a+ blasts but not against CD1a− normal T-cells (FIG. 6B), further demonstrating that CD1a CARTs are fratricide-resistant.

To further assess the potential thymic toxicity of CD1a CARTs, we next used human normal fetal thymus-derived CD7+ thymocytes as target cells. Only the CD1a+ cortical thymocytes (second and third grey box) were eliminated by the CD1a CARTs, whereas developmentally earlier and later CD1a− (first box) thymic T-lineage populations (CD7+ CD34+ and CD7+CD34−) were not targeted (FIG. 1E,F), limiting the on-target/off-tumor effects to a developmentally transient thymic population of cortical thymocytes. We finally sought to determine whether CD1a CARTs can protect, by themselves, the host by targeting the most common pathogens causing viremia in immunosuppressed patients. To do this, we tested the reactivity of CD1a CARTs to CMV, EBV and Flu antigens (CEF) and quantified the SCFs by IFNγ ELISpot. Both MOCK T-cells and CD1a CARTs responded very similarly to stimulation with viral peptides, suggesting that CD1a CARTs retain antiviral activity (FIG. 7D).

BIBLIOGRAPHY

1. Kaltman K, Johansson B. Pediatric T-cell acute lymphoblastic leukemia. *Genes Chromosomes Cancer.* 2017; 56(2):89-116.

2. Weng A P, Ferrando A A, Lee W, et al. Activating mutations of NOTCH1 in human T cell acute lymphoblastic leukemia. *Science.* 2004; 306(5694):269-271.
3. Hunger S P, Mulligan C G. Acute Lymphoblastic Leukemia in Children. *N Engl J Med.* 2015; 373(16): 1541-1552.
4. Litzow M R, Ferrando A A. How I treat T-cell acute lymphoblastic leukemia in adults. *Blood.* 2015; 126(7): 833-841.
5. Schneider N R, Carroll A J, Shuster J J, et al. New recurring cytogenetic abnormalities and association of blast cell karyotypes with prognosis in childhood T-cell acute lymphoblastic leukemia: a pediatric oncology group report of 343 cases. *Blood.* 2000; 96(7):2543-2549.
6. Ballerini P, Landman-Parker J, Cayuela J M, et al. Impact of genotype on survival of children with T-cell acute lymphoblastic leukemia treated according to the French protocol FRALLE-93: the effect of TLX3/HOX11L2 gene expression on outcome. *Haematologica.* 2008; 93(11): 1658-1665.
7. Karrman K, Forestier E, Heyman M, et al. Clinical and cytogenetic features of a population-based consecutive series of 285 pediatric T-cell acute lymphoblastic leukemias: rare T-cell receptor gene rearrangements are associated with poor outcome. *Genes Chromosomes Cancer.* 2009; 48(9):795-805.
8. Sutton R, Shaw P J, Venn N C, et al. Persistent MRD before and after allogeneic BMT predicts relapse in children with acute lymphoblastic leukaemia. *Br J Haematol.* 2015; 168(3):395-404.
9. Qasim W, Thrasher A J. Progress and prospects for engineered T cell therapies. *Br J Haematol.* 2014; 166 (6):818-829.
10. Humphries C. Adoptive cell therapy: Honing that killer instinct. *Nature.* 2013; 504(7480):S13-15.
11. Brentjens R J, Davila M L, Riviere I, et al. CD19-targeted T cells rapidly induce molecular remissions in adults with chemotherapy-refractory acute lymphoblastic leukemia. *Sci Transl Med.* 2013; 5(177): 177ra138.
12. Maude S L, Frey N, Shaw P A, et al. Chimeric antigen receptor T cells for sustained remissions in leukemia. *N Engl J Med.* 2014; 371(16): 1507-1517.
13. Gardner R A, Finney O, Annesley C, et al. Intent-to-treat leukemia remission by CD19 CART cells of defined formulation and dose in children and young adults. *Blood.* 2017; 129(25):3322-3331.
14. Fry T J, Shah N N, Orentas R J, et al. CD22-targeted CAR T cells induce remission in B-ALL that is naive or resistant to CD19-targeted CAR immunotherapy. *Nat Med.* 2018; 24(1):20-28.
15. Cooper M L, Choi J, Staser K, et al. An "off-the-shelf1 fratricide-resistant CAR-T for the treatment of T cell hematologic malignancies. *Leukemia.* 2018.
16. Gomes-Silva D, Srinivasan M, Sharma S, et al. CD7-edited T cells expressing a CD7-specific CAR for the therapy of T-cell malignancies. *Blood.* 2017; 130(3):285-296.
17. Png Y T, Vinanica N, Kamiya T, Shimasaki N, Coustan-Smith E, Campana D. Blockade of CD7 expression in T cells for effective chimeric antigen receptor targeting of T-cell malignancies. *Blood Adv.* 2017; 1(25):2348-2360.
18. Mamonkin M, Rouce R H, Tashiro H, Brenner M K. A T-cell-directed chimeric antigen receptor for the selective treatment of T-cell malignancies. *Blood.* 2015; 126(8): 983-992.
19. Rasaiyaah J, Georgiadis C, Preece R, Mock U, Qasim W. TCRalphabeta/CD3 disruption enables CD3-specific antileukemic T cell immunotherapy. *JCIInsight.* 2018; 3(13).
20. Maciocia P M, Wawrzyniecka P A, Philip B, et al. Targeting the T cell receptor beta-chain constant region for immunotherapy of T cell malignancies. *Nat Med.* 2017; 23(12): 1416-1423.
21. Bene M C, Castoldi G, Knapp W, et al. Proposals for the immunological classification of acute leukemias. European Group for the Immunological Characterization of Leukemias (EGIL). *Leukemia.* 1995; 9(10): 1783-1786.
22. Burger R, Hansen-Hagge T E, Drexler H G, Gramatzki M. Heterogeneity of T-acute lymphoblastic leukemia (T-ALL) cell lines: suggestion for classification by immunophenotype and T-cell receptor studies. *Leuk Res.* 1999; 23(1): 19-27.
23. Niehues T, Kapaun P, Harms D O, et al. A classification based on T cell selection-related phenotypes identifies a subgroup of childhood T-ALL with favorable outcome in the COALL studies. *Leukemia.* 1999; 13(4):614-617.
24. van Grotel M, Meijerink J P, van Wering E R, et al. Prognostic significance of molecular cytogenetic abnormalities in pediatric T-ALL is not explained by immunophenotypic differences. *Leukemia.* 2008; 22(1): 124-131.
25. Bechan G I, Lee D W, Zajonc D M, et al. Phage display generation of a novel human anti-CD1A monoclonal antibody with potent cytolytic activity. *Br J Haematol.* 2012; 159(3):299-310.
26. Carrera Silva E A, Nowak W, Tessone L, et al. CD207 (+)CD1a(+) cells circulate in pediatric patients with active Langerhans cell histiocytosis. *Blood.* 2017; 130(17): 1898-1902.
27. Prieto C, Stam R W, Agraz-Doblas A, et al. Activated KRAS Cooperates with MLL-AF4 to Promote Extramedullary Engraftment and Migration of Cord Blood CD34+ HSPC But Is Insufficient to Initiate Leukemia. *Cancer Res.* 2016; 76(8):2478-2489.
28. Munoz-Lopez A, van Roon E H, Romero-Moya D, et al. Cellular Ontogeny and Hierarchy Influence the Reprogramming Efficiency of Human B Cells into Induced Pluripotent Stem Cells. *Stem Cells.* 2016; 34(3):581-587.
29. Munoz-Lopez A, Romero-Moya D, Prieto C, et al. Development Refractoriness of MLLRearranged Human B Cell Acute Leukemias to Reprogramming into Pluripotency. *Stem Cell Reports.* 2016; 7(4):602-618.
30. Bueno C, Roldan M, Anguita E, et al. Bone marrow mesenchymal stem cells from patients with aplastic anemia maintain functional and immune properties and do not contribute to the pathogenesis of the disease. *Haematologica.* 2014; 99(7): 1168-1175.
31. Menendez P, Catalina P, Rodriguez R, et al. Bone marrow mesenchymal stem cells from infants with MLL-AF4+ acute leukemia harbor and express the MLL-AF4 fusion gene. *J Exp Med.* 2009; 206(13):3131-3141.
32. Rodriguez R, Tornin J, Suarez C, et al. Expression of FUS-CHOP fusion protein in immortalized/transformed human mesenchymal stem cells drives mixoid liposarcoma formation. *Stem Cells.* 2013; 31(10):2061-2072.
33. Recasens-Zorzo C, Cardesa-Salzmann T, Petazzi P, et al. Pharmacological modulation of CXCR4 cooperates with BET bromodomain inhibition in diffuse large B-cell lymphoma. *Haematologica.* 2018.
34. Garcia-Peydro M, Fuentes P, Mosquera M, et al. The NOTCH1/CD44 axis drives pathogenesis in a T cell acute lymphoblastic leukemia model. *J Clin Invest.* 2018.

35. Dalmau J, Rotger M, Erkizia I, et al. Highly pathogenic adapted HIV-1 strains limit host immunity and dictate rapid disease progression. *AIDS.* 2014; 28(9): 1261-1272.
36. Addo M M, Yu X G, Rathod A, et al. Comprehensive epitope analysis of human immunodeficiency virus type 1 (HIV-1)-specific T-cell responses directed against the entire expressed HIV-1 genome demonstrate broadly directed responses, but no correlation to viral load. *J Virol.* 2003; 77(3):2081-2092.
37. Martin-Gayo E, Gonzalez-Garcia S, Garcia-Leon M J, et al. Spatially restricted JAG1-Notch signaling in human thymus provides suitable DC developmental niches. *J Exp Med.* 2017; 214(11):3361-3379.
38. Galy A, Verma S, Barcena A, Spits H. Precursors of CD3+CD4+CD8+ cells in the human thymus are defined by expression of CD34. Delineation of early events in human thymic development. *J Exp Med.* 1993; 178(2): 391-401.
39. Lepretre S, Graux C, Touzart A, Macintyre E, Boissel N. Adult T-type lymphoblastic lymphoma: Treatment advances and prognostic indicators. *Exp Hematol.* 2017; 51:7-16.
40. Marks D I, Paietta E M, Moorman A V, et al. T-cell acute lymphoblastic leukemia in adults: clinical features, immunophenotype, cytogenetics, and outcome from the large randomized prospective trial (UKALL XII/ECOG 2993). *Blood.* 2009; 114(25):5136-5145.
41. Mendes R D, Cante-Barrett K, Pieters R, Meijerink J P. The relevance of PTEN-AKT in relation to NOTCH1-directed treatment strategies in T-cell acute lymphoblastic leukemia. *Haematologica.* 2016; 101(9): 1010-1017.
42. LeMaistre C F, Rosen S, Frankel A, et al. Phase I trial of H65-RTA immunoconjugate in patients with cutaneous T-cell lymphoma. *Blood.* 1991; 78(5): 1173-1182.
43. Frankel A E, Laver J H, Willingham M C, Burns U, Kersey J H, Vallera D A. Therapy of patients with T-cell lymphomas and leukemias using an anti-CD7 monoclonal antibody-ricin A chain immunotoxin. *Leuk Lymphoma.* 1997; 26(3-4):287-298.
44. Junca J, Botin T, Vila J, Navarro J T, Milla F. Adult T-cell leukemia/lymphoma with an unusual CD1a positive phenotype. *Cytometry B Clin Cytom.* 2014; 86(4):292-296.
45. van den Broek T, Madi A, Delemarre E M, et al. Human neonatal thymectomy induces altered Bcell responses and autoreactivity. *Eur J Immunol.* 2017; 47(11): 1970-1981.
46. Kurobe H, Tominaga T, Sugano M, et al. Complete but not partial thymectomy in early infancy reduces T-cell-mediated immune response: three-year tracing study after pediatric cardiac surgery. *J Thorac Cardiovasc Surg.* 2013; 145(3):656-662, 662 e651-652; discussion 662.
47. van den Broek T, Delemarre E M, Janssen W J, et al. Neonatal thymectomy reveals differentiation and plasticity within human naive T cells. *J Clin Invest.* 2016; 126(3): 1126-1136.

The invention claimed is:

1. A method of treating a CD 1a-positive cancer in a subject in need thereof, said method comprising administering to said subject a CD1a-negative allo-tolerant T cell comprising a nucleic acid encoding a chimeric antigen receptor (CAR) comprising:
   (i) an extracellular domain comprising a CD 1a targeting-moiety, wherein the CD 1a targeting moiety is an antibody, scFv, Fab, or scFab comprising a VL domain and VH domain,
      wherein said VL domain comprises LCDR1, LCDR2 and LCDR3 polypeptides and said VH domain comprises HCDR1, HCDR2 and HCDR3 polypeptides, and LCDR1 consists of QDINKY (SEQ ID NO: 1), LCDR2 consists of YTS, LCDR3 consists of LHYDNLPWT (SEQ ID NO: 3), HCDR1 consists of GYAFSTYT (SEQ ID NO: 4), HCDR2 consists of INPNSAST (SEQ ID NO: 5), and HCDR3 consists of ARGFYTMDY (SEQ ID NO: 6);
   (ii) a transmembrane domain; and
   (iii) an intracellular signaling domain.

2. The method according to claim 1, wherein the transmembrane domain comprises the transmembrane domain of CD28, CD3, CD45, CD4, CD8, CD9, CD16, CD22, CD33, CD37, CD64, CD80, CD86, CD134, CD 137, or CD154.

3. The method according to claim 2, wherein the transmembrane domain comprises the transmembrane domain of CD8.

4. The method according to claim 1, wherein the intracellular signaling domain comprises the intracellular domain of CD3ξ, FcRγ, CD3γ, CD3δ, CD3ε, CD5, CD22, CD79a, CD79b or CD66b.

5. The method according to claim 4, wherein the intracellular signaling domain comprises the intracellular domain of CD3ξ.

6. The method according to claim 1, wherein the CAR further comprises a costimulatory signaling domain.

7. The method according to claim 6, wherein the costimulatory signaling domain comprises the intracellular domain of CD27, CD28, CD137, CD134, CD30, CD40, lymphocyte function-associated antigen-1 (LFA-1), CD2, CD7, LIGHT, NKG2C, CD278 or CD276.

8. The method according to claim 7, wherein the costimulatory signaling domain comprises the intracellular domain of CD137.

9. The method according to claim 1, wherein the CD 1a-positive cancer is cortical T-cell acute lymphoblastic leukemia.

10. The method according to claim 9, wherein the CD 1a-positive cancer is relapsed/refractory cortical T-cell acute lymphoblastic leukemia.

11. The method according to claim 1, wherein the CD 1a-positive cancer is CD 1a+ T-cell lymphoblastic lymphoma.

12. The method according to claim 11, wherein the CD 1a-positive cancer is relapsed/refractory CD1a+ T-cell lymphoblastic lymphoma.

13. A method of treating a CD 1a-positive cancer in a subject in need thereof, said method comprising administering to said subject a pharmaceutical composition comprising a plurality of T cells as defined in claim 1 and a pharmaceutically acceptable carrier or diluent.

14. The method according to claim 13, wherein the CD 1a-positive cancer is cortical T-cell acute lymphoblastic leukemia.

15. The method according to claim 14, wherein the CD 1a-positive cancer is relapsed/refractory cortical T-cell acute lymphoblastic leukemia.

16. The method according to claim 13, wherein the CD 1a-positive cancer is CD1a+ T-cell lymphoblastic lymphoma.

17. The method according to claim 16, wherein the CD 1a-positive cancer is relapsed/refractory CD1a+ T-cell lymphoblastic lymphoma.

* * * * *

UNITED STATES PATENT AND TRADEMARK OFFICE
CERTIFICATE OF CORRECTION

PATENT NO. : 12,215,158 B2
APPLICATION NO. : 17/430705
DATED : February 4, 2025
INVENTOR(S) : Pablo Menéndez Buján et al.

Page 1 of 1

It is certified that error appears in the above-identified patent and that said Letters Patent is hereby corrected as shown below:

On the Title Page

Item [71], please replace applicant name:
"…INSTITUCIO′
CATALANA DE RECERCA I
ESTUDIS AVANC ATS(ICREA),
Barcelona (ES)…"

With:
--"…INSTITUCIO′
CATALANA DE RECERCA I
ESTUDIS AVANÇATS (ICREA),
Barcelona (ES)…"--.

Item [73], please replace assignee name:
"…INSTITUCIO′
CATALANA DE RECERCA I
ESTUDIS AVANATS (ICREA),
Barcelona (ES)…"

With:
--"…INSTITUCIO′
CATALANA DE RECERCA I
ESTUDIS AVANÇATS (ICREA),
Barcelona (ES)…"--.

Signed and Sealed this
Eighteenth Day of March, 2025

Coke Morgan Stewart
*Acting Director of the United States Patent and Trademark Office*